US012150702B1

(12) United States Patent
Narayan et al.

(10) Patent No.: US 12,150,702 B1
(45) Date of Patent: Nov. 26, 2024

(54) GENERATOR AND CATHETER FOR TISSUE ABLATION

(71) Applicant: PhysCade, Inc., Palo Alto, CA (US)

(72) Inventors: Sanjiv M. Narayan, Palo Alto, CA (US); Bret Anders Herscher, Cupertino, CA (US); David Krawzsenek, Mountain View, CA (US)

(73) Assignee: PhysCade, Inc., Palo Alto, CA (US)

( * ) Notice: Subject to any disclaimer, the term of this patent is extended or adjusted under 35 U.S.C. 154(b) by 0 days.

(21) Appl. No.: 18/733,393

(22) Filed: Jun. 4, 2024

Related U.S. Application Data

(60) Provisional application No. 63/655,579, filed on Jun. 3, 2024.

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00023* (2013.01);
(Continued)

(58) Field of Classification Search
CPC . A61B 18/1206; A61B 18/1233; A61B 18/14; A61B 18/1445; A61B 18/16; A61B 2018/00577; A61B 2018/00589; A61B 2018/00601; A61B 2018/0063; A61B 2018/00648; A61B 2018/00684;
(Continued)

(56) References Cited

U.S. PATENT DOCUMENTS 4,411,266 A 10/1983 Cosman
4,966,597 A 10/1990 Cosman
(Continued)

FOREIGN PATENT DOCUMENTS

WO WO 1998/019595 A1 5/1998
WO WO 2017/120169 A1 7/2017

OTHER PUBLICATIONS

U.S. Appl. No. 63/396,450, filed Aug. 9, 2022, Inventors Sanjiv M. Narayan, Dylan R. Montgomery, Steven D. Thompson, Jonathan S. Ciulla, Peter J. D'Aquanni, Andy E. Denison, Melissa Donovan-Green, Jose Alvarado, Mahmood I. Alhusseini, Bret A. Herscher.

*Primary Examiner* — Michael F Peffley
*Assistant Examiner* — Amanda L Zink
(74) *Attorney, Agent, or Firm* — Fenwick & West LLP

(57) ABSTRACT

An ablation treatment catheter may include a first conductive wire formed of a first material. The first conductive wire is configured to be connected to a power generator and to carry a current to deliver ablation energy to a biological tissue. The catheter may include a second wire coupled to the first conductive wire. The second wire formed of a second material. The second wire forming a junction with the first conductive wire. The catheter may include a first electrode comprising an ablation element and a temperature sensor. The ablation element includes part of the first conductive wire and is configured to deliver the ablation energy to the biological tissue. The temperature sensor includes the junction of the first conductive wire and the second wire such that a thermocouple is formed at the junction to measure temperature at the first electrode.

28 Claims, 27 Drawing Sheets

(52) U.S. Cl.
CPC ............... *A61B 2018/00077* (2013.01); *A61B 2018/00351* (2013.01); *A61B 2018/00577* (2013.01); *A61B 2018/0072* (2013.01); *A61B 2018/00821* (2013.01); *A61B 2018/128* (2013.01)

(58) Field of Classification Search
CPC .. A61B 2018/00702; A61B 2018/0072; A61B 2018/00767; A61B 2018/00827; A61B 2018/00875; A61B 2018/00892; A61B 2018/00898; A61B 2018/167; A61B 2560/0238

See application file for complete search history.

(56) References Cited

U.S. PATENT DOCUMENTS

| | | | |
|---|---|---|---|
| 5,590,657 A * | 1/1997 | Cain | ................ A61B 17/2256 601/3 |
| 6,190,379 B1 | 2/2001 | Heuser et al. | |
| 6,425,894 B1 | 7/2002 | Brucker et al. | |
| 6,692,492 B2 | 2/2004 | Simpson et al. | |
| 7,179,256 B2 | 2/2007 | Mest | |
| 7,306,596 B2 | 12/2007 | Hillier et al. | |
| 7,569,052 B2 | 8/2009 | Phan et al. | |
| 7,879,029 B2 | 2/2011 | Jimenez | |
| 8,187,268 B2 | 5/2012 | Godara et al. | |
| 8,641,704 B2 | 2/2014 | Werneth et al. | |
| 8,641,708 B2 | 2/2014 | Govari et al. | |
| 8,668,686 B2 | 3/2014 | Govari et al. | |
| 9,005,192 B2 | 4/2015 | Govari et al. | |
| 9,333,033 B2 | 5/2016 | Gliner | |
| 9,445,725 B2 | 9/2016 | Govari et al. | |
| 9,814,524 B2 | 11/2017 | Jimenez | |
| 9,956,035 B2 | 5/2018 | Govari et al. | |
| 9,987,081 B1 | 6/2018 | Bowers et al. | |
| 10,206,733 B2 | 2/2019 | Govari et al. | |
| 10,213,248 B2 | 2/2019 | Bar-Tal et al. | |
| 10,729,485 B2 | 8/2020 | Govari et al. | |
| 10,751,120 B2 | 8/2020 | Schultz et al. | |
| 10,869,719 B2 | 12/2020 | Harlev et al. | |
| 10,939,956 B2 | 3/2021 | Harlev et al. | |
| 11,020,178 B2 | 6/2021 | Govari et al. | |
| 11,033,236 B2 | 6/2021 | Viswanathan et al. | |
| 11,116,563 B2 | 9/2021 | Levin et al. | |
| 11,147,610 B2 | 10/2021 | Govari et al. | |
| 11,159,124 B2 | 10/2021 | Govari et al. | |
| 11,185,366 B2 | 11/2021 | Govari et al. | |
| 11,213,347 B2 | 1/2022 | Govari et al. | |
| 11,357,978 B2 | 6/2022 | Bowers et al. | |
| 11,432,872 B2 | 9/2022 | Govari et al. | |
| 11,490,958 B2 | 11/2022 | Harlev et al. | |
| 11,555,846 B2 | 1/2023 | Levin et al. | |
| 11,660,135 B2 | 5/2023 | Govari et al. | |
| 11,684,408 B2 | 6/2023 | Paré et al. | |
| 11,712,284 B2 | 8/2023 | Levin et al. | |
| 11,737,680 B2 | 8/2023 | Yellin et al. | |
| 11,819,268 B2 | 11/2023 | Govari et al. | |
| 2004/0054282 A1 * | 3/2004 | Aubry | ....................... A61B 8/15 600/437 |
| 2008/0058657 A1 | 3/2008 | Schwartz et al. | |
| 2009/0306641 A1 | 12/2009 | Govari et al. | |
| 2011/0270247 A1 | 11/2011 | Sherman | |
| 2017/0312008 A1 | 11/2017 | Harlev | |
| 2020/0022747 A1 | 1/2020 | Zilberman et al. | |
| 2020/0085497 A1 | 3/2020 | Zhang et al. | |
| 2021/0022794 A1 | 1/2021 | Viswanathan | |
| 2021/0022803 A1 * | 1/2021 | Olson | ................ A61B 18/1492 |
| 2021/0220043 A1 * | 7/2021 | Iranitalab | ........... A61B 18/1492 |
| 2022/0110674 A1 * | 4/2022 | Taylor | ................ A61B 18/1485 |
| 2022/0226035 A1 * | 7/2022 | Møller | ................... A61B 18/16 |
| 2023/0049942 A1 * | 2/2023 | Narayan | ............. A61B 18/1492 |
| 2023/0061561 A1 * | 3/2023 | Jimenez | ............. A61B 18/1492 |
| 2023/0190370 A1 | 6/2023 | Govari et al. | |
| 2023/0200897 A1 * | 6/2023 | Borjian | ............. A61M 25/1025 606/41 |

* cited by examiner

*400 kHz Harmonic Filter Nominal and Wors-case transfer function.*

```
┌─────────────────────────────────────────────────────────────┐
│  APPLY A CATHETER TO A BIOLOGICAL ISSUE, THE CATHETER       │
│  COMPRISING AN ELECTRODE CONFIGURED TO DELIVER ABLATION     │
│  ENERGY TO THE BIOLOGICAL TISSUE, THE ELECTRODE COMPRISING A│
│  JUNCTION OF TWO DIFFERENT MATERIALS                        │
│                          1410                                │
└─────────────────────────────────────────────────────────────┘
                              │
                              ▼
┌─────────────────────────────────────────────────────────────┐
│  MEASURE, SIMULTANEOUSLY FOR AT LEAST A MOMENT, A           │
│  THERMOCOUPLE VOLTAGE AT THE JUNCTION OF THE TWO DIFFERENT  │
│                       MATERIALS                              │
│                          1420                                │
└─────────────────────────────────────────────────────────────┘
                              │
                              ▼
┌─────────────────────────────────────────────────────────────┐
│  DETERMINE A TEMPERATURE OF THE ELECTRODE BASED ON THE      │
│              THERMOCOUPLE VOLTAGE                            │
│                          1430                                │
└─────────────────────────────────────────────────────────────┘
                              │
                              ▼
┌─────────────────────────────────────────────────────────────┐
│  REGULATE A POWER GENERATOR THAT GENERATES A CURRENT        │
│  DELIVERED TO THE ELECTRODE OF THE CATHETER BASED ON THE    │
│                      TEMPERATURE                             │
│                          1440                                │
└─────────────────────────────────────────────────────────────┘
```

FIG. 14

GENERATOR AND CATHETER FOR TISSUE ABLATION

CROSS-REFERENCE TO RELATED APPLICATION(S)

The application claims the benefit of U.S. provisional patent application No. 63/655,579, filed on Jun. 3, 2024, which is incorporated by reference herein for all purposes.

FIELD

The disclosed embodiments relate to systems for the treatment of biological rhythm disorders, specifically including generators designed to deliver energy to catheters in a precisely controlled fashion to modify biological tissue to treat disease and maintain health.

BACKGROUND

Conventional invasive treatment of biological rhythm disorders uses separate catheters for sensing and mapping electrical tissue signals and distinct catheters for the ablation of critical regions (also termed sources) for biological rhythm disorders. The use of separate catheters introduces limitations and can result in unsynchronized positioning and movement of mapping and therapy catheters, requires logic or software systems to reconcile differences between catheter signals or positions, extends the length of the procedure to enable catheter exchanges which reduces efficiency and may introduce side-effects including air or clot into the bloodstream.

Ablation catheters face a myriad of challenges when tasked with modifying biological tissue, particularly within the intricate environment of the heart. For example, the regulation of temperature is challenging. In an ablation procedure, improper temperature may cause tissue damage or incomplete ablation. The confined space within the heart presents further obstacles, requiring catheters to navigate through narrow passages and intricate structures with unparalleled accuracy. Additionally, the potential for heating the blood poses a significant concern. The heat generated during ablation can inadvertently affect the surrounding blood, potentially leading to coagulation or thrombus formation, further complicating the procedure and posing risks to the patient's health. Addressing these challenges demands advanced technology and meticulous procedural planning to ensure the efficacy and safety of ablation therapies.

SUMMARY

The present disclosure relates to a catheter for ablating tissue, for example for treating a heart rhythm disorder, the catheter including: a first conductive wire formed of a first material, the first conductive wire configured to be connected to a power generator and to carry a current to deliver ablation energy to a biological tissue; a second wire coupled to the first conductive wire, the second wire formed of a second material different from the first material, the second wire forming a junction with the first conductive wire; and a first electrode including an ablation element and a temperature sensor, wherein the ablation element includes part of the first conductive wire and is configured to deliver the ablation energy to the biological tissue, and wherein the temperature sensor includes the junction of the first conductive wire and the second wire such that a thermocouple between the first conductive wire and the second wire is formed at the junction to measure temperature at the first electrode.

In some embodiments, the techniques described herein relate to a power generator for generating ablating energy for a catheter to treat tissue, for example in relation to a heart rhythm disorder, the power generator including: a first power driver having a first port configured to be connected to a first wire of a first electrode of the catheter to deliver a first current to the first electrode to generate first ablation energy for treatment of a biological tissue; a second power driver having a second port configured to be connected to a second wire of a second electrode of the catheter to deliver a second current to the second electrode to generate second ablation energy for treatment of the biological tissue, wherein the first power driver and the second power driver are capable of generating different currents and delivering the different currents respectively to the first electrode and the second electrode of the catheter; a first voltage sensor configured to measure a first thermocouple voltage corresponding to the first wire of the first electrode of the catheter; a second voltage sensor configured to measure a second thermocouple voltage corresponding to the second wire of the second electrode of the catheter; and a controller configured to determine a first temperature corresponding to the first electrode based on the first thermocouple voltage and a second temperature corresponding to the second electrode based on the second thermocouple voltage.

In some embodiments, the techniques described herein relate to a system for ablating tissue including to treat a heart rhythm disorder, the system including: a catheter for ablating tissue to treat a heart rhythm disorder, the catheter including: a first conductive wire formed of a first material, the first conductive wire configured to deliver ablation energy to a biological tissue; a second wire coupled to the first conductive wire, the second wire formed of a second material different from the first material; and an electrode including a junction of the first conductive wire and the second wire; a power generator coupled to the catheter for powering the catheter, the power generator including: a power driver configured to be connected to the first conductive wire of the catheter to deliver a current to the electrode to deliver the ablation energy; and a voltage sensor configured to measure a thermocouple voltage at the junction of the first conductive wire and the second wire.

In some embodiments, the techniques described herein relate to a method for ablating tissue, for example to treat a heart rhythm disorder, the method including: applying a catheter to a biological issue, the catheter including an electrode configured to deliver ablation energy to the biological tissue, the electrode including a junction of two different materials; measuring, simultaneously for at least a moment, a thermocouple voltage at the junction of the two different materials; determining a temperature of the electrode based on the thermocouple voltage; and regulating a power generator that generates a current delivered to the electrode of the catheter based on the temperature.

BRIEF DESCRIPTION OF THE DRAWINGS

FIG. 3B illustrates a distal cross-section view of the shaft, in accordance with some embodiments.

FIG. 3E illustrates a distal cross-section view of the shaft, in accordance with some embodiments.

FIG. 14 is a flowchart depicting a process for ablating tissue to treat a rhythm disorder, in accordance with some embodiments.

Figure 1A:
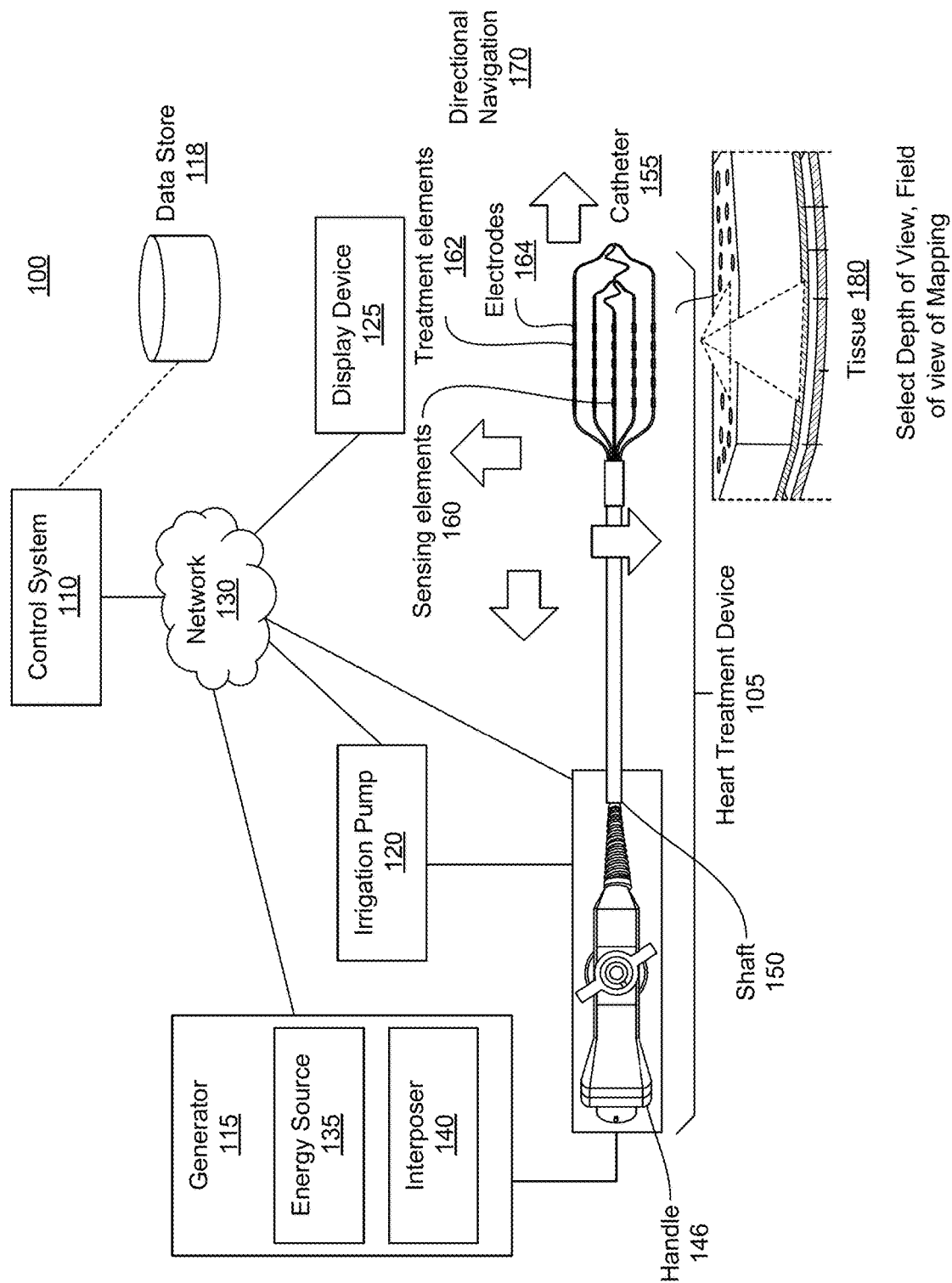
FIG. 1A illustrates an environment for the operation of a heart treatment device, in accordance with some embodiments.

In each figure, there can be more or fewer components and/or steps than shown, or certain components and/or steps can be replaced with others or can be organized or ordered in a different manner than is shown.

DETAILED DESCRIPTION

Overview

The present disclosure relates to a novel sensing and power delivery system for use in the diagnosis and ablation of biological tissue. A treatment system may include a generator and sensing system designed to efficiently control power delivery to a probe, using an efficient small number of wires. Sensing can include several biosignals including electrical signals, temperature, or other types. In some embodiments, temperature sensing does not require a separate wire and separate thermal sensor but instead uses existing sensing and power wires whose junction forms a natural thermocouple (thermal sensor). This provides the added advantage of accuracy: sensing temperature precisely at the electrode site of power delivery, rather than from a separate thermal sensor. The electronic design enables a very rapid increase or decrease in power to keep desired biosignals within a specified range. Power is provided by alternating current of varying frequencies which can result in the delivery of radiofrequency energy, pulsed-field energy, and a variety of other modalities. The power generator is flexible and designed to work with a variety of catheters which present a plurality of elements, electrodes, or probes.

Embodiments in this disclosure are scaleable to perform the above functions simultaneously on a wide variety of interchangeable catheters without any redesign. Some embodiments that use sensing and power delivery without the need for additional sensors simplify diagnosis and treatment and make it more efficient as a simpler probe design can now enable diagnosis, and closed-loop ablation to maintain a biosignal within its desired range. Coupled with a catheter with a plurality of elements, the invention is capable of delivery precisely controlled ablation, in desired spatial patterns using all electrodes or subsets of electrodes.

In some embodiments, a generator allows catheters to deliver very precise and specific ablation patterns in regular, irregular, and personalized shapes tailored to the specific rhythm disturbance in that patient. The ability to deliver AC with various power and frequencies through each element is attributable to the inventive process, the energy waveform approaches, and novel combinations of materials. These configurations enable ablation to be tailored to provide shallow or deep, wide or narrow fields of tissue modification or destruction while minimizing unwanted damage.

For simplicity, the disclosure is discussed in relation to the treatment of heart rhythm disorders, such as Atrial Fibrillation. Damage effects that can be minimized by this tailored approach include excessive heating of tissue causing char, excessive heating of blood causing coagulum (clot) or steam pops, excessive energy delivery to adnexal structures such as the esophagus when treating the posterior wall of the heart, the phrenic nerves when treating the pulmonary veins or atrial appendages, bronchi when treating the pulmonary veins, or coronary arteries when treating several locations within the heart.

However, the process applies to patients in whom critical regions for a biological rhythm disorder arise in regions of different sizes and thus with different needs for energy delivery. An example of this embodiment is to identify patients with atrial fibrillation (AF) who may or may not benefit from pulmonary vein isolation (PVI), and for whom ablation may need to identify and then treat gaps in ablation lines. The same is true for linear ablation lesions for atrial flutter or ventricular tachycardia. In other patients, the device may be used to treat critical regions (or sources), which could be sites other than the pulmonary veins (PV) in patients with atrial fibrillation, or elsewhere in the heart in other heart rhythm disorders.

The discussion may be generalized to cover other rhythm disorders arising from misaligned electrical signals in biological tissue, disorders of mechanical contraction, heart failure, abnormalities of the coronary blood vessels that supply the heart with blood, or nerve-related function ("the autonomic nervous system"). Other exemplary applications include electrical disorders of the brain including seizure disorders, diseases of gastro-intestinal rhythm such as irritable bowel syndrome, and bladder disease including detrusor instability. The process may also apply to chaotic disorders in these organs, such as atrial fibrillation in the heart or generalized seizures in the brain, as well as simple rhythm disorders. These examples are in no way designed to limit the scope of the disclosure for other conditions.

In some embodiments, the device can treat important regions based on their size or area, by optimizing the spatial configuration and type of energy delivery for said disorder in a particular patient. These considerations may dictate the choice of the paired catheter (probe) to optimize the size and configuration of electrodes for detection, and the configuration and pattern of ablation therapy delivery for therapy. For instance, small focused lesions may be needed if the treatment target is a gap in a line. Larger focused lesions may be required if the target is a localized source such as a driver of atrial fibrillation, atrial tachycardia, ventricular fibrillation or ventricular tachycardia, or other rhythms. Similarly, this logic applies to the source driving tonic/clonic seizures in the brain. This also applies to a focus that drives irritable bowel syndrome.

In some embodiments, the system has the ability to deliver optimized energy profiles designed for the current individual. Energy profiles could include radiofrequency energy at a low frequency of alternating current, or pulsed field energy at a lower frequency.

Definitions

In some embodiments, "biological signal" may refer to a signal produced by the body of a subject, and may reflect the state of one or more bodily systems. For instance, the heart rate reflects cardiac function, autonomic tone, and other factors.

In some embodiments, "biometric signals" may refer to signals that provide metrics of human characteristics. Biometric identifiers can be physiological or behavioral. Physiological biometrics include but are not limited to, DNA, fingerprints or palm prints, mouth swabs, tissue or urine samples, retinal images, facial recognition, the geometry of hands or feet, and recognition of the iris or odor/scent of an individual. Physiological biometrics may also include signals such as vital signs, the ECG, the EEG, EMG, and so on. Behavioral biometrics include patterns such as gait during walking or typing rhythm. Embodiments described in this disclosure may use dynamic patterns of combined physiological and behavioral biometrics over time, which adapt to changes in the individual and are thus robust to forgery from prior "versions" of a person's signature.

In some embodiments, "body" may refer to the physical structure of a human or an animal for veterinary work.

In some embodiments, "data streams" or "stream(s) of data" or "data" may refer to biological data sensed by one or more sensors that can provide real-time or near-real-time information on the biological process being sensed. Sensors in the heart may provide data comprising the electrocardiogram (ECG), Electrogram (EGM), pulse rate, pulse waveform, and cardiac hemodynamics. Other data may include cardiac acoustics, including analysis of heart sounds, and murmurs and sophisticated analyses of hemodynamics related to the heart. Lung function may be sensed as chest movement, auscultatory sounds, and nerve firing associated with breathing. Gastrointestinal disease may be sensed as sounds (borborygmi), movement on the abdominal wall, and electrical signals related to smooth muscle activity of the gut. Central and peripheral nervous system activity may be sensed as nerve activity on the scalp (electroencephalogram, EEG), remote from the scalp but still reflecting the EEG, and from peripheral nerve firing.

In some embodiments, "demographics" may refer to personal information which may include, but is not limited to, age, gender, family history of disease, ethnicity, and presence of comorbidities that may be clinically relevant.

In some embodiments, "digital classification" may refer to a partition of different states of disease or health based on mathematical indexes. Traditional disease classifications are qualitative, such as "atrial fibrillation is more common in the older individuals, those with heart comorbidities such as valvular lesions or heart failure, and those with metabolic syndrome". A digital classification translates this broad dataset into quantifiable primary and secondary data elements (data vectors). The likelihood that a disease entity $D_n$ is present in a specific individual is approximated by the probability $p(D_n)$:

$$p(D_n) = \sum_{i=1}^{m} \frac{(k_n p(V_{n,i}))}{k_n}$$

where m is the number of available data input types, n is the disease being considered, and $p(V_{n,i})$ is the probability that data vector $V_{n,i}$ contributes to disease n for input i, and $k_n$ is a weighting constant for disease n. These elements are integrated into the classification, which computes probabilities that a specific data input contributes to disease. Probabilities can be obtained from population data, in which the profile of a specific person is matched to the most similar individuals or profiles in that population. The probability can also be obtained from data in this individual alone, compared to times of health (self-reported or adjudicated) and times of disease (self-reported or adjudicated). These calculations can be performed by traditional estimating equations but may also be by statistical techniques and machine learning. A digital classification may represent a disease entity stochastically by the aggregate of abnormalities in multiple related data inputs. This process is dynamic since the equation reflecting disease will change when data is added, when data changes, and when the state of health or disease is updated. This is an approach to integrate massive amounts of data from traditional data sources as well as wearable devices in an individual, or massive amounts of data from several individuals as a crowd-sourced paradigm.

In some embodiments, "historical data" may refer to stored data, which may include reports from medical imaging, e.g., magnetic resonance imaging (MRI), computed tomography (CT), radiological, or other scans of an organ, data from genetic testing analyses (e.g., presence of one or more genomic variants), previously-obtained ECG reports, pathology, cytology, information on genomic variants (genetic abnormalities and non-disease causing variations), and other laboratory reports. This also includes clinical demographics such as age, gender, other conditions present in the individual, and a family history of diseases. Historical data may further include additional personal historical details that could be relevant to generating the personal digital record, for example, socioeconomic status including income strata, mental illness, employment in a high-stress profession, number of pregnancies (in women), engaging in high-risk behaviors such as smoking, drug or alcohol abuse, etc.

In some embodiments, "machine learning" may refer to a series of analytic methods and algorithms that can learn from and make predictions on data by building a model. Machine learning is classified as a branch of artificial intelligence that focuses on the development of computer programs that can automatically update and learn to produce predictions when exposed to data. In some embodiments, machine learning is one tool used to create the digital network and personal digital records linking sensed or recorded data with a specific output such as response to therapy, or ability to maintain normal rhythm. For applications in the brain, outputs could include the absence of seizure activity. Machine learning techniques include supervised learning, transfer learning, semi-supervised learning, unsupervised learning, or reinforcement learning. Several other classifications may exist.

In some embodiments, "reinforcement learning" may refer to a form of machine learning that focuses on how software agents take actions in a specific environment to maximize cumulative reward. Reinforcement learning is often used in game theory, operations research, swarm intelligence, and genetic algorithms and has other names such as approximate dynamic programming. One implementation in machine learning is via formulation as a Markov Decision Process (MDP). Reinforcement learning may differ from supervised machine learning in that it may not use matched inputs and labeled outputs, and actions that result in sub-optimal rewards are not explicitly corrected (unlike supervised learning which may correct suboptimal rewards via e.g., backpropagation algorithms in a perceptron).

In some embodiments, "semi-supervised machine learning" may refer to a process that combines techniques from supervised and unsupervised machine learning to address cases where a large amount of data is available but only a portion of the data is labeled. One approach is to impute or infer labels from similar data, based on a comparison of the data under consideration to other data within the database. Another approach is to generate labels for an unlabeled dataset based on the portion of data that is labeled. Yet another approach is to use training from a different problem or a different dataset to generate labels for these data. Such techniques are used to improve the learning accuracy of models by creating "pseudo labels" for the unknown labels (an approach known as transductive learning) and to improve model learning by adding more input to output examples (inductive learning).

In some embodiments, "supervised machine learning" may include methods of training models with training data that are associated with labels. Techniques in supervised machine learning may include methods that can classify a series of related or seemingly unrelated inputs into one or more output classes. Output labels are typically used to train the learning models to the desired output, such as favorable patient outcomes, accurate therapy delivery sites, and so on. Supervised learning may also include a technique known as 'transfer learning', where a pretrained machine-learned model trained on one set of inputs or tasks, is retrained or fine-tuned to predict outcomes on another input or task.

In some embodiments, "unsupervised machine learning" may include methods of training models with training data without the need for training labels. Techniques in unsupervised machine learning may include cluster analysis that may be used to identify internal links between data (regardless of whether data is labeled or unlabeled). In some embodiments, patterns (clusters) could be identified between clinical data (such as diagnosis of atrial fibrillation, or presence of heart failure, or other disease), family history, data from physical examinations (such as regularity of the pulse, low blood pressure), data from sensors (such as altered temperature, altered skin impedance), electrical data (atrial waveforms on the ECG), imaging data (enlarged left atrium or reduced), biomarkers, genetic and tissue data as available. Another technique is to use autoencoders, to featurize and compress input data. Autoencoders are sometimes described as 'self-supervised' since the model input and output are the same.

In some embodiments, a "medical device" may refer to an instrument, apparatus, implement, machine, contrivance, implant, in vitro reagent, or another similar or related article, including a component part, or accessory, which is intended for use in the diagnosis of disease or other conditions, or in the cure, mitigation, treatment, or prevention of disease, in man or other animals.

In some embodiments, "neural networks" may refer to a class of machine learning models that include interconnected nodes that can be used to recognize patterns. Neural networks can be deep or shallow neural networks, convolutional neural networks, recurrent neural networks (gated recurrent units, GRUs, or long short-term memory, LSTM, networks), generative adversarial networks, and auto-encoders neural networks. Artificial neural networks can be combined with heuristics, deterministic rules, and detailed databases.

In some embodiments, "population data" may refer to a determinant of the accuracy of a process. This is to create a digital classification of patients in the population. The classification may include some or all data elements in the personal digital record of the individual under consideration. Mathematical analyses are used to compare the personal digital record of the individual to the digital classification and calculate the best match. If the index individual is very different from the reference population then the digital classification may not adequately represent this individual. In this case, data may be derived primarily from that individual, using prior data at times of adjudicated health or adjudicated illness. If the reference population is broad but has other limitations, such as not having sufficient data points for an accurate digital classification, or not having well-labeled data, the classification may be less useful. In some embodiments, the ideal data set may include data that are well labeled and from a large number of individuals that represent the entire population, which can be grouped by desired outcome to create a digital classification.

In some embodiments, "sensors" include devices that can detect signals, such as biological signals from the body of an individual. A sensor may be in direct contact with the body or may be remote. Electromagnetic sensors can sense electromagnetic signals relating to the electromyogram (EMG), electroencephalogram (EEG), electrocardiogram (ECG), nerve firing, electromagnetic light (visible or invisible such as near-infrared or infrared), or other emitters. In some cases, the term "sensor", especially when describing certain cardiac applications in which electrical information is detected, may sometimes be used interchangeably with "electrode", "electrode catheter", "probe", "pole" or "catheter." Electrical sensors can detect impedance, such as conductance across tissue which may fall during ablation and then rise when a scar has formed. Impedance can also be measured across the skin when it falls in the presence of electrolyte solutions such as sweat, such as times of sympathetic nervous system predominance. Sensors can also detect other chemical changes via current flows.

Sensors may also detect temperatures, using a thermistor or other thermal detector. Sensors can detect light such as changes in the color of reflected or emitted light from heart activity (photoplethysmography), and changes in peripheral oxygenation (e.g., cyanosis, anemia, vasodilation on the skin).

Sensors can detect sound via a microphone. This can be used to sense sounds from the heart, lungs, or other organs. Sensors can detect contact force, pressure, or other vibrations or movement via piezoelectric elements. Sensors can detect chemicals directly, using specialized sensors for hormones, drugs, bacteria, and other elements that are typically transduced on the device to an electrical signal. Examples include motion sensing of chest wall movement from a breath or heartbeat, chest wall vibrations from certain types of breath (e.g., a loud obstructive breathing sound), or heart sound (e.g., a so-called "thrill" in the medical literature). Breath sensors can detect movement of the chest wall, abdomen, or other body parts associated with ventilation, acoustic data (sound) associated with breaths, or oxygenation associated with breathing. Chemical sensors can detect chemical signals on the skin or other membranes that reflect body chemistry such as oxygenation and deoxygenation, acidosis (pH), stress (catecholamines), glucose levels, certain drugs, or other states that will be familiar to those skilled in the biochemistry arts. Sensors can also detect images using a camera or lens requiring contact from the fingerprint or other body part, sense movement from specific muscles, or sense iris dilation or oscillations from photosensors in a contact lens. Positional sensors can identify positions of body parts and changes over time (including gait) or contact sensing of the position of certain body parts at one point in time or over time (e.g., a facial droop, a facial tick, or another idiosyncratic movement). In exemplary embodiments of the inventive system, multiple sensors may be used in communication with a central computing device or may form a network linked via BLUETOOTH, WI-FI, or other protocols to form an intranet or Internet of things (IoT) of biological sensors.

In some embodiments, "signal" may include electronic, electromagnetic, digital, or other information that can be sensed or acquired. Sensing signals are detected unaltered from their natural form (e.g., recorded) with no transformation. Sensing signals are typically biological signals. Sensing signals can be detected by humans (e.g., sound, visual, temperature) but also by machines such as microphones, auditory recorders, cameras, and thermometers. Acquired signals are detected in a transformed state, such as an ECG recording. Such signals may be biological, since cardiac bioelectricity generates the ECG, or non-biological signals, e.g., vibration sensed after application of sonic or ultrasonic energy, or a haptic signal transduced from a sensed electrical, sonic, or another signal. Signals may be sensed via physical contact with a sensor.

The following description and accompanying figures provide examples of applications of the inventive system and method for personalizing treatment by analyzing personal digital records of health and disease, to detect regions of interest for biological rhythm disorders and treat such regions of interest. The examples described herein are intended to be illustrative only. As will be evident to those of skill in the art, additional variations and combinations may be formed employing the inventive principles disclosed herein.

Treatment System

FIG. 1A illustrates a treatment system 100 for the operation of a treatment device 105, in accordance with some embodiments. The treatment system 100 includes the treatment device 105, the control system 110, a generator 115, an irrigation pump 120, and an input/output device 125. The various components of the treatment system 100 are connected via a network 130. Additional or fewer components may be implemented in the treatment system 100. For example, another non-invasive device comprising a wearable electrode array can be utilized in conjunction with the other components shown in FIG. 1A. Other embodiments incorporate an external sheath, which is first inserted into the patient and translocated to the treatment site, followed by the insertion of the treatment device 105 into the sheath.

The treatment device 105 is used for invasive access and ablation treatment of biological tissues 180. In various embodiments, the treatment device 105 may be referred to as a heart treatment device or ablation treatment device. The treatment device 105 may be used to treat a heart rhythm disorder by delivering ablation to certain locations of tissues 180 in a patient's heart. The treatment device 105 includes, among other components, a handle 146, a shaft 150, and a catheter 155. The handle 146 is where a physician or an automated control system controls the movement of the shaft 150 and the catheter 155. The handle 146 also includes interfaces for connection to other components in the treatment system 100, e.g., the generator 115, the irrigation pump 120, and the network 130. The shaft 150 is inserted into a patient via a vascular access point. The shaft 150 is directed to the tissue 180 requiring treatment. The catheter 155 is deployed from shaft 150, where the catheter 155 is configured to sense electrical signals for guidance of the catheter 155 and to deliver ablation energy to one or more source regions identified in the tissue 180. The various components of the treatment device 105 will be further described in the figures below.

While treatment of heart rhythm disorder is used as the primary example in this disclosure, in some embodiments, the treatment system 100 may be used to deliver ablation to other types of biological tissues.

The control system 110 controls the various components of the treatment system 100. The control system 110 is configured to receive data from various components and provide instructions to various components. For example, the control system 110 can receive electrical signals sensed by the treatment device 105 in the heart. In several preferred embodiments, the control system 110 may process and analyze sensed electrical signals to determine how to guide and place the device 105 within biological organs. The control system 110 may provide guidance controls for the movement of a catheter 155 in contact with a biological organ such as a heart. The control system 110 will determine an optimal procedure to modify tissue 180 using energy generated by the generator 115, which could be in the heart, muscle, nerve, or other tissue. The control system 110 can provide instructions to the generator 115 to specify the ablation procedure, the irrigation pump 120 to specify irrigation parameters, and the treatment device 105. The control system 110 will receive inputs from each of these systems, such as the treatment device 105 to enable a controlled-loop-system in which energy delivery is controlled, titrated, or maintained within a desired range. The control system 110 may also receive inputs from a user, e.g., a physician, to aid in the treatment procedure. The control system 110 may also provide real-time data and/or updates to the input/output device 125 for displaying such data and/or updates during the treatment procedure.

While the control system 110 is depicted in FIG. 1A is a remote control system that communicates with the rest of the components in the treatment system 100 through the network 130, in various embodiments the control system 110 may take different forms. For example, in some embodiments, the control system 110 may be a local computing device that is located in the surgery room with the rest of the components in the treatment system 100. In some embodiments, part or the entirety of the control system 110 may be part of the generator 115, such as in a configuration where the control system 110 is included in a processing unit of the generator 115. In some embodiments, the control system 110 may include two or more devices, such as a local computing device and a cloud server. The local computing device may provide various control algorithms and the cloud server may provide additional computation and data analysis features.

The generator 115 provides electrical energy to the treatment device 105 for performing a treatment that modifies biological tissues 180, e.g., by ablation. an ablation procedure. The generator 115 may include an energy source 135 and an interposer 140. The energy source 135 generates the electrical energy for use in the ablation procedure. The energy source 135 may in turn fetch the electrical energy from another energy source (e.g., an electrical outlet, an electricity generator, a battery, etc.) for conversion into electrical energy for use in the ablation procedure. For example, the ablation procedure requires a particular energy frequency, a particular waveform, a particular duration, other ablation procedure parameters, etc. The generator 115 may include driver circuits that regulate electrical energy at the appropriate frequency, with the appropriate waveform, and for the appropriate duration. The interposer 140 electrically connects the energy source 135 to the electrode array on the catheter 155. The interposer 140 may control the connection to each electrode of the electrode array. For example, if the ablation procedure requires the actuation of a subset of the electrodes in the electrode array, then the interposer 140 may switch off connections for the remaining electrodes not required during the ablation procedure. As another example, the interposer 140 may control which mode each electrode is operating in. In some embodiments, the electrode array of the catheter 155 is advantageous in that each electrode may be used for sensing and ablation. The interposer 140 may utilize switches connected to each electrode, for switching the electrode between a sensing mode, an ablation mode, and an off mode (e.g., the electrode being connected to an electrical ground).

In some embodiments, the generator 115 may operate in a closed-loop-sensor form in which the control system 110 is part of the generator 115. For example, the control system 110 may be implemented as firmware of a controller (e.g., a processor such as a microcontroller, a microprocessor, etc.) of the generator 115. Signals sensed from the treatment device 105 are processed by the controller, which regulates the energy generated by the generator 115. The controller is in communication with the sensing elements 160 and the treatment elements 162. In some embodiments, as it will be disclosed further in detail, the generator 115 is capable of working with types of catheters 155 in which one or more sensing elements 160 are physically the same as the ablating elements 162.

The catheter 155 is the component that is placed close to the biological tissue 180 to conduct ablation by delivering ablation energy to alter the tissue 180 and treat a heart rhythm disorder. The ablation energy may be in the form of heat, voltage, radiofrequency, laser, microwave, ultrasound, cryoablation, or any combination of the above, or any other form(s) of energy which can be configured to create precisely controlled localized tissue damage. In some embodiments, the treatment is caused by pulsed field ablation. In some embodiments, the magnitude and duration of energy are delivered with a range consistent with pulsed filed ablation. In some embodiments, the treatment is caused by radiofrequency ablation. In some embodiments, the magnitude and duration of energy are delivered with a range consistent with radiofrequency ablation. The catheter 155 includes electrodes that may carry one or more treatment elements 162 and one or more sensing elements 160. The treatment elements 162 are used to carry and deliver the ablation energy to the tissue 180. The sensing elements 160 are used to detect appropriate signals to provide feedback to the generator 115 and/or the control system 110. In some embodiments, the catheter 155 has an array of sensing elements 160 and an array of treatment elements 162 that are arranged in a two-dimensional grid.

In various embodiments, the catheter 155 can be in any suitable design, shape, and arrangement of sensing elements 160 and treatment elements 162. Examples of some designs of the catheter 155 are discussed in subsequent figures. US Patent Application Publication 2023/0049942, entitled "Treatment System with Sensing and Ablation Catheter for Treatment of Heart Rhythm Disorders," describes further examples of designs and element arrangements in catheters. The publication is incorporated by reference herein for all purposes.

Sensing elements 160 are used to detect one or more types of signals to provide feedback for the treatment system 100 and may detect signals to identify directionality 170 of the source of the tissue 180 that may cause rhythm disorder. The type of signals that are detected by the sensing elements 160 may depend on the design of the catheter 155 in various embodiments. In some embodiments, the sensing elements 160 may include different types of sensors, such as temperature sensors, electrical signal sensors, force sensors, image sensors, infrared sensors, or any combinations of the above. Depending on the type of sensor, a sensing element 160 can be an electronic sensor or a structure that allows the detection of a signal. For example, in some embodiments, a sensing element 160 can be a piezoelectric sensor, a capacitive sensor, a magnetic force sensor, an optic sensor, or another suitable electronic sensor. In some embodiments, a sensing element 160 can be a mechanical structure, such as a junction of two metals to create a thermocouple to detect temperature. In some embodiments, a sensing element 160 may also be an exposed metallic surface that is used to detect electrical signals.

In some embodiments, a sensing element 160 is an electrical signal sensing element and is capable of sensing electrical signals of the biological tissue 180. Examples of electrical signals that are sensed by the sensing elements 160 may be current, voltage, impedance, or another suitable electrical signal that can be in a simple or complex form. The measurement may be in amplitude or in amplitude, frequency, and/or phase. In some embodiments, the same type of sensing elements 160 may serve multiple purposes. For example, an electrical signal sensing element 160 may be used to detect electrical signals (e.g., voltage or current) that are coming from a tissue source of a rhythm. An arrangement of electrical signal sensing elements 160 may be used to detect a gradient or distribution of electrical signals and changes for the determination of directionality 170 towards a source of abnormal rhythm. The same electrical signal reading may be used to determine the temperatures of the electrodes individually based on thermocouples so that each electrode's temperature may be determined and monitored individually.

Treating elements 162 are capable of delivering energy to modify the tissue, such as by ablation. A treatment element 162 may be referred to as an ablation element. A treatment element 162 may be a part of an electrode that is formed from a conductive wire. Example materials for a treatment element 162 include but are not limited to, copper, gold, platinum, metal alloys containing gold, metal alloys containing platinum, gold-plated copper, other conductive metals, other conductive metal alloys, etc. For simplicity, unless specifically stated otherwise, in this disclosure metals include alloys, and vice versa. In one or more embodiments, the electrode material is safe for use in blood. For example, the size of each electrode in FIG. 1A is on the order of <1 mm. This small electrode sizing provides for high-resolution sensing since the size of the measurement device limits the measurement resolution.

The catheter 155 may include a plurality of electrodes 164. Electrodes 164 may also be referred to as probes. Some of the electrodes 164 may take the form of exposed metallic or conductive parts of the catheter 155. An electrode 164 can be a sensing electrode that includes a sensing element 160, a treatment electrode that includes a treatment element 162, or a combined electrode that includes both a sensing element 160 and a treatment element 162 to simultaneously perform treatment and detect signals. For example, in some embodiments, an electrode 164 may include a junction of a first conductive wire and a second wire. The first conductive wire may be formed of a first conductive material and the second wire may be formed of a material that is different from the first material. The treatment element 162 may include the first conductive wire and is configured to deliver the ablation energy to the biological tissue. The sensing element 160 may be a temperature sensor that includes the junction of the first conductive wire and the second wire such that a thermocouple between the first conductive wire and the second wire is formed at the junction to measure temperature at the electrode.

In some embodiments, the generator 115 includes circuitry and design to individually regulate the ablation energy delivered to each electrode 164 of a plurality of electrodes 164 in the catheter 155 and also to individually measure signals of sensing elements 160 in each electrode 164. In some embodiment, the temperature of each electrode 164 can be measured individually and the generator 115 may regulate the ablation energy delivered to each electrode 164 based on the individual temperature reading. In some embodiments, each electrode 164 is capable of delivering a different ablation energy level. In some embodiments, the electrodes 164 are grouped by subsets and operate collectively or in compensation with each other within a subset and between two subsets. In some embodiments, the electrodes 164 may form an array and may be arranged in a specific spatial manner (e.g., 2×2, 4×4, 6×6, 8×8, 4×6, a radial arrangement, a circular arrangement, etc.) so that the electrical signal gradient or change may be measured across the electrodes 164 in an array. The electrical signals may be input to a signal processing model in the control system 110, such as a machine learning model, to determine the directionality 170 of a source.

As such, in some embodiments, an electrode may serve any one or more of the following functions simultaneously. For example, an electrode may serve as an ablation element to deliver ablation energy. In some embodiments, the amount of ablation energy carried by an individual electrode can be regulated individually by the generator 115. In some embodiments, the electrode, which includes a junction of two materials, may also serve as a temperature sensor by thermocouple. In some embodiments, each electrode's voltage or current at the conductive wire may be measured and the collection of an array of electrodes may create a directionality guidance 170 to determine a source of rhythm disorder.

Coupled with each sensing or treatment element are one or more conductor wires that transfer signals from the handle 146 to and from each element. The wires connected to electrode 164 may be substantially large in diameter to transfer the required ablation energy from generator 115 to electrode 164. This may include the ablation energy required for pulsed-field ablation or other high-energy applications. In one or more embodiments, the conductive wires are formed from copper. Other example wire materials include gold, platinum, silver, other conductive metals, other conductive metal alloys, etc. The wires may be insulated to prevent unwanted discharge of electrical energy that could cause damage to tissue not being treated or damage to the components of the heart treatment device 105.

In a sensing configuration, an electrode 164 can be configured to measure electrical signals for the control system 110. The electrical signals collected by each electrode can include a voltage signal, a current signal, an impedance signal, complex impedance on AC signals, and other parameters. The spacing between elements is a function of the sensing catheter 155 and should be sufficiently small to provide high-resolution sensing of the biological tissue. In one or more embodiments the junction between two wires of dissimilar conductors forms a natural thermocouple, and electrical signals sensed at the junction indicate temperature.

In one or more embodiments, one or more dedicated temperature sensors may be implemented on the catheter 155. The temperature sensors measure the temperature of tissue in contact with the temperature sensors. Temperature sensors can be near multiple electrodes, on each spline, or in other configurations. In one or more embodiments, sensors measure a change in electrical resistance, electrical voltage, or another electrical metric within a circuitry having a temperature-sensitive material. Examples of temperature sensors include a resistance temperature detector, a thermocouple, a thermistor, etc. In other embodiments, non-contact temperature sensors may be used, e.g., infrared photoelectric sensors.

In an ablation configuration, an electrode 164 is configured to deliver energy to tissue. The ablation energy is in the form of electrical energy received from the generator 115. The ablation energy may be tailored, e.g., at a particular frequency or wavelength, with a particular waveform, over a particular duration. Examples of ablation energy include common moderate power, moderate duration energy such as 3-5 Watts at 15-60 seconds, as well as high power short duration energy such as 5-10 Watts at 5-15 seconds. Examples of ablation energy may also include very high powers associated with pulsed-field ablation (to cause irreversible electroporation) with a short duration. Each electrode 164, in the ablation configuration, is capable of achieving sufficient depth of delivery of tissue ablation to modify or destroy tissue harboring biological disease. Tissue ablation is typically >1-2 mm for thin regions of the atrium, >2-5 mm for thicker regions of the atrium, >2-3 mm for the pulmonary veins, 5-10 mm for regions such as the tricuspid or mitral isthmus, or >10 mm for ventricular tissue. In some embodiments, each electrode's ablation energy is addressable independently. The array of treatment element 162 is capable of delivering ablation in a variety of patterns tailored to the actual tissue harboring each critical region for the biological disorder. This is advantageous as the catheter 155 need not perform multiple applications to ablate in a particular pattern, which would otherwise be the case.

The irrigation pump 120 controls the pumping of the irrigant to the heat treatment device 105. The irrigation lumens in the treatment device 105 and catheter 155 provide channels for the transmission of irrigant fluid between the handle 146 and the catheter 155. The irrigation lumens may be formed from rigid or compliant materials. At the proximal end of shaft 150 (towards where it connects to the handle 146), irrigation lumens may include one main irrigation lumen which attaches to the irrigation pump 120. The pump 120 may include various vessels and fluid channels for directing stored irrigant to the heart treatment device 105. The types of irrigants that may be used include: a chemical buffer or a saline infusate.

The irrigation pump 120 controls the pumping of irrigant to the treatment device 105. The irrigation pump 120 may include various vessels and fluid channels for directing stored irrigant to the treatment device 105. The types of irrigants that may be used include: a chemical buffer or a saline infusate. Delivery of irrigant during an ablation procedure prevents overheating of the heart tissue and the catheter 155, which avoids scarring of the heart tissue and potential damage to the catheter 155. Prevention of overheating also allows for deeper energy delivery without needing to prematurely stop the ablation procedure, providing greater efficacy in the ablation procedure.

The input/output device 125 is configured to display visual data to a user of the treatment device 105, e.g., a physician. The input/output device 125 may be a touch display capable of receiving user inputs. In such embodiments, the input/output device 125 may present a graphical user interface that a user is capable of interacting with. The user can provide inputs to the control system 110, e.g., inputs for adjusting the operation of the various components. Example controls include steering the treatment device 105 whilst in the patient, deploying and/or retracting the catheter of the treatment device 105 whilst in the patient, controlling the start of an ablation procedure, toggling parameters for the generator 115, toggling parameters of the irrigation pump 120, among other operations described herein this disclosure. The input/output device 125 can provide a real-time mapping of the patient's heart biosignals as sensed by the electrode array of the treatment device 105. Upon identification of one or more source regions, the control system 110 may alert the physician via the input/output device 125. The input/output device 125 may provide further updates during treatment, e.g., during the ablation procedure.

Data store 118 may be used to store any data used in the treatment system 100 including patient data, sensor data, treatment data, directionality data, and other suitable data. The data store 118 includes one or more storage units such as memory that takes the form of a non-transitory and non-volatile computer storage medium to store various data. The computer-readable storage medium is a medium that does not include a transitory medium such as a propagating signal or a carrier wave. The data store 118 may be used by the control system 110 or generator 115 to store data related to the treatment system 100. In one embodiment, the data store 118 communicates with other components by the network 130. This type of data store 118 may be referred to as a cloud storage server. Examples of cloud storage service providers may include AMAZON AWS, DROPBOX, RACKSPACE CLOUD FILES, AZURE, GOOGLE CLOUD STORAGE, etc. In another embodiment, instead of a cloud storage server, the data store 118 is a storage device that is controlled and connected to the control system 110. For example, the data store 118 may take the form of memory (e.g., hard drives, flash memory, discs, ROMs, etc.) used by the control system 110 such as storage devices in a storage server room that is operated by the control system 110.

The network 130 provides connections to the components of the treatment system 100 through one or more sub-networks, which may include any combination of local area and/or wide area networks, using both wired and/or wireless communication systems. In some embodiments, a network 130 uses standard communications technologies and/or protocols. For example, a network 130 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 130 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 130 may be represented using any suitable format, such as hypertext markup language (HTML), extensible markup language (XML), or JSON. In some embodiments, all or some of the communication links of a network 130 may be encrypted using any suitable technique or techniques such as secure sockets layer (SSL), transport layer security (TLS), virtual private networks (VPNs), Internet Protocol security (IPsec), etc. The network 130 also includes links and packet-switching networks such as the Internet.

Catheter Measurement

Figure 1B:
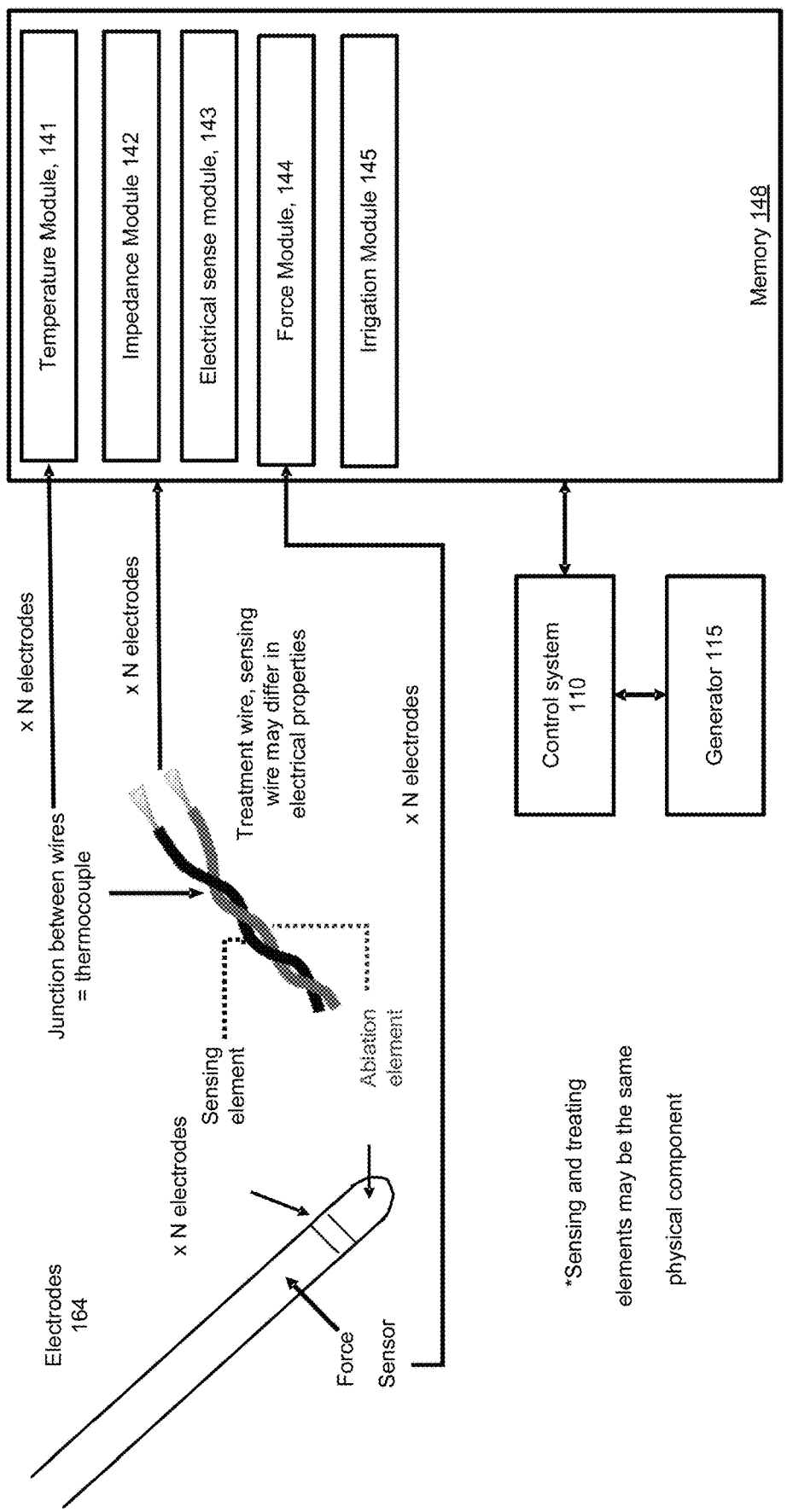
FIG. 1B is a conceptual diagram illustrating measurements of a catheter that can be used to control the ablation procedure, in accordance with some embodiments.

FIG. 1B is a conceptual diagram illustrating measurements of a catheter 155 that can be used to control the ablation procedure, in accordance with some embodiments. The control system may include several modules described below and memory 148 that stores code instructions, when executed, cause one or processors to enable various control functions.

The control system 110 may include one or more modules to process various signals. While several examples of modules are discussed in FIG. 1B, in various embodiments a treatment system 100 may include fewer, different, or additional modules. Temperature signals are sensed by a temperature module 141 associated with the control system 110. Impedance is processed in the impedance module 142. Electrical amplitude and other electrical signal parameters are processed in electrical sense module 143. Force sensing is processed by the force sensing module 144. The irrigation module 145 determines whether to increase or decrease the flow rate of irrigant based on sensed signals, e.g., high temperature would direct higher irrigant flow, by sending control signals to the irrigation pump 120 illustrated in FIG. 1A.

In some embodiments, the control system 110 is designed to deliver power in a precisely controlled feedback loop that more simply, rapidly, and accurately senses, processes, and delivers energy. In some embodiments, a catheter 155 is designed with a simplified configuration of sensing wires. In some embodiments, a wire that forms the sensing element and the current-delivery conducting wire are made of dissimilar metals, so that the junction of the two wires forms a natural thermocouple. In some embodiments, sensing electrical signals at this junction indicates temperature. This allows for coincidental sensing and energy delivery, which eliminates the need for a dedicated thermal sensor component and a separate wire. This design is of benefit in embodiments in which space or simplicity is important, particularly for a surgical device. The combination of sensing element 160 and treatment element 162 as the same physical components reduces the number of components and wires in a confined space of catheter 155.

Another advantage of coincidental sensing and energy delivery is that signal sensing is performed directly from the site of energy delivery in tissue. Such an arrangement improves the accuracy of control system 110 processing. For instance, if the sensed signal is temperature, the control system 110 can modify ablation energy from the generator 115 to keep the temperature at the tissue 180 within a desired range more accurately than if the temperature sensor were even a few millimeters away. This can minimize problems such as tissue overheating that may cause char, blood overheating that may cause clots or steam pops, or tissue underheating which may result in inadequate ablation.

While using a junction of two metallic wires to create a thermocouple is used as an example of coincidental sensing and energy delivery, other ways to detect temperature and deliver energy at the same electrode 164 are possible in various embodiments. For example, an electrode 164 may include a conductive wire for energy delivery and a temperature sensor such as an electronic temperature sensor located within 1 mm of the treatment element 162 to detect temperature.

In some embodiments, one or more force-sensing elements may be implemented on the catheter 155. The force-sensing elements measure the contact force between the catheter 155 and the tissue. The measured contact force can be used to verify contact between the catheter 155 and the tissue during sensing and/or ablation. The force-sensing elements may be piezoelectric sensors, surface capacitance sensors, etc.

In some embodiments, one or more photoelectric sensors may be implemented on the catheter 155. The photoelectric sensors may be used to identify changes to tissue composition prior to, during, or after ablation. The photoelectric sensors may also be infrared sensors that determine the temperature of the tissue.

An impedance module 142 may be used to measure impedance as a metric corresponding to the effectiveness of tissue ablation. For example, a low impedance during energy delivery may indicate effective tissue ablation, while a sudden rise in impedance may indicate poor contact with tissue. A measurement drop of sensing electrical amplitude in electrical sense module 143 in electrical amplitude in parallel with a fall in impedance during energy delivery may further indicate effective ablation, while a sudden drop in electrical amplitude with an increase in impedance may indicate poor tissue contact. Similarly low sensed force in sensing module 144 may indicate loss of contact. A catheter 155 may include one or more electrical sensors and force sensors. The control system 110 may use one or more types of signals, such as force, voltage, impedance, and current, individually or in combination with other types of signals, to determine whether the catheter 155 is in satisfactory contact with a target tissue. The control system 110 may provide visual indications or alerts to the physician operating the treatment device 105 regarding the contact measurement.

Heart Treatment Device

As illustrated in FIG. 1A, an example treatment device 105 may include a handle 146, a shaft 150, and a catheter 155, though there can be different components in some embodiments. Prior to insertion into the patient, the catheter 155 is sheathed within a sheath, e.g., that may be a separate component. The shaft 150 (e.g., sheathed within the sheath) is inserted into the patient and directed to the heart tissue with the catheter 155 in a compact state. Upon reaching the heart tissue, catheter 155 is unsheathed from the sheath, transitioning from the compact state to an expanded state that is shown in FIG. 1A. In the expanded state, the catheter 155 can be moved by steering of the shaft 150. The handle 146 provides the ability to (1) control the transitioning of the catheter 155 between the compact state and the expanded state and (2) control the movement of the catheter 155.

Figure 2:
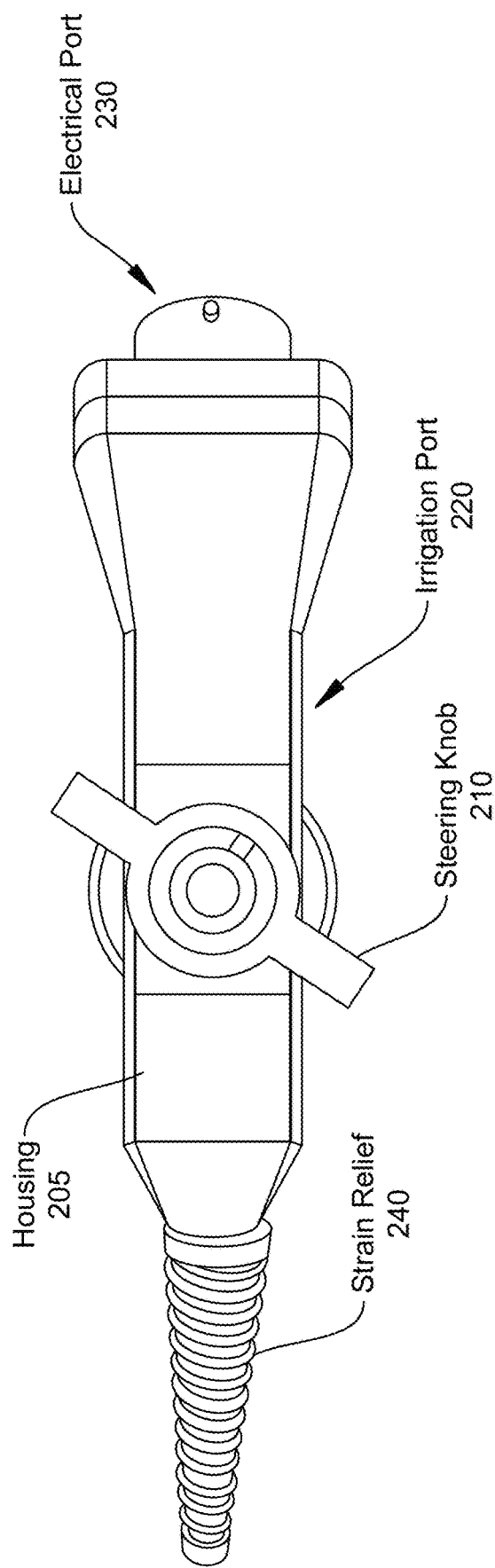
FIG. 2 illustrates a side view of a first handle of a treatment device, in accordance with some embodiments.

FIG. 2 illustrates a side view of the first handle 200 of the treatment device 105, in accordance with some embodiments. The handle 200 comprises a housing 205, a steering knob 210, an irrigation port 220, an electrical port 230, and a strain relief 240. The handle 200 may comprise additional, fewer, or different components than those listed herein.

The housing 205 is a rigid body with an interior chamber. The housing 205 may be sized and shaped to be held by a human hand. The housing 205 may be composed of a substantially rigid material, e.g., thermoplastics. Housing 205 may be substantially non-conductive. Housing 205 has an interior chamber for routing of irrigation fluid channels and wiring for catheter 155.

The steering knob 210 controls the movement of the catheter 155. The steering knob 210, as shown in FIG. 2, is a dial that can be rotated about an axis that is perpendicular to the plane of the paper. The steering knob 210 may be attached to one or more steering wires, such that rotation of the steering knob 210 creates tension on the steering wires. The tension created in the steering wires affects the movement of the catheter 155. In one embodiment, the steering knob 210 comprises a pair of steering wires. Rotation of the steering knob 210 clockwise from a neutral position creates tension in one steering wire which induces a curvature in the shaft 150 bending the catheter 155 towards the handle 200 in the first direction. Rotation of the steering knob 210 counterclockwise from the neutral position creates tension in the second steering wire which, consequently, induces a curvature in the shaft 150 bending the catheter 155 towards the handle 146 in a second direction, which is opposite the first direction. Other mechanisms for creating tension in the steering wires may be implemented in conjunction with or in the substation of the steering knob 210, e.g., a button with three positions (left, neutral, and right) can be used to create tension in a left string causing the catheter 155 to bend towards the left or in a right string causing the catheter 155 to bend towards the right. Typically, the sheath remains relatively fixed within the blood vessel (femoral vein or femoral artery), pericardial space, or other tissue plane, although some sheath movement is also provided. The catheter is sheathed and unsheathed by manual withdrawal and advancement from the handle-side of the catheter by the physician. In some embodiments, this can be achieved by motorized assistance or by entirely robotic control. The steering knob or steering controller can take on other designs as well, including a knob having a different shape or including one or more buttons or sliders, a joystick, or other video game-type controller, among other designs. In one or more embodiments, a motor assembly may be implemented in the handle for controlling the movement of the catheter.

The irrigation port 220 provides a connection of an irrigant fluid channel from the irrigation pump 120 to the irrigant fluid channel within housing 205. The irrigant fluid channel within housing 205 and routed to catheter 155 also connects to irrigation port 220. Irrigant that is pumped from the irrigation pump 120 flows through the fluid channel, through the irrigation port 220, and into the fluid channel routed to the catheter 155, where irrigant can be dispensed by the catheter 155, e.g., during an ablation procedure.

The electrical port 230 provides a connection between the electrical wiring from generator 115 and the electrical wiring within housing 205. Electrical energy that is provided by generator 115 is directed, at the electrical port 230, into the plurality of electrical wires in housing 205 that are connected to the electrode array of the catheter 155.

The strain relief 240 provides relief from strain and other stress on the shaft 150. The strain relief 240 is an elastic portion that absorbs strain and other stresses by focusing on the transition between the flexible shaft (150) and the rigid handle (146) which could lead to the kinking of the shaft in this location. In one or more embodiments, the strain relief 240 comprises a spring that surrounds the shaft 150 and may further include a protective rubber coating. Other designs for the strain relief 240 may be implemented such as a wire mesh. The strain relief 240 acts to dissipate strain in the shaft 150 along the length of this strain relief 240 that would otherwise be focused locally at the point of transition to the handle. FIG. 2 provides one example, but the strain relief 240 can take on other shapes and designs than what is shown in FIG. 2.

Figure 3A:
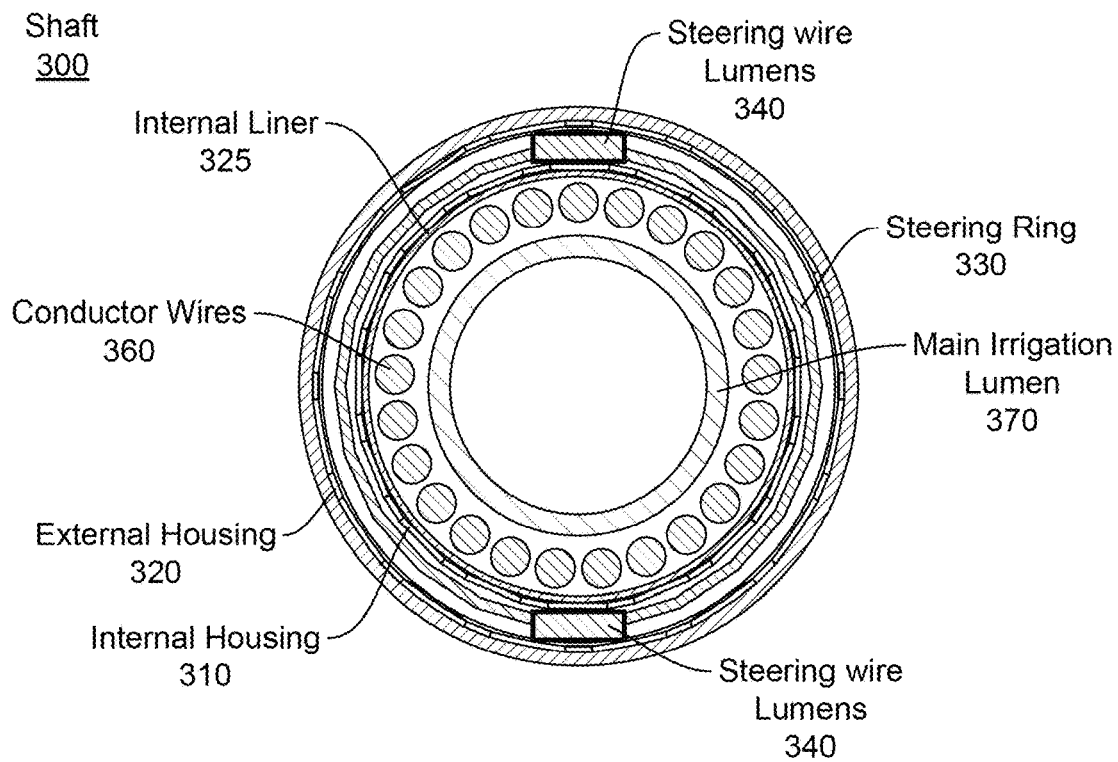
FIGS. 3A & 3B are cross-sectional views of a shaft of the treatment device, in accordance with some embodiments.
Figure 3B:
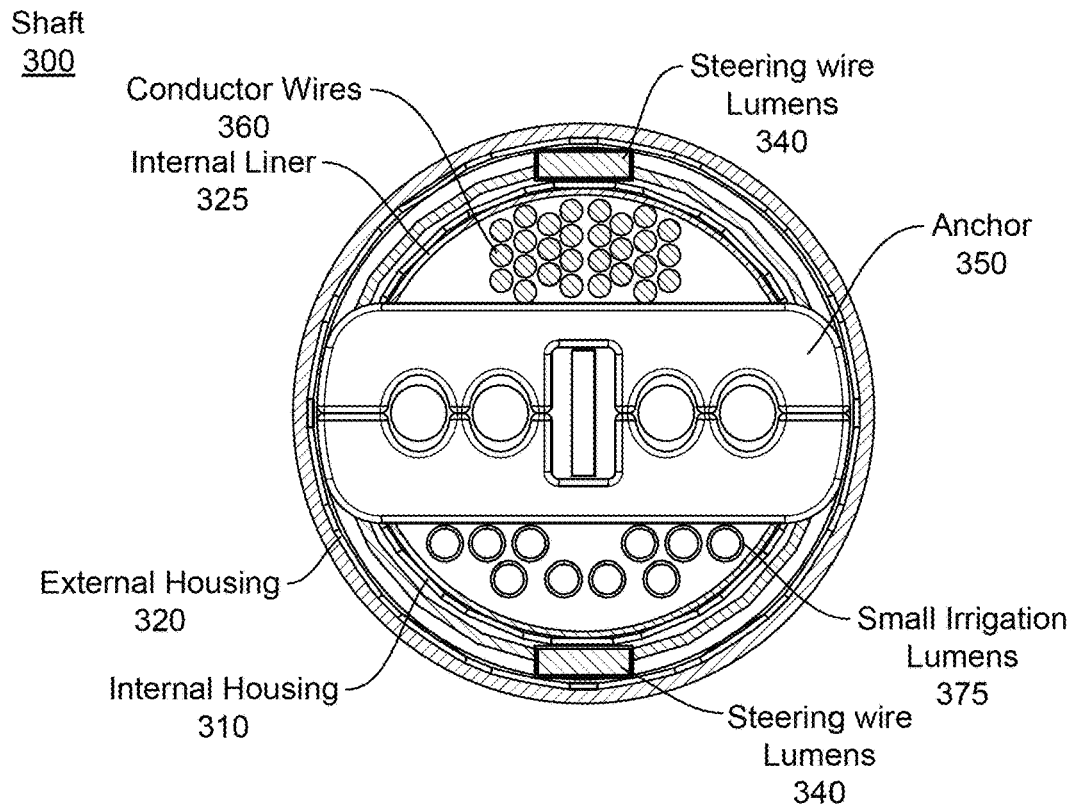
Figure 3C:
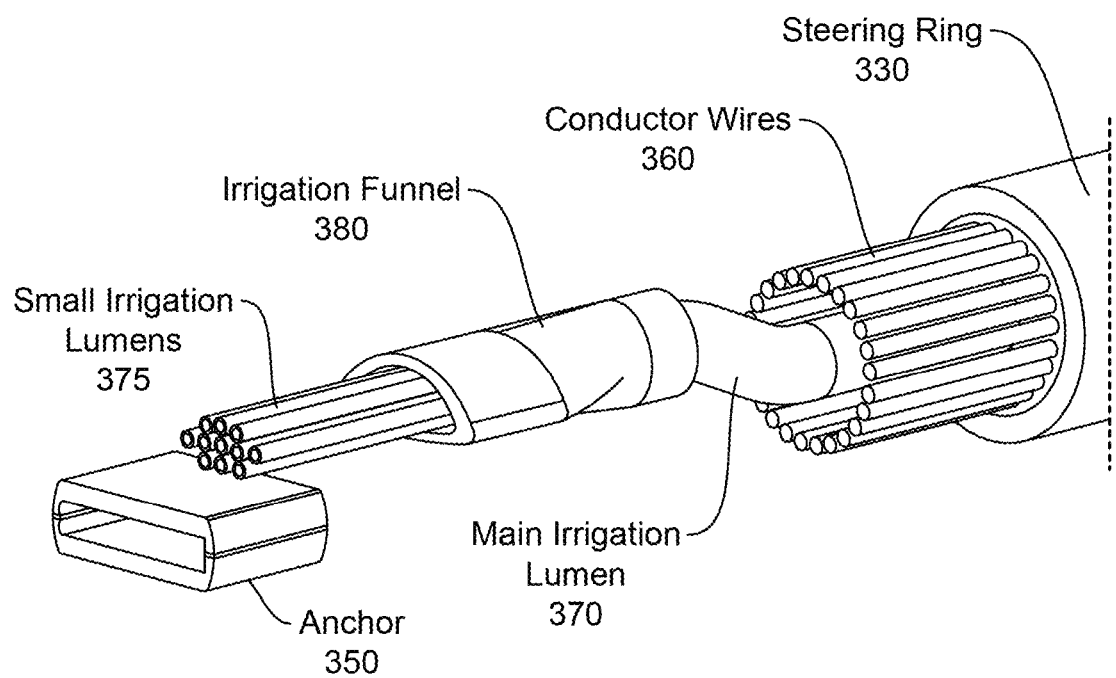
FIG. 3C illustrates a cutaway perspective view of a distal portion of the shaft, in accordance with some embodiments.

FIGS. 3A & 3B are cross-sectional views of shaft 300 of the treatment device 105, in accordance with some embodiments. The shaft 300 is an example of shaft 150 illustrated in FIG. 1A. FIG. 3A illustrates a proximal cross-section view of shaft 300 of the treatment device 105, in accordance with some embodiments. FIG. 3B illustrates a distal cross-section view of shaft 300, in accordance with some embodiments. FIG. 3C illustrates a cutaway perspective view of a distal portion of the shaft 300, in accordance with some embodiments.

The shaft 300 is a strong and flexible cylinder that extends from the handle 146 to the catheter 155. The shaft 300 has a length to ensure that the catheter 155 can be inserted at an access point of the patient and reach the heart tissue to be treated. The shaft 300 comprises, among other components, an internal housing 310, an external housing 320, an internal liner 325, a steering ring 330, steering wire lumens 340, an anchor 350, conductor wires 360, and irrigation lumens. As shown in FIG. 3A, the shaft 300 is generally shaped as a cylinder forming a cavity, through which other components may be passed through, e.g., wiring and irrigation lumens that connect to the catheter 155. However, the shaft 300 can take on other designs as well, including having a square-shaped cross-section, a different length, having a different arrangement of the components shown in FIGS. 3A & 3B (e.g., fewer or more steering wire lumens 340 or differently positioned steering wire lumens 340).

The internal housing 310 and the external housing 320 form the structural support for the shaft 150. The internal housing 310 and the external housing 320 may be formed from a sufficiently strong yet flexible material, e.g., a metal, a metal alloy, etc. Disposed radially between the internal housing 310 and the external housing 320 is the steering ring 330. A coating layer may be coupled to the steering ring 330 to ensure no metal is exposed to the body.

On the internal surface of the internal housing, 310 is an internal liner 325. The internal liner 325 may be sufficiently waterproof to prevent liquids from entering the cavity within the internal housing 310. An example material for the internal liner 325 may be polytetrafluoroethylene (PTFE) which is a synthetic fluoropolymer with hydrophobic properties.

The steering wire lumens 340 provides a cavity for steering wires to be disposed on. The steering wires are connected to the steering ring 330 at a distal end of the shaft 150, i.e., in proximity to the catheter 155. When one steering wire is pulled, the pull ring is pulled to bend the shaft 150 towards the side with the pulled steering wire.

FIG. 3B illustrates a distal cross-section view showing an anchor 350. The anchor 350 couples to one or more of the other components in the shaft 300, e.g., the internal housing 310, the external housing 320, some other component, etc. The anchor 350 serves as a structural anchor for the attachment of the catheter 155 to shaft 300. Various anchors 350 may be implemented with the catheter 155, the design may not necessarily have an anchor, or the design may have a structure other than an anchor to perform a similar function.

The conductor wires 360 are conductive and configured to transmit electrical energy between the electrode array of the catheter 155 and the handle 146. The conductor wires 360 are formed of conductive materials, e.g., copper, gold, platinum, other conductive metals, other conductive metal alloys, etc. In the embodiments shown in FIGS. 3A & 3B, the conductor wires 360 are disposed radially around the irrigation lumens at a proximal end of the shaft (FIG. 3A) and transition to being disposed on one side of the anchor 350 (FIG. 3B).

The irrigation lumens form a channel for the transmission of irrigant fluid between the handle 146 and the catheter 155. The irrigation lumens may be formed from rigid or compliant materials. At the proximal end of shaft 300 (towards where shaft 300 connects to the handle 146), the irrigation lumens may include one main irrigation lumen 370 which then splits into small irrigation lumens 375 at a distal point along the shaft 300, e.g., towards the catheter 155.

FIG. 3C illustrates a cutaway view of the transition between the main irrigation lumen 370 to the small irrigation lumens 375. In the embodiment shown, shaft 300 further comprises an irrigation funnel 380 that connects a distal end of the main irrigation lumen 370 to the proximal ends of the small irrigation lumens 385. The small irrigation lumens 375 connect to the catheter 155, e.g., to one or more irrigation pores disposed on the catheter 155. The irrigation funnel 380 is formed of a rigid material and includes one or more funneling channels that can split irrigant fluid provided from the main irrigation lumen 370 into the small irrigation lumens 375. The irrigation funnel 380 may also serve as a structural anchor to hold the irrigation lumens in place within shaft 150.

Figure 3D:
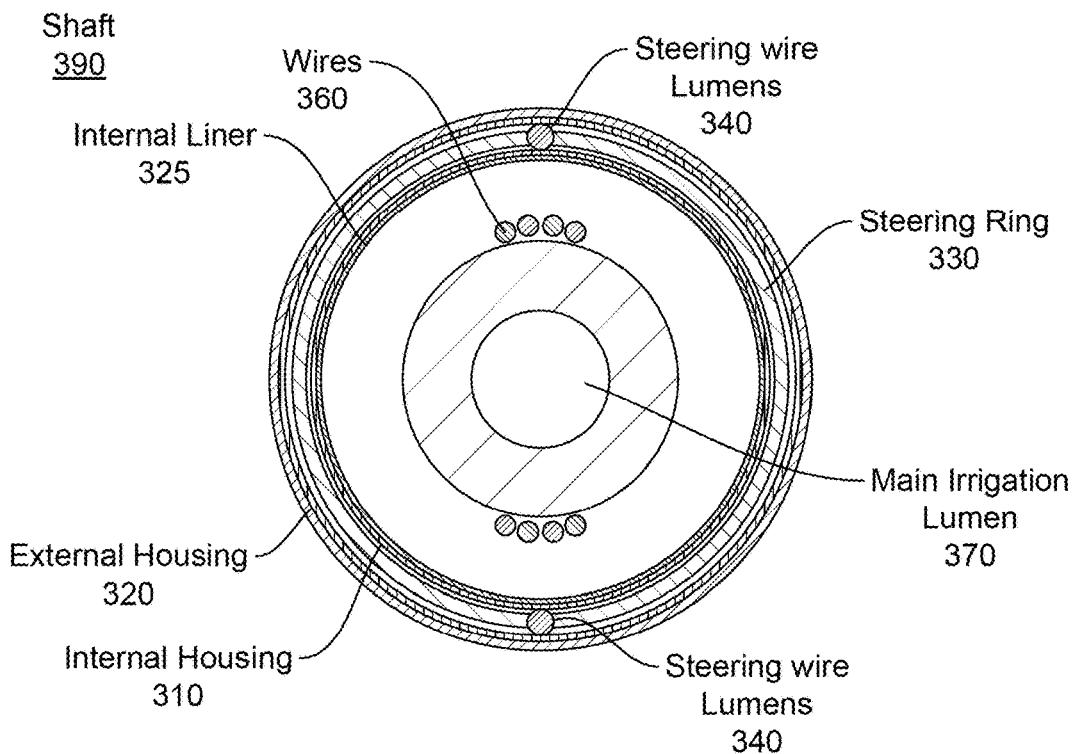
FIGS. 3D & 3E illustrate cross-section views of a shaft 390 that may be implemented in the treatment device, in accordance with some embodiments.
Figure 3E:
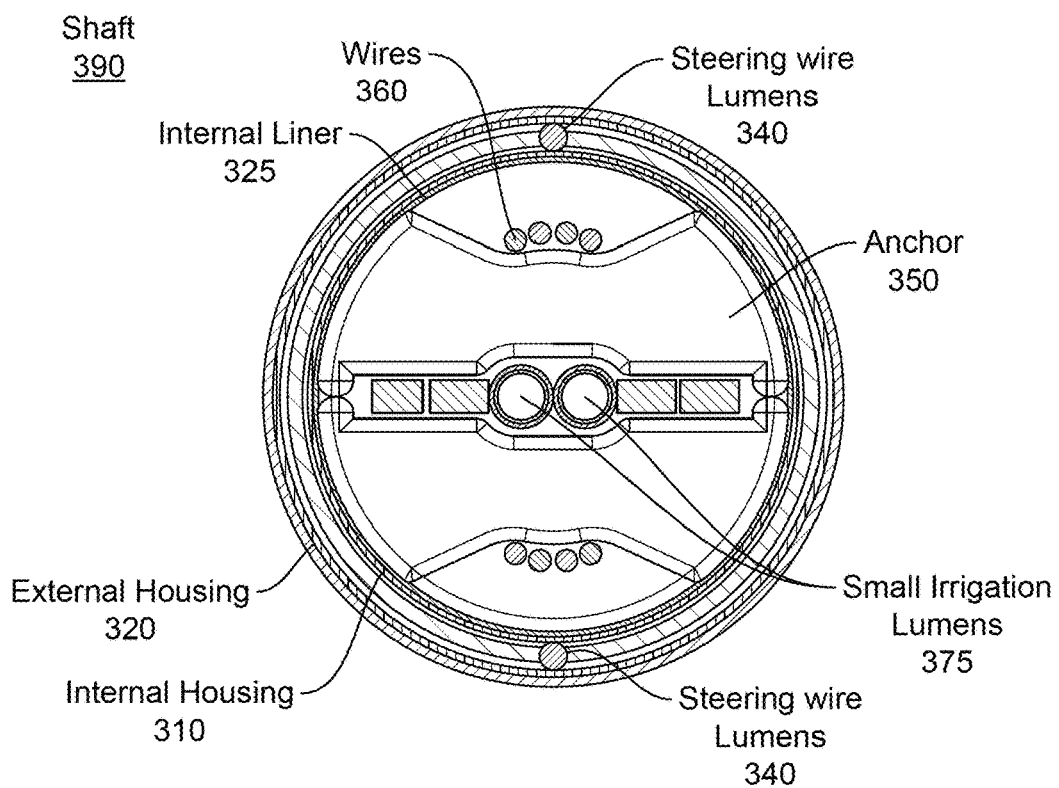

FIGS. 3D & 3E illustrate cross-section views of a shaft 390 that may be implemented in the treatment device 105, in accordance with some embodiments. Shaft 390 is another example of shaft 150 illustrated in FIG. 1A. FIG. 3D illustrates a proximal cross-section view of the second shaft 390 of the heart treatment device, in accordance with some embodiments. FIG. 3E illustrates a distal cross-section view of shaft 390, in accordance with some embodiments.

The shaft 390 comprises many similar components to the shaft 300. In particular, the shaft 390 comprises, among other components, an internal housing 310, an external housing 320, an internal liner 325, a steering ring 330, steering wire lumens 340, an anchor 395, conductor wires 360, and irrigation lumens. The anchor 350 of the shaft 390 is shaped differently than the anchor 350 of the shaft 300. The anchor 350 of shaft 390 comprises two pieces that interface along two contact points towards the circumference of shaft 390. The anchor 350 of shaft 390 has a larger cross-section area in proportion to the cross-section area of shaft 390 than the anchor 350 of shaft 300. The thicker anchor 350 provides added strength and support. In shaft 390, the wires are also dispersed in both halves of shaft 390, the halves created based on the coupling contact points of the two pieces of the anchor 350. Also, the shaft 390 comprises two small irrigation lumens 375 that split from the main irrigation lumen 370 towards a proximal end of the shaft 390.

Example Catheter Designs

Figure 4A:
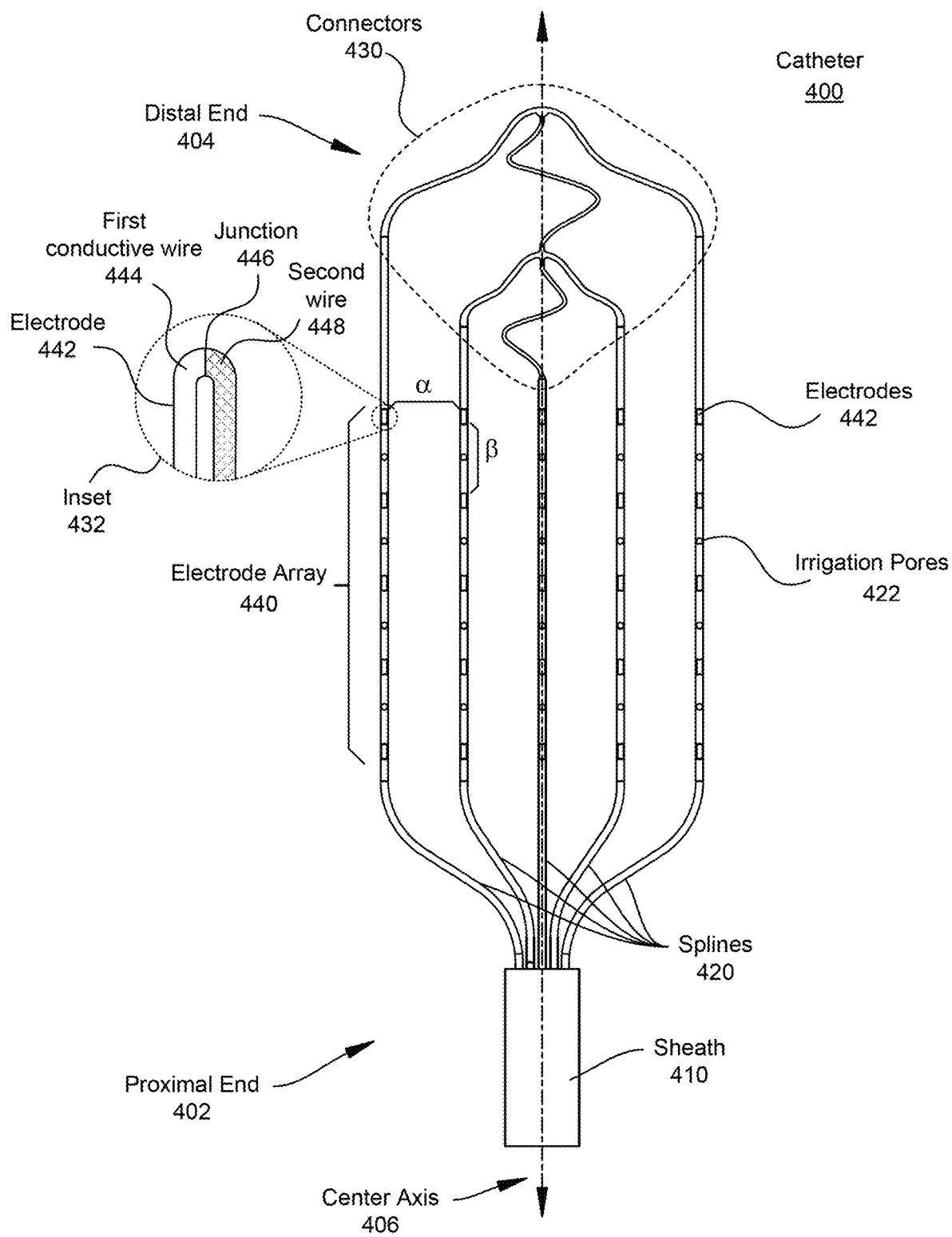
FIG. 4A illustrates a top view of a catheter that may be implemented in the treatment device, in accordance with some embodiments.

FIG. 4A illustrates a top view of a first catheter 400 that may be implemented in the treatment device 105, in accordance with some embodiments. The catheter 400 is an embodiment of the catheter 155. The catheter 400 is shown in an expanded state, wherein the catheter 400 is unsheathed from the sheath 410, i.e., extended away from the sheath 410. The catheter 400 includes, among other components, a plurality of splines 420, a plurality of connectors 430, an electrode array 440 that includes multiple electrodes 442, and irrigation pores 422. Other sensors in some embodiments may include temperature sensors, force-sensing elements, and photoelectric sensors to identify changes to tissue composition prior to and during ablation to verify the treatment effect. For some embodiments, magnets can be added to enable positional sensing within the body for some mapping systems. In one or more embodiments, the sheath 410 is a component of the treatment device 105. However, in other embodiments, the sheath 410 may also be an external component, such that the catheter 400 and the shaft 150 are inserted into the sheath 410.

For discussion purposes, the proximal end 402 of the catheter 400 is towards the shaft 150 and the handle 146, whereas the distal end 404 of the catheter 400 is opposite from the proximal end 402. A center axis 406 runs through the center of the sheath 410 and the shaft 150 from the proximal end 402 to the distal end 404.

The sheath 410 is configured to store the catheter 400 in a compact state. The sheath 410 is a substantially rigid component that can hold the catheter 400 in a compact state as it is introduced into the blood vessel. The rigidity of the sheath 410 must be sufficient to avoid elastic deformation when the catheter 400 is held in the compact state and applying an outward force against the sheath 410 e.g., in a radial direction away from the center axis 406. In one or more embodiments, the sheath 410 is substantially of a cylindrical shape capable of fitting around the shaft 150. As such, the sheath 410 can translate along the center axis 406 relative to the shaft 150. The catheter 400 extends beyond the sheath 410 to transition into the expanded state and retracts into the sheath 410 to transition into the compact state (also referred to as the compact state). In some embodiments, the catheter 400 is moved relative to the sheath 410 by the handle 146. In other embodiments, the sheath 410 is moved relative to the catheter 400 by the handle 146.

The sheath 410 can be straight or have varying degrees of curvature at the distal end to facilitate maneuverability to regions within the organ. In one embodiment, the sheath has a tapered shape at the distal end to facilitate extension and retraction of the catheter 400. Some sheaths have varying "deflectable" curvatures. Collapse of the catheter within the sheath should be smooth without undue force. It also should not inadvertently trap tissue as it is pulled into the sheath. The closed design of the electrode array catheter in many embodiments prevents such events. Catheter shapes in other embodiments may include the ability to deliberately 'attach' to structures for stability, such as for ablation of the papillary muscles which is typically limited by catheter slippage.

In embodiments where the sheath 410 is a separate component from the catheter 400, an introducer tool may be implemented for compacting the catheter 400 to the compact state for insertion into the sheath 410. The introducer tool may have a tapered form that aids in transitioning the catheter 400 into its compact state. The introducer tool may also couple to the sheath 410 at a proximal end that remains external to the patient during the procedure. A physician inserts the catheter 400 through the introducer tool to transition the catheter into its compact state and into the sheath 410. The catheter 400 in its compact state can be translocated through the sheath 410 to a distal end that is guided to the treatment site.

The plurality of splines 420 provides a structure for contacting the heart tissue with the catheter 155. The splines 420 are flexible and insulative, e.g., formed with Nitinol having an insulative coating composed of polyether block amide (PEBA). In other embodiments, other flexible materials, that are also safe for invasive procedures, may be used. Other example materials that may be used for the splines include but are not limited to, alloys composed of Ti—Nb, Ti—Mo, Ti—V, other Beta titanium alloys, Cu—Zn—Al, other Beta brass alloys, Cu—Al—Ni, Cu—Al—Be, other bronzes, Fe—Mn—Si, Fe—Co—Cr, other iron-based alloys, Ni—Al, In—Tl, U—Nb, Au—Cd, Ag—Cd, Ru—Ta, other alloys of sufficient flexibility and elasticity (atomic symbols used herein). Other example insulative materials that may be used include, but are not limited to, polyimides, polyamide-imides, PTFE, other high-performance plastics, etc. The flexibility allows for the splines to flex and conform to the non-planar topography of the heart tissue. The flexibility of the splines 420 helps in the extension and retraction from the sheath 410. The splines 420 include a substantially linear portion where the electrodes of the electrode array 440 are disposed on. Towards the proximal end 402, one or more splines include a curved portion that connects the respective linear portion extended beyond the sheath 410 and another linear portion that remains within the sheath 410. The curved portion aids in the expansion and the collapse of the catheter 400. Within the plurality of splines 420 are wiring and irrigant fluid channels, which connect to the electrode array 440 and the irrigation pores 422. In the expanded state, the plurality of splines 420 are spaced apart. As shown, the splines 420 are evenly spaced apart; however, other embodiments may utilize variation in the spacing between adjacent splines.

The connectors 430 connect the splines 420 to ensure the splines 420 remain in a planar orientation. The connectors 430 are also flexible and insulative, e.g., formed with Nitinol with an insulative coating. Each connector includes one or more bends in its shape. One or more bends in a connector are capable of storing energy when deformed, wherein that energy is used to separate the splines when the catheter 400 is unsheathed, i.e., extended from the sheath 410. As the catheter 400 is retracted into the sheath 410 (into a compact state, also referred to as a compact state), one or more bends of the connectors are deformed storing potential energy in the bends. Each bend has a particular curvature. As the curvature is changed by deformation, i.e., increased or decreased, the material stores both compressive and tensile potential energy. As the catheter 400 is extended from the sheath 410 (into an expanded state), the stored potential energy causes the connectors 430 to return to a default shape where the splines 420 are spaced apart. In one or more embodiments, the splines 420 and the connectors 430 may be monolithic, i.e., formed from one contiguous piece of material.

The electrode array 440 is disposed on the splines 420. The electrode array in some embodiments should be large enough to cover critical areas for biological rhythm disorders, yet small enough so that a practical number of electrodes can provide high-spatial resolution recordings. In some embodiments, the size of the intracardiac system may be personalized to the biological rhythm disorder.

As shown in FIG. 4A, the array may be a substantially rectangular array of multiple electrodes 442 defined by a repeating rectangular grid with dimensions $\alpha \times \beta$, wherein a is the dimension perpendicular to the center axis 406 and B is the dimension parallel to the center axis 406, and wherein an electrode is placed at each vertex of the rectangular pattern. As a numerical example, there is a total of twenty-five electrodes 442 in the electrode array 440, with five electrodes disposed on each of five splines, with rectangular grid dimensions: a is 2 mm and $\beta$ is 2 mm.

The range of electrodes for an intracardiac system for heart rhythm applications is typically 4 to 128. In the embodiment in FIG. 4A, the mapping electrode array (or 'waffle', or 'spade' or 'grid') is about 2 cm×2 cm (W×L) (range 1 cm×1 cm to 5 cm×5 cm). A typical arrangement for mapping AF would be 16-64 electrodes in an area of 2 $cm^2$ to 16 $cm^2$. A typical arrangement for mapping gaps in a pulmonary vein encircling line would be 4-16 electrodes in an area of 1-2 $cm^2$. A typical arrangement for mapping critical regions for ventricular tachycardia would be 9-25 electrodes in an area of 2-4 $cm^2$. The size of this electrode array can also be personalized to the profile of the patient, using tools such as machine learning calibrated to patients of similar clinical type and data.

FIG. 4A illustrates 5×5 electrodes in a uniform grid. The choice of an odd number of electrodes 442 along each axis enables the device to provide a 'center point' with peripheral electrodes in a symmetrical design to map centrifugal activation from a focus or uniform circular re-entry around this central point. Configurations with 4×4 electrode combinations are less well suited for this specific application but have other potential applications. Other even combinations of electrodes require an off-center electrode at the center of rotation or focal activity, with an asymmetry of surrounding electrodes which is wasteful of size and may introduce difficulties of recording from practical clinical electrophysiological amplifiers that have a fixed number of recording channels.

The size of the electrode array 440 may vary with the organ being treated. The size may be smaller for a device in the brain, where small size is at a premium to avoid destruction of tissue, than for a device in the heart, where larger mapping and ablation areas are sometimes needed. The therapy tool contacts the organ by conforming to its surface at a plurality of locations.

In some embodiments, the array 440 may be imperfect, i.e., the array 440 is not formed by repetition of one grid. For example, the spacing between adjacent splines 420 can vary or the spacing between electrodes on a single spline can vary. Typically, the number of channels that can be sensed in a patient is limited by the recording amplifier. The advantage of a variably spaced array is this fixed number of electrodes can be distributed with a high-spatial solution in a central cluster to define ablation patterns, yet with peripheral electrodes to enhance directional navigation (for instance "move catheter left") In one or more embodiments, the characteristics of the electrode array 440, e.g., placement of each electrode within the electrode array 440, can be tailored and optimized for a particular patient.

In some embodiments, each electrode 442 of the electrode array 440 is capable of sensing electrical signals of the heart tissue and delivering ablation energy to the heart tissue. Each electrode 442 may be formed from a conductive material coupled circumferentially to the respective spline that the electrode is disposed on. Example materials that can be used to form the electrodes include, but are not limited to, copper, gold, platinum, metal alloys containing gold, metal alloys containing platinum, gold-plated copper, other conductive metals, other conductive metal alloys, etc. In one or more embodiments, the electrode material is also safe for use in blood. For example, the size of each electrode in FIG. 4A is on the order of 0.8 mm in diameter (it is a cylinder), measured along the center axis 406 and 1 mm along the spline. This small electrode sizing provides for very high-resolution sensing by the electrode array 440. It is well understood that the size of a measurement device (in this case, an electrode of the array 440) limits the measurement resolution that can be achieved by the measurement device.

Referring to the inset 432, an illustrative structure of an example of electrode 442 is shown in an enlarged view. An electrode 442 may include a first conductive wire 444 and a second wire 448. The first conductive wire 444 may be referred to as a treatment wire or an ablation wire and the second wire 448 may be referred to as a sensing wire. The first conductive wire 444 and the second wire 448 creates a junction 446. The first conductive wire 444 may be formed of a first material such as copper, gold, platinum, metal alloys containing gold, metal alloys containing platinum, gold-plated copper, other conductive metals, other conductive metal alloys, etc. The first conductive wire 444 may be connected to a power generator 115 (not shown in FIG. 4A) and to carry a current to deliver ablation energy to biological tissue. Each conductive wire 444 of the various electrodes may individually carry a current level that is controllable by the power generator 115.

The second wire 448 is illustrated in inset 432 with a shared pattern and is in contact with the first conductive wire 444. The second wire 448 is formed of a second material different from the first material. The second material may be a metallic material or any suitable material that forms a thermocouple with the first conductive wire 444. In some embodiments, the second material may be constantan or any suitable alloy that creates a good thermocouple with the first material. In some embodiments, the first material has a first impedance and the second material has a second impedance that is higher than the first impedance. In some embodiments, the second wire 448 is part of the circuitry of the electrode 442 and serves as part of a return path of the circuitry.

The arrangement shown in inset 432 allows for coincidental sensing and energy delivery. The first conductive wire 444 of electrode 442 carries the ablation energy so that the electrode 442 is capable of delivering the ablation energy. Junction 446 creates a thermocouple such as electrode 442 is also capable of sensing the temperature at electrode 442. In some embodiments, the electrode 442 includes a single circuitry that serves as both the ablation element and the temperature sensor.

While electrode 442 is illustrated in inset 432 as a bent wiring with a tip, electrode 442 in various embodiments can take many forms and shapes and the shape in inset 432 is merely an example illustration. For example, in some embodiments, electrode 442 may be largely a straight line and junction 446 is a transition point from the first conductive wire 444 to the second wire 448 in the straight line. The first conductive wire 444 and second wire 448 may join each other through soldering, physical contact, circuit board printing, additive manufacturing, welding, or any of the combinations. In various embodiments, junction 446 may not be located at the tip of electrode 442 but can be located at any exposed section of electrode 442. For example, in some embodiments, a majority of the first conductive wire 444 and a majority of the second wire 448 are insulated and located within the lumen of a spline 420. The electrode 442 may be formed of an exposed part of the first conductive wire 444 and an exposed part of the second wire 448. The Junction 446 may be located anywhere at the exposed part of the first conductive wire 444 and the exposed part of the second wire 448.

An electrode 442 may include a first conductive wire 444 that transfers electrical energy from handle 146 to electrode 442. The first conductive wires 444 connected to the electrodes may be substantially large in diameter to transfer the required ablation energy from generator 115 to electrode 442. Each of the electrode 442 may have its own conductive wire 444 so that the ablation energy delivered at each electrode 442 may be individually regulated. The ablation energy may be required for pulsed-field ablation or other high-energy applications. The conductive wires 444 may be insulated to prevent unwanted discharge of electrical energy that could cause damage to tissue not being treated or damage to the components of the treatment device 105.

In various embodiments, wires in this disclosure may include a metallic wire in a conventional sense, but may also include other types of conductive pathways that are not in a thread-like elongated structure. For example, a "wire" may take the form of a trace or conductive path in a printed circuit board, such as a flexible circuit 450 illustrated in FIG. 4B. While the inset 432 illustrates an example structure of an electrode 442, in other embodiments an electrode 442 may also be created in a different design, such as a single wire design that is coupled with an electronic temperature sensor. Other suitable ways to create an electrode 442 are also possible.

Figure 4B:
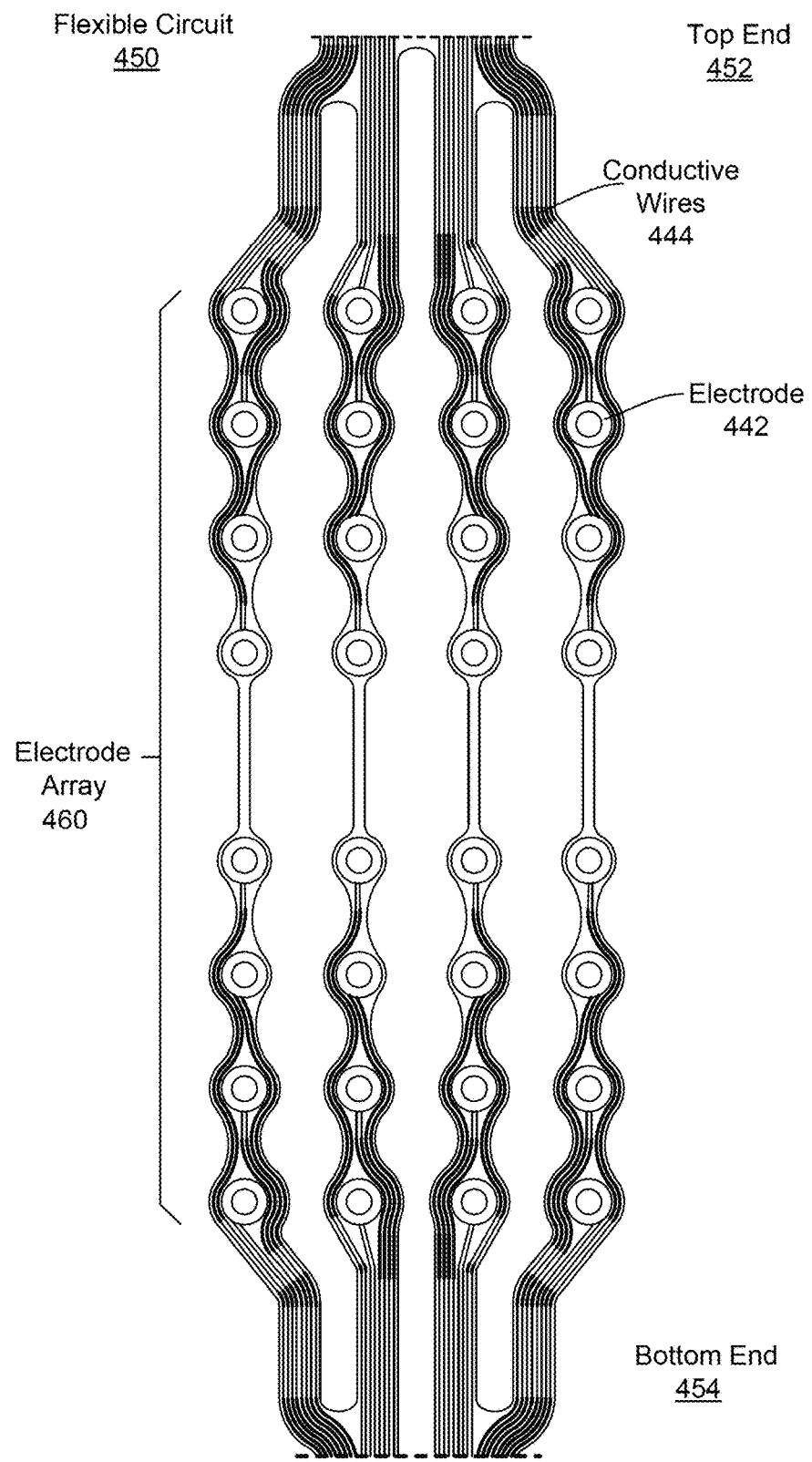
FIG. 4B illustrates a flexible circuit that can be implemented with the catheter 400, in accordance with some embodiments.

FIG. 4B illustrates a flexible circuit 450 that can be implemented with the catheter 400, in accordance with some embodiments. The conductive paths of the flexible circuit 450 may be examples of conductive wires, wrapping around the inflatable member. The flexible circuit 450 may include a plurality of tendons that are connected at a top end 452 and a bottom end 454. Printed on the tendons are the electrodes 442 and the wires 444. As the flexible circuit 450 wraps around the inflatable member on a top flat side and a bottom flat side, the electrode array is disposed on both sides, allowing for electrode functionality from either side of the catheter 400.

While not illustrated graphically in FIG. 4B, the thermocouple wire arrangement illustrated in inset 432 by using two materials in contact at an electrode 442 may also be implemented in FIG. 4B.

Examples of catheters 400 illustrated in FIG. 4A and FIG. 4B are designed to provide deep and durable tissue modification or destruction (e.g., ablation) through small electrodes 442 which are also well suited to sense at high resolution. In some embodiments, a catheter 400 includes an array of electrodes 442 and each electrode 442 may be individually regulated by a power generator 115 so that electrode 442 can individually sense temperature and deliver ablation energy at a desired level. This enables very precise and specific ablation patterns to be delivered in regular, irregular and personalized shapes tailored to the specific rhythm disturbance in that patient. The ability to deliver ablation through these small electrodes may be attributable to the materials used and the energy waveform approaches. While in this disclosure a catheter may be illustrated as having electrodes 442 that are individually regulated, in some embodiments the electrodes 442 may also be grouped by subsets and each subset that includes a few electrodes 442 in proximity may be individually regulated.

The individual regulation of current delivered to an electrode improves over various conventional catheters where the same current is delivered to multiple electrodes. In an ablation procedure, much of the current are not returned through return wires of the catheter 155. Instead, the current may go through the body of the patients. In conventional catheters, the impedance at electrodes that have poor contact are high and current tends to flow through electrodes that have proper contact. In an ablation procedure, the individual contact of electrode is often varying due to the complex biological environment and uneven surfaces at the biological tissue. As such, conventionally it is difficult to precisely control the ablation location based on the electrodes and the temperature at each electrode. Also, conventionally a temperature sensor is located at the proximate end of a spline. Conventional catheter fails to provide information as to the ablation temperature and extent at each electrode 442.

In some embodiments, an electrode 442 may be operable in one or more configurations. For example, in some embodiments, an electrode 442 may be operable in a sensing configuration. Alternatively, or additionally, the electrode 442 may be operable in an ablation configuration. Alternatively, or additionally, the electrode 442 may be operable in a coincidental sensing and ablation configuration.

In a first sensing configuration, an electrode 442 can be configured to measure electrical signals and to provide the electrical signals to the control system 110. The electrical signals collected by each electrode can include: a voltage signal, a current signal, an impedance signal, another electrical parameter, etc. The spacing between adjacent electrodes in the electrode array 440 can be sufficiently small so as to provide high-resolution sensing of the electrical activity of the heart tissue. The electrical signals are used by the control system 110 to determine guidance instructions for the movement of the catheter 400 towards a source region that requires ablation therapy. In some embodiments, the spacing between two adjacent electrodes may be in the range of 2 mm. In some embodiments, the spacing between two adjacent electrodes may be in the range of 0.5 mm-5 mm.

In a second sensing configuration, an electrode 442 can be configured to measure temperature to provide measurements of the ablation temperature. In the example configuration illustrated in the inset 432, the temperature measurement may take the form of thermocouple voltage that is transmitted to the power generator 115. Each electrode 442 in an array may have an individual thermocouple. As such, the temperature of the electrodes 442 may be individually measured. In some embodiments, instead of using a thermocouple as a way to measure temperature, an electrode 442 may also carry another form of temperature sensor.

In an ablation configuration, an electrode 442 can be configured to deliver ablation energy to heart tissue. The ablation energy is in the form of electrical energy received from the generator 115. As noted above, the ablation energy may be tailored, e.g., at a particular frequency or wavelength, with a particular waveform, over a particular duration. This includes common 'moderate power, moderate duration' energy such as 30-50 W at 15-60 seconds, as well as 'high power short duration' energy such as 50-90 W at 5-15 seconds. This also includes very high powers associated with pulsed-field ablation (to cause irreversible electroporation). In some embodiments, an electrode 442, in the ablation configuration, is capable of achieving more than 3 mm in depth of delivery of ablation energy. In some embodiments, each electrode 442 is addressable independently. The electrode array 440 is capable of delivering ablation energy in a variety of ablation patterns that can be tailored to each critical region for the biological rhythm disorder identified by the control system 110. This is advantageous as the catheter 400 need not perform multiple ablation steps to achieve a particular pattern, which would otherwise be the case with singular ablation electrode catheters or even linear ablation catheters. For example, to create a cross pattern with a linear ablation catheter, a conventional linear ablation catheter would need to perform at least two steps to ablate the two arms of the cross pattern with the additional movement necessary to change the positions of the catheter. However, the electrode array 440 of the catheter 400 could achieve the cross pattern by selectively addressing all the electrodes in the middle spline and the middle electrodes in the other splines. The electrode array 440 could thus ablate with the cross pattern in a single step, without needing to reposition the catheter 400. In this fashion, a circular, arc-shaped, or other ablation configuration can be readily delivered depending on the physician's selection for that biological rhythm disorder in that patient.

In some embodiments, an electrode 442 is configured to deliver an alternating current (AC) as the current that delivers the ablation energy. In some embodiments, the alternating current has a monochromatic frequency. In some embodiments, the frequency of the alternating current is higher than 100 kHz. In some embodiments, the frequency of the alternating current is higher than 150 kHz. In some embodiments, the frequency of the alternating current is higher than 200 kHz. In some embodiments, the frequency of the alternating current is higher than 300 kHz. In some embodiments, the frequency of the alternating current is around 400 kHz. In some embodiments, the frequency of the alternating current is higher than 500 kHz. In some embodiments, the frequency of the alternating current is higher than 600 kHz. In some embodiments, the frequency of the alternating current is higher than 700 kHz. In some embodiments, the frequency of the alternating current is higher than 1000 kHz. The selection of the frequency may be determined based on design. In some embodiments, the choice of frequency may be used to prevent a biological tissue or muscle from resonating with the current frequency. For example, in some embodiments, biological tissue is incapable of vibrating at or beyond a certain frequency, such as 100 kHz. In some embodiments, the current delivered at each electrode 442 is an AC current but does not cause any muscle stimulation.

In some embodiments, the frequency of each electrode 442 may be individually regulated. In some embodiments, the currents delivered at multiple electrodes 442 are synchronized so that the phase of the currents delivered at a biological tissue is not affected by other noisy phases. In some embodiments, the various electrodes 442 in the array deliver currents in the same frequency but in different amplitudes. In some embodiments, other distributions of amplitudes, phases, and frequencies among the electrodes 442 of the array are also possible. Those parameters may be controlled by a power generator 115.

The irrigation pores 422 vent irrigant during an ablation procedure. The irrigation pores 422 are openings in the splines 420 which permit liquid irrigant to escape from the splines 420. The splines 420 thus can also operate as irrigant fluid channels. As shown in FIG. 4A, the irrigation pores 422 are disposed in between adjacent electrodes on a spline. Following the numerical example above, there is a total of twenty irrigation pores 422, with four irrigation pores 422 disposed on each spline of five splines, interlaced between the electrodes on each spline. The irrigation pores 422 can be both on the top side (in the view from the top view) and on the bottom side (obscured from the top view), which is opposite the top side. In another example, there is a total of forty irrigation pores 422, twenty on the top side and twenty on the bottom side. In other embodiments, there can be additional or fewer irrigation pores than shown in FIG. 4A. For example, the ratio of irrigation pores to electrodes can range from 2:1 (two irrigation pores to each electrode) to 1:9 (one irrigation pore to nine electrodes).

Venting irrigant during an ablation procedure is important to prevent searing of the tissue, the irrigant acts to spread the energy so that no region becomes too hot, thus searing the tissue. Prevention of tissue-searing allows for lengthier ablation procedures which can help achieve greater depth in delivery of ablation therapy and can also prevent scarring of the tissue. Irrigation pores can be independently addressable to limit the extent of fluid delivery, for instance in patients with existing heart failure. Typically, for safety, all irrigation pores may be used simultaneously. The placement of the irrigation pores 422 in proximity to (e.g., within a couple of millimeters) the electrodes of the electrode array 440 provides sufficient irrigant to prevent tissue char, thereby enabling the potential for delivering the ablation energy in a variety of ablation patterns.

In one or more embodiments, one or more temperature sensors may be implemented on the catheter 400. The temperature sensors measure the temperature of tissue in contact with the temperature sensors. Temperature sensors can be near multiple electrodes, on each spline, or in other configurations. In some embodiments, the temperature sensors measure a change in electrical resistance, electrical voltage, or another electrical metric within a circuitry having a temperature-sensitive material. Examples of temperature sensors include a resistance temperature detector, a thermocouple, a thermistor, etc. In other embodiments, non-contact temperature sensors may be used, e.g., infrared photoelectric sensors.

In one or more embodiments, one or more force-sensing elements may be implemented on the catheter 400. The force-sensing elements measure the contact force between the catheter 400 and the tissue. The measured contact force can be used to verify contact between the catheter 400 and the tissue during sensing and/or ablation. The force-sensing elements may be piezoelectric sensors, surface capacitance sensors, etc.

In one or more embodiments, one or more photoelectric sensors may be implemented on the catheter 400. The photoelectric sensors may be used to identify changes to tissue composition prior to, during, or after ablation. The photoelectric sensors may also be infrared sensitive to determine the temperature of the tissue.

Figure 5A:
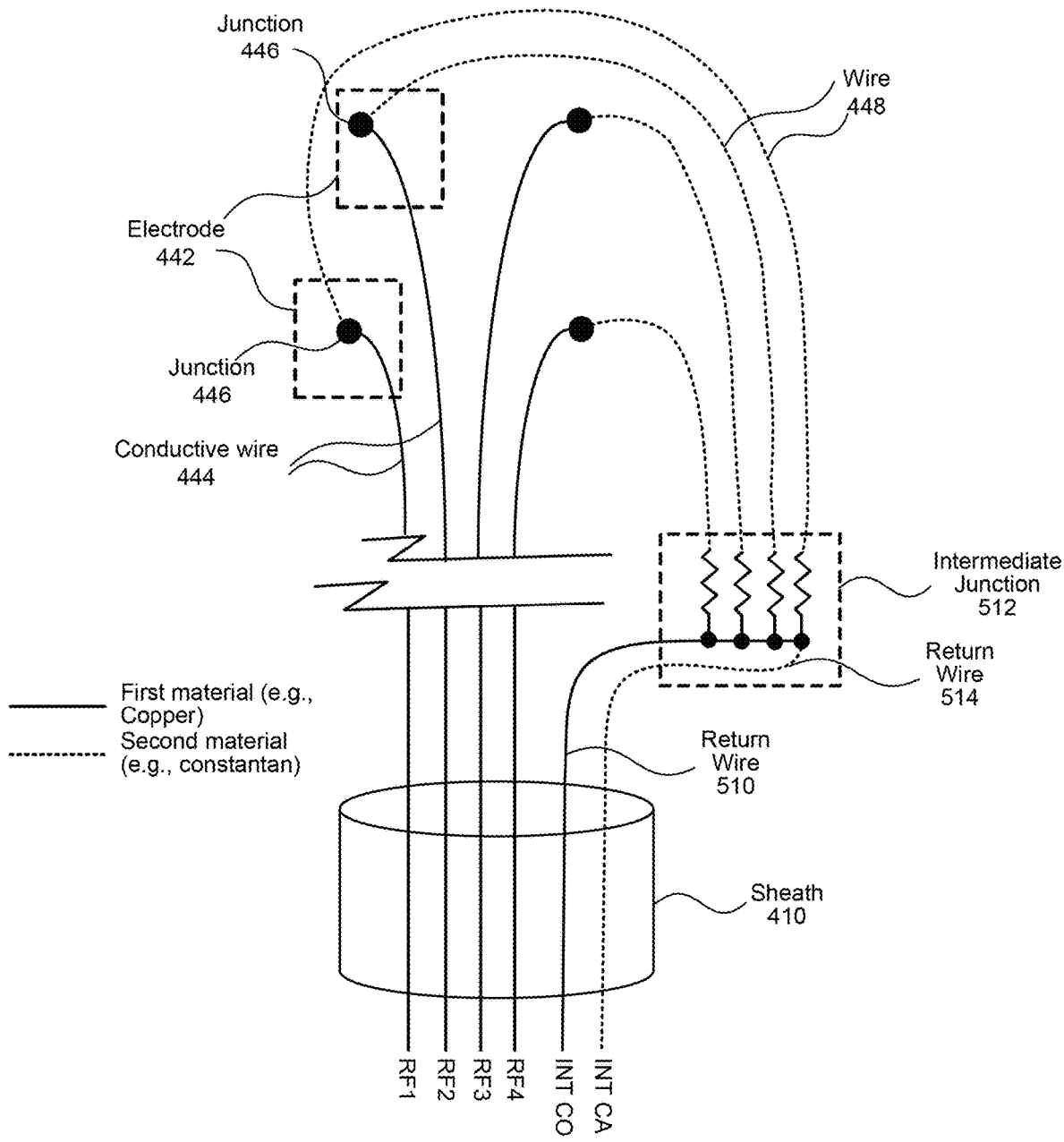
FIG. 5A is a conceptual diagram illustrating an example configuration of the wiring of a catheter, in accordance with some embodiments.

FIG. 5A is a conceptual diagram illustrating an example configuration 500 of wiring of a catheter 400, in accordance with some embodiments. The configuration 500 allows for the coincidental sensing and ablation by using first conductive wires 444 and second wires 448 made of different materials to form thermocouples at junctions 446. The configuration 500 illustrates the wiring configuration of a few electrodes 442 that share a common return wire 510. The use of the common return wire 510 reduces the number of wires in this configuration 500, thus reducing the complexity and size of the catheter 400.

In some embodiments, each of the multiple electrodes 442 includes an individual wire that is connected to a power generator 115. The individual wires in configuration 500 are illustrated as multiple conductive wires 444, such as RF1, RF2, RF3, and RF4. Each conductive wire 444 may carry current at a specific frequency.

In FIG. 5A, an electrode 442 is illustrated as a dash-lined box that includes a portion of a first conductive wire 444 and a portion of a second wire 448. Each electrode 442 may include a junction 446 between a conductive wire 444 and a second wire 448. For example, for the two electrodes illustrated on the left, the configuration 500 includes a first conductive wire 444 formed of a first material. The first conductive wire is configured to be connected to a power generator and to carry a current to deliver ablation energy to a biological tissue. The configuration 500 also includes a second wire 448 coupled to the first conductive wire 444 at a junction 446. The second wire 448 is formed of a second material different from the first material. The first conductive wire 444 may be used as an ablation element to deliver ablation energy. The junction 446 may serve as a temperature sensor such that a thermocouple between the first conductive wire 444 and the second wire 448 are formed at the junction 446 to measure temperate at the electrode 442. The configuration 500 may also include a third conductive wire 444 formed of the first material. The third conductive wire is configured to carry a second current that serves as part of a second ablation element to deliver ablation energy. The configuration 500 may also include a fourth wire 448 formed of the second material. The fourth wire may form a junction with the third conductive wire. As such, in a second electrode, a second thermocouple and a second ablation element are formed. The configuration 500 may also include a fifth conductive wire, a sixth wire, a seventh conductive wire, an eighth wire, etc. as illustrated by the two electrodes on the right.

In some embodiments, multiple electrodes 442 may share a return wire 510 to reduce the overall number of wires. The common return wire 510 may be made of the first material. In some embodiments, an additional thermocouple wire 514 made of the second material may also be present. An electrode 442 uses the wires 448 made of the second material as part of the circuitry. Multiple electrodes 442 are met at the intermediate junction 512 to be connected to the common return wire 510. The voltage between one of the conductive wires 444 (e.g., RF1, RF2, etc.) and the common return wire 510 may be measured as the thermocouple voltage for a particular electrode 442. As such, even though a common return wire 510 is used, the temperature of each electrode 442 may be individually measured. The common return wire 510 also completes the circuitry of each conductive wire 444 so that individualized ablation current may be delivered at each electrode 442. Each electrode 442 may be able to deliver ablation energy at a different level independent of other electrodes 442 in the set.

The additional thermocouple wire 514 provides a second thermocouple (in addition to individual thermocouples at the electrodes 442) between the common return wire 510 and the additional thermocouple wire 514. This second thermocouple 514 is located at the intermediate junction 512 so that the thermocouple voltage and temperature at the intermediate junction 512 can be measured. The thermocouple voltage and temperature at the intermediate junction 512 are measured as references to the thermocouple voltage and temperature at the electrodes 442 so that the temperature of the individual electrodes 442 can be accurately measured.

The configuration 500 illustrates an embodiment of N+2 electrodes and wires, where N equals the number of electrodes and N+2 equals the number of wires. For example, the particular example in FIG. 5A illustrates a 4-point electrode with 6 wires. In some embodiments, the additional thermocouple wire 514 made of the second electrode may also be removed. As such, the configuration may become an N+1 configuration. In some embodiments, the number of wires may be any number between N+1 and 2N. For example, in some embodiments, each electrode 442 may have its own dedicated return wire so that the number of wires is equal to 2N. In some embodiments, all of the electrodes 442 in a catheter 400 are connected to a single return wire 510. As such, the number of wires is equal to N+1. In some embodiments, the electrodes 442 may be grouped as subsets. For example, the electrodes 442 in one spline 420 illustrated in FIG. 4A may be grouped as one subset and may share a common return wire 510. For example, the configuration 500 illustrated in FIG. 5A may correspond to one column of electrodes 442 located in a spline 420 of FIG. 4A. The intermediate junction 512 may be located inside the spline 420 or in the area of the sheath 410. In some embodiments, another subset of electrodes 442 in another spline 420 may share another common return wire 510.

In some embodiments, an electrode 442 incorporates an intermediate common cold junction within the catheter 155 itself as illustrated in FIG. 5A. In this embodiment, each probe point is connected to a single wire (copper) which is used both as a biological sense lead and for the delivery of AC therapy for the treatment of the tissue. Each of the probe points is additionally connected to a common intermediate cold junction within the probe using a thermocouple wire (constantan) and resistive isolators. The location of this intermediate cold junction is chosen to be sufficiently removed from the thermal activity to ensure that it is not significantly affected by the therapy being delivered. An additional temperature sensor is included at this intermediate cold junction so that its absolute temperature can be determined. This configuration allows monitoring of electrical signals, the delivery of AC therapy and the measurement of individual probe tip temperatures for a device with N probe positions with as few as N+2 wires in the catheter 155. This reduction in the number of wires may greatly reduce the complexity of probe design, reduce its size and hence increase the number of elements that can be supported in a practical probe size.

Figure 5B:
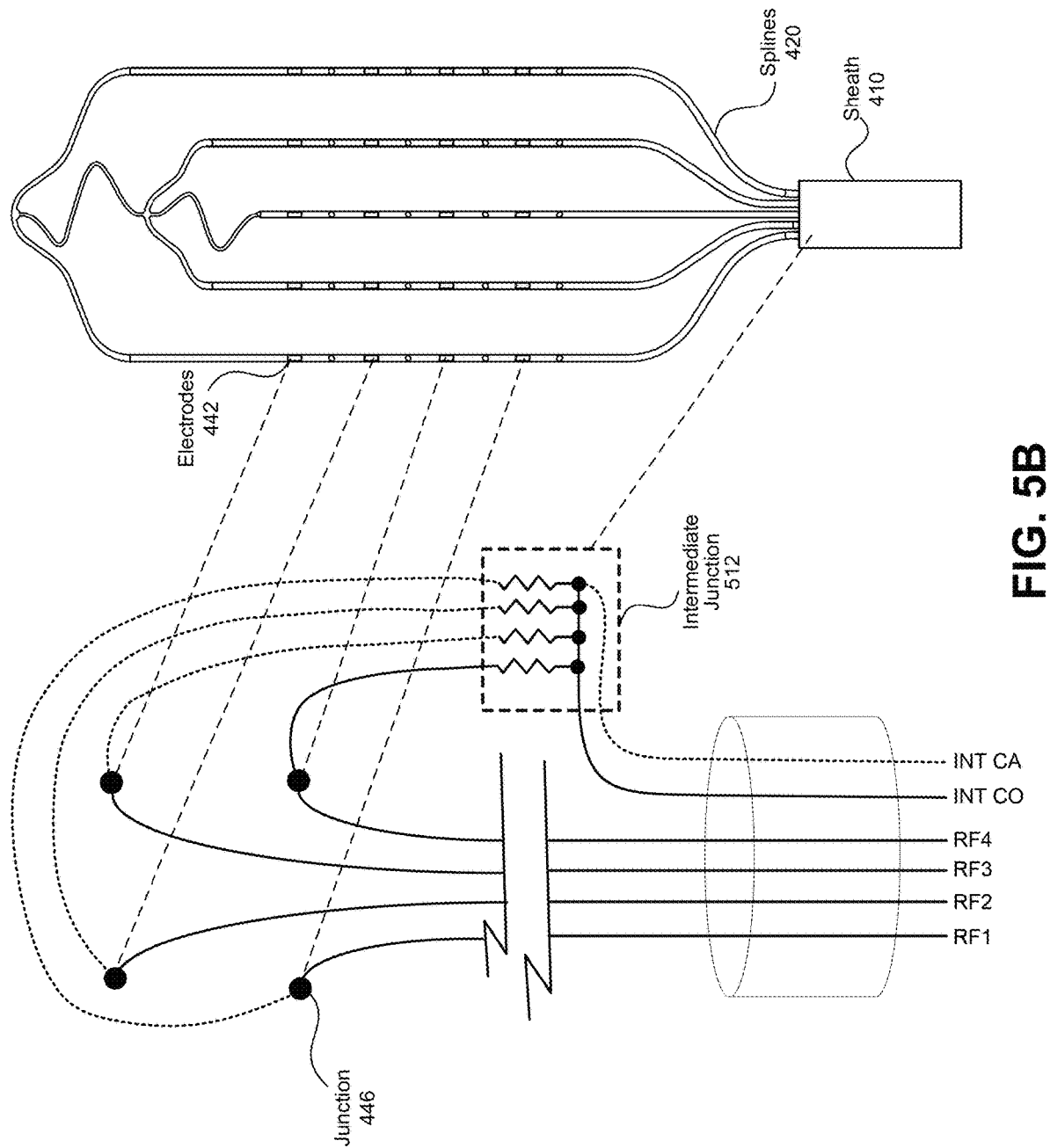
FIG. 5B is a conceptual diagram illustrating example locations of various components in the conceptual diagram of FIG. 5A relative to a design of catheter illustrated in FIG. 4A, in accordance with some embodiments.

The physical locations of various components in configuration 500 shown in FIG. 5A are for illustration only. For example, although the electrodes 442 are illustrated as a 2×2 array, in some embodiments the electrodes 442 are arranged in a linear fashion through a spline 420, such as those illustrated in FIG. 4A. The number of electrodes 442 in a subset may also vary in different embodiments. For example, a subset may include five electrodes instead of four that is illustrated in configuration 500. FIG. 5B is a conceptual diagram illustrating example locations of various components in the conceptual diagram of FIG. 5A relative to a design of catheter 400 illustrated in FIG. 4A. The dashed lines illustrate examples of the corresponding locations of various components. For example, each junction 446 may correspond to approximately the location of an electrode. The intermediate junction 512 may be located towards the proximal end of a spline 420 or in the area of the sheath 410.

Example Power Generator

Figure 6:
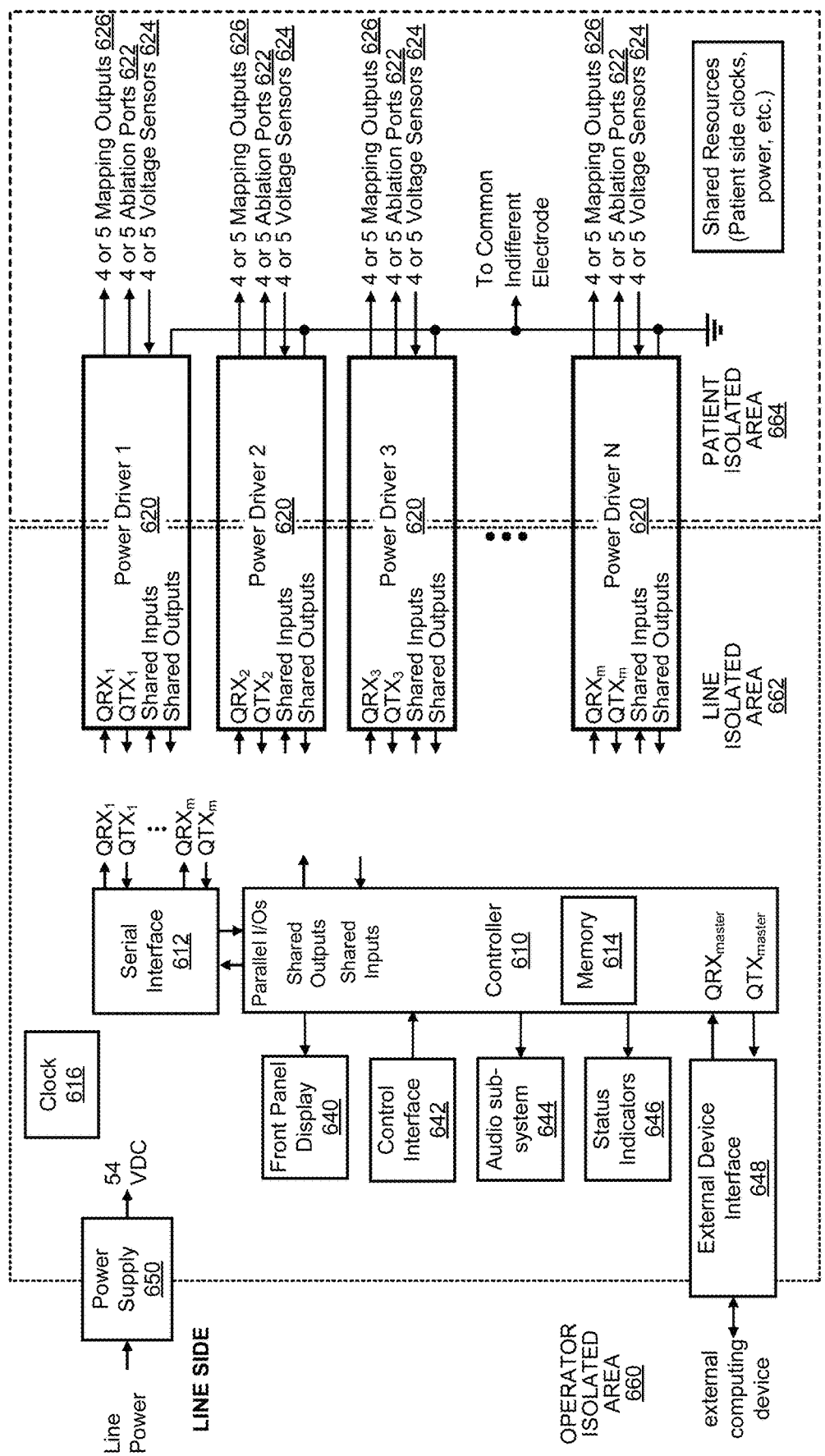
FIG. 6 is a block diagram illustrating an example generator, in accordance with some embodiments.

FIG. 6 is a block diagram illustrating an example generator 600, in accordance with some embodiments. The generator 600 is an example of the generator 115 that may provide power to a catheter 155 (not shown in FIG. 6). The generator 600 includes circuitry and components to deliver different levels of ablation energy individually to electrodes and also receive electrode-specific readings from catheter 155. In some embodiments, the generator 600 may include a controller 610, a serial interface 612, one or more power drivers 620, and other inputs and outputs components, such as ablation ports 622 and voltage sensors 624. In various embodiments, the generator 600 may include fewer, additional, or different components. The generator 600 may be modular in nature.

The architecture may incorporate connections to a separate or integrated mapping system with sensitivity in a preferred range. In some embodiments, the preferred range may be about in the range of 0.5 mV to 1.5 mV per electrode. In some embodiments, the preferred range may be about in the range of 0.1 mV to 1 mV per electrode. In some embodiments, the preferred range may be about in the range of 1 mV to 10 mV per electrode.

The architecture of the generator 600 may provide a multi-contact measurement for an alternating current ablation catheter 155, with a varying number of contacts. Each contact may be individually controlled and may correspond to an electrode of the catheter 155 or a subset of electrodes that are collectively controlled. For example, each contact may correspond to an electrode. The current level and phase may be individually controlled and readings from the electrode may be individually received and analyzed. In some embodiments, the number of contacts may go up to 256 contacts, but there can be no practical upper bound in some cases. In some embodiments, a sixteen contact generator 600 may be used with a catheter 155 that has electrodes in a 4×4 configuration. Other variants are 2×2, 3×3, 5×5, 4×5, 5×6, 6×6 or 8×5 (forty) contacts. The selection may vary with the biological tissue, disease state, and selected catheter. Some applications, such as within a blood vessel such as for vascular nerve ablation, or within the brain such as auditory nerve modulation, may be served by smaller catheters with fewer electrodes, or by non-square 2×1, 3×1, or other configurations. In some embodiments, the generator 600 has circuitry and components that support varying electrode numbers, spatial configurations, and geometries. For example, the generator 600 may be designed with a scalable architecture that can be tailored to the needs of different electrodes in a straightforward manner.

While not labeled and illustrated in FIG. 6, a motherboard may be used to carry most or all of the components in FIG. 6. In some embodiments, a motherboard of the generator 600 may have a number of card slots (e.g., 8), mechanically separated with the correct dimensions to permit up to such as eight cards of power driver 620 inserted. A suitable card cage is provided to mechanically affix each card firmly in position. Dedicated routing may be used for each card slot. Different configurations may require specific slots to be populated. AC output routing is pre-defined from each card slot to output ports, defining specific output cables for each configuration. The card slots provide power supplies, reference signals, measurement and control signals, and I/O to each power driver 620 in both the line isolated areas. Specifically, each card slot may include one or more signal components:

Line Isolated Ground
Line Isolated Power Supplies (54V, 12V, 5V, 3.3V, −5V)
Line Isolated References (9Rm, 3Rm, 2Rm, −4Bm)
Line Isolated Control Signals (SELTESTm, nTESTTCm, BLANKm)
Line Isolated Master Clock (F24m)
Line Isolated Fatal Fault Indicator (nFAULTm)
Line Isolated QQPD Programming Lines (nQMCLRx, QPGDx, QPGCx)
Line Isolated Master Sync (QSYNCm)
Line Isolated Digital Communications (QRXx, QTXx)
Patient Isolated Ground
Patient Isolated Power Supplies (5_V, 2_V, −2_V)
Patient Isolated Voltage Reference (2_R)
5 off Patient Isolated Probe Connections (PROBE_n, THERM_n)
5 off Patient Isolated Mapping Outputs (MAP_n)
Patient Isolated Cold Junction Reference Signals CJS_m.
Patient Isolated Clock Reference (CK_1Mm)
Patient Isolated Thermocouple Test Signal (TCT_M)

The generator 600 may include a plurality of power drivers 620 that communicate with the controller 610 through a serial interface 612. The serial interface 612 may take the form of a dedicated two-wire serial interface to each slot. With this number of slots, the serial interface 612 may include an external serial interface device. A common part of this type of system is a Quad Asynchronous Communications Element (ACE). The entire eight-slot interface would require a pair of these connected to the Parallel Master Port (PMP). Alternatively, a single device could be used and the remaining four Serial Interfaces could be provided using four of the integrated UARTs. This would leave 2 integrated UARTs available for other functions (connection to Remote Computer(s), connection to display, debugging port(s), etc.).

In some embodiments, in addition to the serial interface 612, the motherboard provides some shared I/O to the power drivers 620 via the card slot connectors. The I/Os are suitably buffered for distribution to the card slots. In some embodiments, one pin is allocated on each of the card slots to detect the presence of a power driver 620 in the slot, independently of the state of programming of the controller 610. The pin is pulled up on the motherboard and pulled down by a power driver 620. The controller 610 may detect which slots are loaded by scanning the array of slot detect pins.

In some embodiments, the controller 610 includes firmware or software code that includes instructions which, when executed by the controller 610, cause the controller 610 to perform various functions that are described in this disclosure. The controller 610 may be a microcontroller or a microprocessor. Unless otherwise specified about the distinctions, terms such as controller, processor, microcontroller, and microprocessor may be used interchangeably in this disclosure. The controller 610 may include various ports to receive and transmit signals and commands to other components. In controller 610 may be controlled by an external source such as through an external computer and may also include algorithms that control and regulate other components in the generator 600. The controller 610 may include parallel inputs/outputs (IOs) ports that are used to individually communicate with each power driver 620. The controller 610 may also include shared inputs and outputs that are transmitted simultaneously to the power drivers 620. In some embodiments, the generator 600 may include more than one type of controllers, such as a supervisory controller, and a number of channel controllers. In various embodiments, some of the functions of various controllers may be combined or distributed in manners that are not explicitly discussed in this disclosure.

In some embodiments, the controller 610 coordinates the actions and data flow in the generator 600. The functions performed by the controller 610 may be digital in nature, controlling the ablation process and collecting, storing, and displaying data. In some embodiments, the controller 610 may handle multiple channels of data, such as 40 channels. The controller 610 has the task of coordinating the user input, remote interface input, and outputting status and data to both the user and the remote interface. This includes displaying data and discrete indications via LEDs and/or other indicators. The controller 610 may also coordinate audio outputs such as status tones, warnings, and error tones. The controller 610 may also coordinate Power-On Self-Test (POST) and self-health monitoring using both analog measurements and digital communications with the array of other microcontrollers in the system. The controller 610 may terminate AC delivery in the event that a fatal fault has been detected.

In some embodiments, the generator 600 may include a non-volatile memory 614 that is used to store instructions for the generator's operation. The memory 614 may be part of the power driver 620. The memory 614 may take the form of EEPROM and/or FLASH memory. The memory 614 may store firmware or software code that includes instructions which, when executed by controller 610, cause the controller 610 to perform various functions that are described in this disclosure.

In some embodiments, the generator 600 may include a clock 616, such as a real-time clock (RTC), which is used to provide a time tag to any data stored in the memory 614. This permits specific cases to be identified without knowledge of patient details. Complexity in the inclusion and use of an RTC in a medical instrument primarily relates to the setting and maintenance of time. Two issues are involved: Power and Drift. In terms of power, a battery is commonly used to keep the clock operating when the instrument is not attached to line power. A battery has a finite life before it needs to be replaced, independent of whether it is rechargeable or a primary cell. Although this finite life is in the span of years, consideration is given to both the maintenance of the battery and the correct operation of the generator should the RTC fail due to lack of battery power. In some embodiments, a super-capacitor may be used instead of a battery. A super-capacitor will not need replacement, but it does require more frequent re-connection to line power to ensure that the knowledge of real-time is preserved. The second RTC issue is time drift. Similar to an unsynchronized real-time system, the knowledge of real-time becomes progressively worse with time. Periodic re-setting of the time is required to ensure that accuracy is maintained. A practical solution is to re-synchronize the RTC from web-derived time whenever the generator is attached to a web-enabled device.

In some embodiments, a catheter 155 may include electrodes that are divisible by subsets of four or five. The architecture of generator 600 may be modularized into units driving four or five electrodes per module. In some embodiments, such type of power driver 620 may be referred to as a quadruple/quintuple power driver (QQPD), although the numbers four or five are used as examples only and other numbers per driver are also possible in various embodiments. Each of the power drivers 620 may take the form of a single Printed Circuit Board Assembly (PCBA) which plugs into the motherboard which can accommodate multiple power drivers 620. For example, a power driver 620 may be connected to the motherboard through a pair of PCI-EX connectors, one for the line-isolated signals and one for the patient-isolated signals. This architecture makes the power driver 620 the fundamental building block of the generator 600 which can be operated and fully tested independently of the rest of the electronics. Additional power driver 620 may be added to a generator 600.

The signals may be appropriately buffered to ensure that signal integrity is maintained even when the full board set of power drivers 620 is loaded in the card cages. Sufficient pins may be allocated for power signals to ensure insignificant losses through the connector interface.

A power driver 620 may generate ablation currents each at a targeted form, frequency and phase and deliver the currents to the electrodes that are connected to the power driver 620. The current may be in AC form. In some embodiments, the power driver 620 has circuitry and filters that convert the AC to have a monochromatic frequency. In some embodiments, the frequency of the alternating current is higher than 100 kHz. In some embodiments, the frequency of the alternating current is higher than 150 kHz. In some embodiments, the frequency of the alternating current is higher than 200 kHz.

In some embodiments, the power drivers 620 are synchronous so that the alternating current measurements are made with fixed, synchronous stimulus on all channels. With this in mind, in some embodiments the motherboard will provide a suitably buffered master clock (nominally at 24 MHZ) to the controller 610 and the card slots. Suitable clocks are generated from this master clock, either by division or using the microcontroller integrated phase-locked loop (PLL) synthesizers. An additional synchronization signal (QSYNC) may be provided by the motherboard, to permit division-based synthesizers (such as the H-bridge drives) to be synchronized.

A power driver 620 may be connected to multiple mapping outputs 626, ablation ports 622, and voltage sensors 624. Each set of a mapping output 626, ablation port 622, and voltage sensor 624 may be connected to an electrode of the catheter 155. The various inputs and outputs from different power drivers 620 may be serialized and may be packaged as in a physical connector (e.g., a connector with multiple pins) that can be used to be connected to the catheter 155. A mapping output 626 is used to carry a signal regarding ECG biosignal to a separate or integrated mapping system or to route a pacing current stimulus from the integrated or separate mapping system to a particular electrode. An ablation port 622 is configured to be connected to a conductive wire (e.g., the first conductive wire 444 in FIG. 4A) of an electrode of the catheter 155 to deliver a current to the electrode to generate ablation energy for the treatment of a biological tissue. The generator 600 may include multiple power drivers 620 that are capable of generating different currents and delivering the currents respectively to different electrodes of the catheter 155. For example, in some embodiments, the generator 600 includes a first power driver 620 that has a first ablation port 622 that is configured to be connected to the first wire of a first electrode of the catheter 155 to deliver a first current to the first electrode to generate first ablation energy for treatment of a biological tissue. The generator 600 also includes a second power driver 620 that has a second ablation port 622 that is configured to be connected to a second wire of a second electrode of the catheter 155 to deliver a second current to the second electrode to generate second ablation energy for treatment of the biological tissue. In FIG. 6, the generator 600 is illustrated as having a third power driver 620 to the N-th power driver 620. Within each power driver 620, there can be multiple power and signal regulation circuits so that individualized outputs can be generated. For example, each power driver 620 may have 4 or 5 ablation ports 622, voltage sensors 624, and mapping outputs 626.

A voltage sensor 624 may be used to measure thermocouple voltage corresponding to a wire and a junction of an electrode at the catheter 155. For example, a voltage sensor 624 may measure the thermocouple voltage at the junction 446 illustrated in FIG. 4A. The measured thermocouple voltage may be converted to a temperature reading. Each power driver 620 may have multiple voltage sensors 624 so that the temperature of the electrodes connected to the power driver 620 may be independently measured. For example, the generator 600 may include a first voltage sensor 624 configured to measure the first thermocouple voltage corresponding to the first wire of a first electrode at the catheter 155. The generator 600 may include a second voltage sensor 624 configured to measure a second thermocouple voltage corresponding to a second wire of a second electrode at the catheter 155. The controller 610 may be configured, such as through firmware, to determine a first temperature corresponding to the first electrode based on the first thermocouple voltage and a second temperature corresponding to the second electrode based on the second thermocouple voltage. Additional voltage sensors 624 may also be present in the generator 600 to measure temperature at different electrodes.

In some embodiments, the voltage sensors 624 may also be used as part of an electrical data acquisition system, such as by re-tasking portions of the multichannel thermocouple measurement system which has similar sensitivity and bandwidth. The electrical data may be used to determine the directionality of a source of abnormal rhythm or may be used to detect ECG. In some embodiments, each power driver channel may re-purpose the thermocouple signal conditioning and digitization system to be used as an electro-physiological mapping system. This is feasible because both the gain and the bandwidths required are very similar for the conversion of ECG and thermocouple signals. In some embodiments, each card slot may provide five patient-isolated mapping outputs to the motherboard. These outputs are routed on the motherboard to a single patient-isolated connector and provided to the operator through the back panel interface for conversion using an external data acquisition system.

In some embodiments, voltage sensors 624 may take the form of shared cold junction sensor amplifier(s). A cold junction sensor (CJS) may perform accurate absolute measurements with a thermocouple system and may be located at an electrode. A thermocouple produces a voltage signal which is a function of the difference in temperature between the two ends of the thermocouple. The distal end is typically called the "hot" junction and the proximal end is the "cold" junction. To measure the temperature of the electrode, the temperature of the cold junction is measured and added to the difference. The CJS may take the form of a semiconductor device. In some embodiments, multiple cold junctions can be maintained at the same temperature. A single CJS may be shared for multiple channels. This is called iso-thermal design and certain form of iso-thermal plate is used for this purpose. The iso-thermal plate may take the form of a dedicated copper area on a printed circuit board (PCB) that is isolated from heat flow so that the plate has no significant thermal gradient. A more significant issue is the transition in metallurgies within the catheter 155 itself. Some embodiments use a Type T thermocouple (Constantan-Copper) for this design and at some proximal point in the catheter/cabling the wires will interchange to copper. Other metal combinations may also be possible, such as the combination of Iron, Platinum, Nickel Chromium Alloy, or Nickel Aluminum Alloy, by way of example. The proximal transition is the cold junction and although the CJS may not be placed exactly at this point, there needs to be an accurately predictable (or zero) temperature difference between this proximal transition and the temperature at the CJS. Intermediate transitions in metallurgy can be included in the design provided it is ensured that both wires of the intermediate material are made of the same material which ensures that they do not form a parasitic thermocouple. This commonly occurs at the connectors where it is inconvenient to carry the constantan through continuously. The cold junction may be placed at the front panel of the RF Generator or some convenient intermediate point between the probe tip and the front panel of the RF Generator. The absolute temperature of the Cold Junction may be measured to convert the differential temperature indicated by the thermocouple into absolute temperature. This is performed by an accurate absolute temperature measurement device such as a Resistive Temperature Device (RTD), a temperature indicating semiconductor diode or integrated circuit or any other precision temperature measurement device. An Iso-Thermal plate may be used to ensure that there is tight thermal coupling between the thermocouple pins and the aforesaid precision absolute temperature measurement device, so that the absolute temperature of the probe-tip (hot) junction can be precisely determined. In some cases, there is also a reasonably substantial electrical coupling between these lines. This means there is a substantial amount of 400 kHz AC coupled into the Cold Junction Amplifier. For this reason, in some embodiments, a current mode RTD amplifier is used to condition the RTD signal instead of a Wheatstone bridge design commonly used to serve this purpose. Since the amplifier works in current mode large filtration capacitors can be used to reject the coupled AC on the RTD signal without posing stability problems for the amplifiers.

In some embodiments, the temperature sensor used to measure the absolute temperature of the intermediate cold junction is a simple additional thermocouple.

The generator 600 also includes a power supply 650 that supplies alternating current. The alternating current line power may be converted to a line isolated direct current (DC) power (e.g., 54-volt direct current). The power supply 650 may be a medical-grade power supply, such as a power supply that is qualified for IEC-60601. The DC power may be supplied to the power drivers 620 to be converted to alternating currents in the target forms, frequencies, and phases. In some embodiments, 54 VDC Power is derived from power supply 650 and it is both fused and inrush limited. This power is then distributed to each power driver 620 using ample pins to ensure insignificant loss in the connector interface. The incoming power is converted to the line-isolated master supplies of 12 VDC, 5 VDC, 3.3 VDC, and −5 VDC using high-efficiency buck regulators. These supplies are distributed throughout the motherboard and to the power drivers 620.

In some embodiments, a single shared isolated DC-DC Converter is used to provide operating power to the patient isolated area. In some embodiments, some power is required on the patient side. As with digital isolators, these part(s) must be certified to comply with the appropriate standards. This isolating DC-DC converter produces a high current raw 5 volt patient isolated supply which is used to generate all the other patient isolated power supplies. A simple LDO regulator is used to generate the PI 5 Volt Power supply which has a set point below +5V (4.65 Volts nominally). Switching power supplies (typically switched capacitors) are used to generate the auxiliary supplies of +2.5V.

In some embodiments, the generator 600 may be divided into a few power-isolated areas, such as an operator-isolated area 660, a line isolated area 662, and a patient isolated area 664. In some embodiments, the power for the operator isolated area 660 may be derived from an external power source, such as an incoming USB power provided at the external device interface 648. In some embodiments, the power for the line isolated area 662 may be derived from a motherboard 3.3V supply. A second level of patient isolation may be provided on the motherboard using appropriate digital isolators and a voltage-isolated power converter. The patient isolated area 664 on a power driver 620 may be provided by appropriate digital isolators and appropriate isolated power and signal transformers. In some embodiments, certain clearances may be maintained between any two power-isolated areas. For example, IEC-60601 creep clearances (7 mm) may be used to isolate the areas. The architecture may provide two layers of isolation to both the operator and the patient.

Various front-end components may be configured to communicate with the controller 610. The front-end components may include a front panel display 640 that displays signals, readings, and other information of the generator 600. A control interface 642 may receive inputs from an operator to control the generator 600. The user inputs may take the form of a combination of front panel switches and or foot switches. The generator 600 may also include various indicators to provide signals and warnings to an operator, such as the audio sub-system 644 and the status indicators 646. The generator 600 may provide some forms of audio for the provision of warning and operational tones. Additionally, or alternatively, status and warning LED indicators may also be provided for the indication of simple states such as AC on, Power on, and Error Status. The generator 600 may also include an external device interface 648 to allow the generator 600 to be connected to an external computing device for communication with an external computing device. The external device interface 648 may be wired (e.g., a USB interface) or wireless (e.g., Wi-Fi or Bluetooth). The communication with an external computing device may also be the external device to control the generator 600 or to supplement the functions of the generator 600. For example, in some embodiments, the external computing device may include more complex algorithms such as machine learning models, directionality determination algorithms, and other automatic signal processing and regulation algorithms that may be used to analyze the signals captured by the catheter 155 and provide automated controls or suggestions to the operator or directly to the generator 600.

In some embodiments, a generator 600 may include a front panel display 640. The front panel display 640 may take the form of integrated components. Several components could be selected and generally offer one or more types of communications interface which range from simple serial port interfaces to high-speed USB. Size, shape, pixel counts, speed, luminance, and touchscreen interfacing may be selected appropriately.

In some embodiments, a generator 600 may include a control interface 642 that has an electronic interface design. The operator control interface may involve front panel and foot switches ranging in all kinds of shapes sizes and weights. The same flexible design approach is recommended for the electronics associated with this sub-system and will be apparent to anyone skilled in the art.

In some embodiments, a generator 600 may include an audio sub-system 644 ranging from simple square-wave tone generators to sophisticated multi-channel music synthesizers capable of playing recorded songs. The audio sub-system 644 may be in compliance with the requirements of IEC/EN-60601 regarding the audibility of error tones and warnings. In some embodiments, the audio sub-system 644 meets the amplitude requirements of such specification.

In some embodiments, a generator 600 may include a status indicator 646. The status indicators 646 may take the form of dedicated indicators, typically LEDs to provide primitive status of a handful of variables. Some example uses include power indicator-often multicolored and built into the on/off switch, RF active indicator, and fatal fault indicator. In some embodiments, these status indicators are fundamental and continuously indicated, even in the presence of a system fault severe enough to impair the operation of the front panel display 640, the controller 610, and/or the communications mechanism driving the display sub-system. For this reason, the detailed design of the status indicator electronics is chosen to be as simple and independent as possible. The actual indicators can be individual components or integrated into a front panel overlay.

In some embodiments, the mother includes an external device interface 648 such as a USB-connected remote interface providing both data and control functions for operation, testing, and calibration. The external device interface 648 may be isolated from the line isolated area 662 using digital isolators. DC Power for the operator isolated area 660 can be derived from the incoming USB power, which has the advantage of keeping the interface in a connected state even when the ACG power is switched off.

In some embodiments, a power driver program maintenance system is included to simplify the logistics of firmware revision control in the multiplicity of microcontrollers in the system. Three lines QPGCn, QPGDn and nQMCLRn are provided on each slot to enable controller 610 to download the entire firmware set into each of the power driver supervisory microcontroller (SM). The pins are connected to a suitable programming port on the power driver and to suitable I/Os on the controller 610. A similar programming system permits the power driver SM to program each of the five-channel controllers on each of the power drivers. It is intended that the entire firmware set for the product is included in each controller 610 Software release. A non-volatile firmware version control system permits the controller 610 to determine the release version of each of the SMs. Upon startup, the controller 610 interrogates each SM on each power driver to determine whether the SM is running a compatible firmware release. In the instance where the SM firmware is out of date, the controller 610 simply upgrades the SM to the version that is encapsulated in its firmware release. A similar maintenance system for the channel controllers is incorporated into the SM firmware release, ensuring that the product is always running compatible firmware on all processors. Each SM will be provided with ample program memory to store both its own application program and an image of the channel controllers application program. Similarly, the controller 610 is provided with enough program memory to store all three applications.

In some embodiments, the analog supplies and references are provided with suitable potential dividers to permit the controller 610 to assess whether they are within an operational range determined from worst-case component tolerances. Clock signals are measured relative to the auxiliary clock reference at a targeted frequency (e.g., 32.768 kHz) and limited tested. Wherever possible, these measurements are performed continuously within a periodic self-health monitor. In some cases, the measurements are performed within a Power-On Self-Test (POST) routine.

Example Power Driver

Figure 7A:
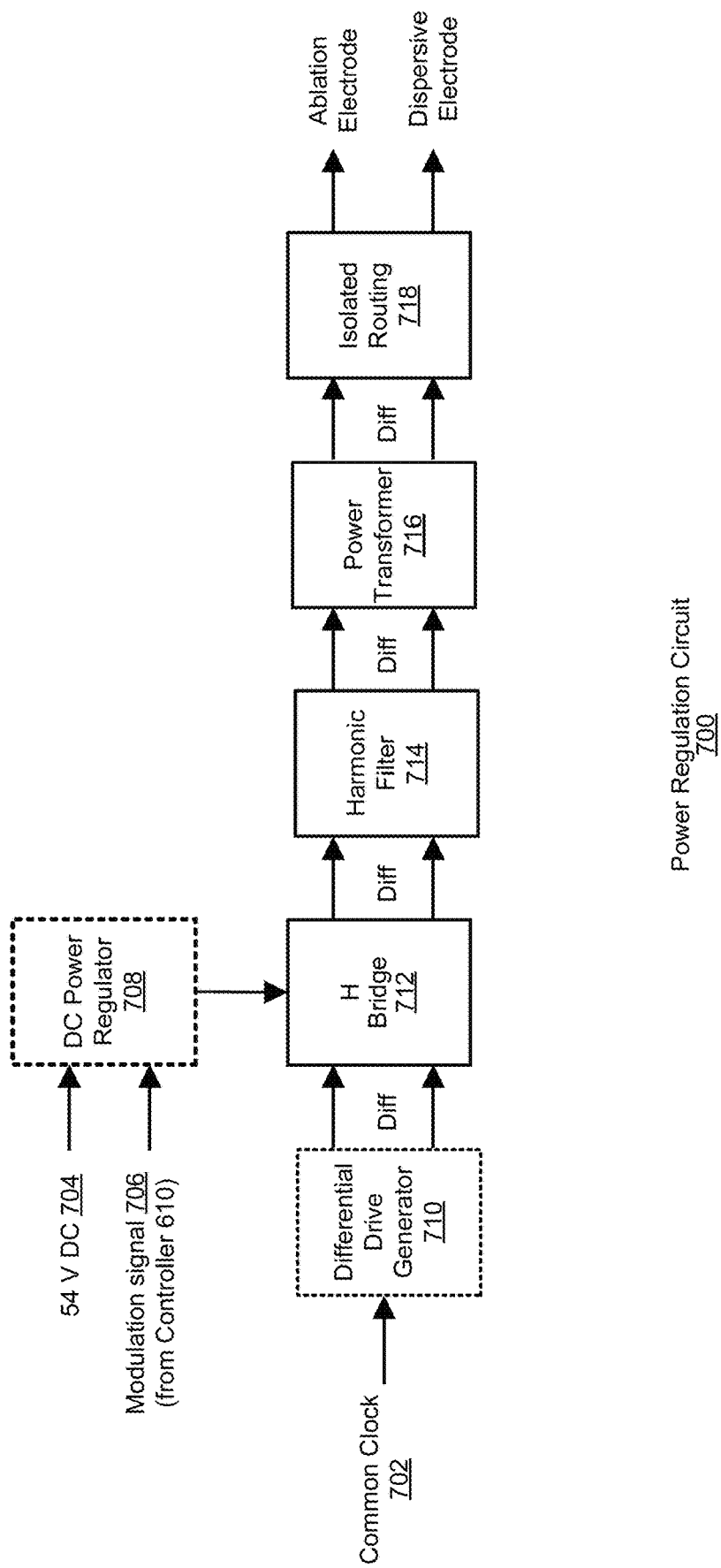
FIG. 7A is a block diagram illustrating an example power regulation circuit of a power driver, in accordance with some embodiments.

FIG. 7A is a block diagram illustrating an example power regulation circuit 700 of a power driver 620, in accordance with some embodiments. Each power regulation circuit 700 may be referred to as a synchronous monochromatic AC generator circuit. A power driver 620 may be connected to multiple electrodes whose ablation currents are individually regulated. The individual regulation of ablation currents may be achieved through various designs. For example, in some embodiments, a power driver 620 may include multiple sets of power regulation circuits 700 that are synchronized. In other embodiments, the electrodes may share a power regulation circuit 700 and multiplexing techniques are used. For example, time division multiplexing, frequency division multiplexing, or another suitable multiplexing technique may be used. In some embodiments, since the radiofrequency (RF) power requirement at each electrode can be relatively low (e.g., no more than 10 watts), a dedicated power regulation circuit 700 may be used over a multiplexed architecture due to the complexities of multiplexing the RF power, temperature sensing, and electrical monitoring signals. The multiplicity of power regulation circuit 700 may share a common clock 702 so that AC parameter measurements are synchronous with respect to the common clock 702.

An alternating current used to deliver the ablation energy may be generated in various ways. In some embodiments, the AC is generated using a direct current 704 and a modulation signal 706 at a DC power regulator 708. The direct current 704 may be received from the power supply 650 illustrated in FIG. 6 and the modulation signal 706 may be received from the controller 610. The modulation signal 706 may be a pulse-width modulation signal or any suitable modulation signal. In some embodiments, the AC is generated using a differential drive generator 710. An alternating switch circuit, such as an H-bridge 712, is used to switch the polarity of the current to generate the waveform of the AC current. In some embodiments, the AC current generated can be above 10 volts and analog filters are used instead of digital filters.

A harmonic filter 714 is located downstream of the alternating switch circuit that generates the AC to filter the AC at a particular target frequency. Conventionally, AC generators have significant harmonic content in their output because the architecture of AC generators can be similar to a generic switched-mode power supply. This yields a design where generating AC power is relatively simple but measuring AC power (and other AC parameters) is complex. For example, the measurement of AC power requires the accurate multiplication of instantaneous AC voltage by current with a bandwidth that includes the fundamental frequency and all harmonics at which significant energy is being delivered. Such measurement would involve a significant amount of specialized digital and/or analog hardware. In some embodiments, AC energy is filtered to a monochromatic current (single frequency) by the harmonic filter 714 so that measurement issues are greatly reduced.

In some embodiments, a monochromatic AC signal is derived from a square wave generator filtered of harmonics using a harmonic filter 714. The harmonic filter 714 permits the creation of the monochromatic power drive. Presuming a square wave drive, both the efficiency of conversion and the ability to calculate AC parameters from simple measurements are dependent on the performance of the harmonic filter 714, which may serve as a differential square wave to sine wave converter. The harmonic filter 714 is configured to generate a clean, low harmonic content sine wave output to the AC power transformer 716. Harmonic energy content is further efficiently filtered by the AC power transformer 716, which is optimized at the fundamental frequency. In some embodiments, a square wave power drive circuit, which includes the H-bridge 712, is used to generate the AC to remove even harmonics. By using a square wave power drive devoid of even harmonics, the harmonic filter 714 needs only filter signals at odd harmonic frequencies, simplifying the architecture and enhancing performance.

In some embodiments, the AC generated at a square wave drive circuit has only odd harmonics with normalized amplitudes of $$\frac{4}{\pi}, \frac{4}{3\pi}, \frac{4}{5\pi}, \ldots.$$

These coefficients disregard other frequency limiting elements, notably the non-zero output impedance and finite rise and fall times of the H-Bridge generator. Consequently, actual high-frequency energy, particularly at the higher harmonics will be considerably lower than the Fourier coefficients. This makes the performance insensitive to component tolerances so that it can be realized with inexpensive parts and, in some cases, does not require tuning of any kind.

Figure 7B:
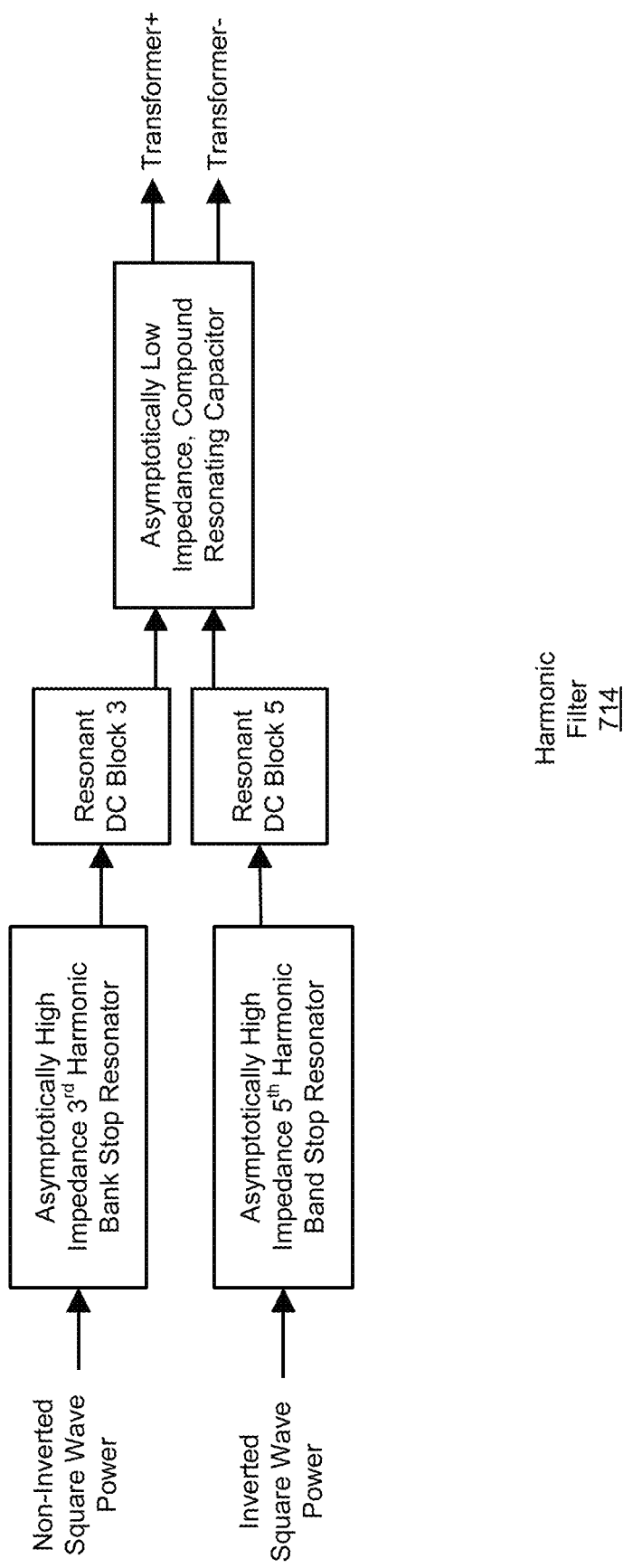
FIG. 7B is a block diagram illustrating an example architecture of a harmonic filter, in accordance with some embodiments.
Figure 7C:
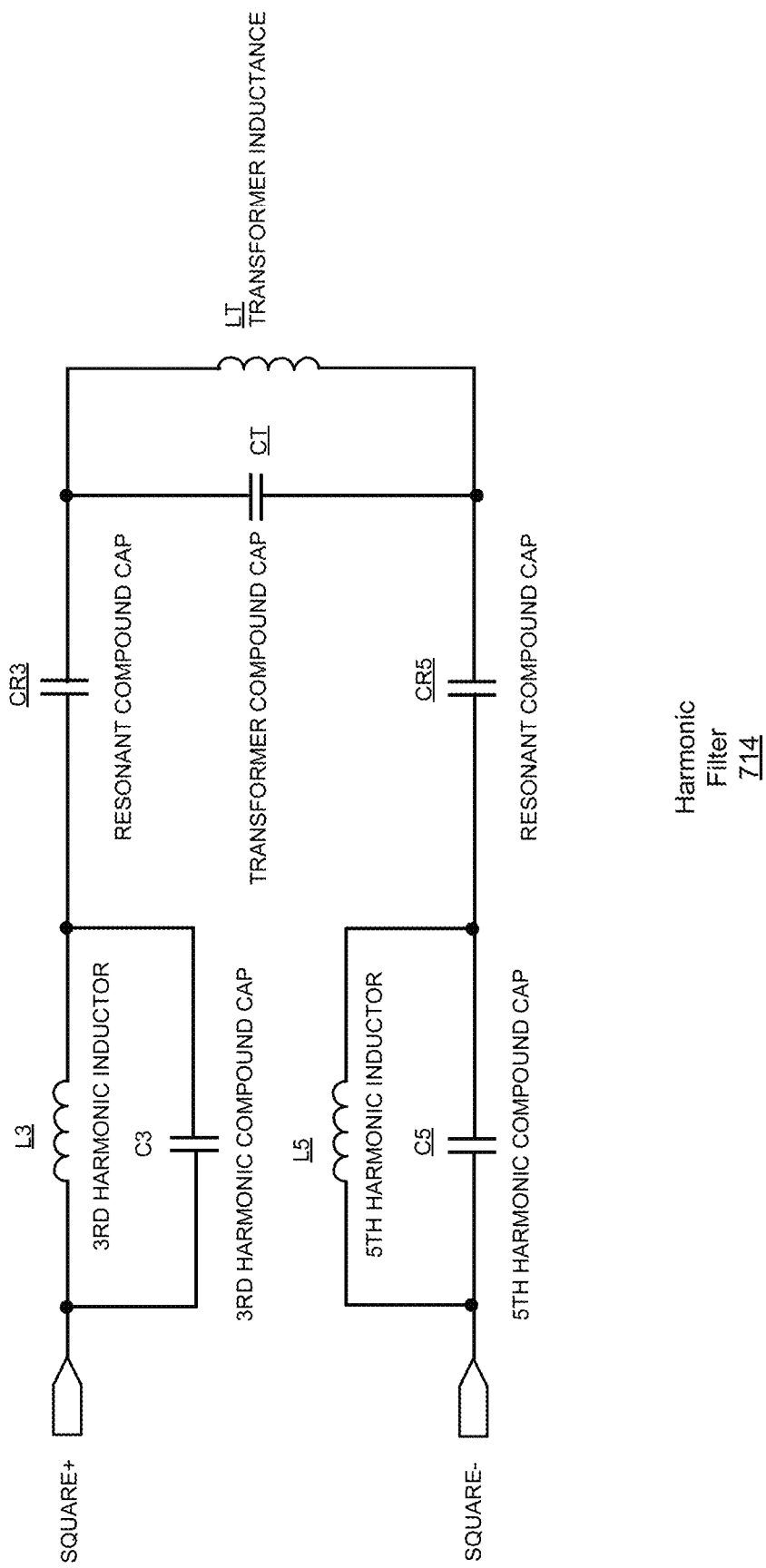
FIG. 7C is an example schematic of the harmonic filter, in accordance with some embodiments.

FIG. 7B is a block diagram illustrating an example architecture of a harmonic filter 714, in accordance with some embodiments. FIG. 7C is an example schematic of the harmonic filter 714, in accordance with some embodiments. The harmonic filter 714 may include one or more tank circuits that include one or more capacitors and one or more inductors to create filters at targeted frequencies. A design objective of the harmonic filter 714 is to present a high impedance and/or attenuation at all odd harmonics of the fundamental square wave AC power source. Since the system is differential in nature, the harmonic filter 714 may include two or more band-stop filters at various odd harmonics, such as at the $3^{rd}$ and $5^{th}$ harmonics. The harmonic filter 714 may reject all odd harmonics. By way of example illustrated in FIG. 7C, an objective is to make a tank circuit that includes a transformer compound capacitor CT and a transformer inductor LT (transformer magnetizing inductance, shown in FIG. 7C) resonant at the 400 kHz fundamental frequency, so that the tank circuit presents a high impedance at this frequency, and to block the $3^{rd}$ and $5^{th}$ harmonic frequencies with the band-stop filters. Compound capacitors are created by parallel combinations of common values of capacitance.

While compound filters can yield good performance in theory, such filters may require unrealizable designs. This is because compound filters may need unreasonably precise component values and unreasonably high Q Factors, especially since the design requires 8 reactive elements plus the variable, complex load impedance. In some embodiments, as a solution, a practical technique was developed that generates readily achievable designs that are tolerant to component value tolerances. By way of example, the principle tuning is the compound capacitor across the transformer magnetizing inductance which is tuned to the fundamental frequency, 400 kHz. For a given transformer magnetizing inductance LT:

$$C_T = \frac{1}{4\pi^2 f^2 L_T}, \; f = 400 \text{ kHz}$$

which has a characteristic impedance $Z_{TANK}$ given by:

$$Z_{TANK} = \sqrt{\frac{L_T}{C_p}} = 2\pi f L_T, \; f = 400 \text{ kHz}$$

At the resonant frequency, a capacitor and a transformer magnetizing inductor form a high-impedance tank circuit where large alternating currents circulate naturally, thereby exchanging stored energy in the inductor with stored energy in the capacitor at the resonant frequency. The impedance presented to the driver is, however, an asymptotically infinite impedance in the absence of load and loss. When a load is added, the driver sees merely the (transformed) impedance of the load. If the tank were connected directly to the square wave drive, a low efficiency would be experienced. This is because, at frequencies above the primary resonance, the tank presents a low capacitive impedance to the driver, so the driver would circulate large harmonic currents through this low-impedance capacitor.

The design principle for these higher harmonics starts by looking at the frequency asymptote (well above the fundamental, such as f*10 or around 4 MHz) where the resonators (fundamental, 3rd harmonic band-stop, and $5^{th}$ harmonic band-stop) have impedances primarily defined by their capacitive components, as all the inductive components have high impedance. Harmonic rejection at these asymptotic frequencies is defined by the simple capacitive voltage divider formed by the transformer coil resonating capacitor CT and the series combination of the $3^{rd}$ harmonic capacitor C3 in series with the DC block capacitors CR3 and CR5 in series with the $5^{th}$ harmonic capacitor C5, as illustrated in FIG. 7C. In some embodiments, the minimum asymptotic harmonic rejection is set above 20 dB, reducing the harmonic energy for the harmonic numbers above 7 by at least a factor of 100. This yields a condition:

$$\frac{1}{C_5} + \frac{1}{C_3} + \frac{1}{C_{R3}} + \frac{1}{C_{R5}} > \frac{10}{C_T}$$

In some embodiments, a symmetrical square wave drive is used. As such, the generated AC with harmonics are at odd multiples of the fundamental frequency, the largest being the $3^{rd}$ harmonic, the next being the $5^{th}$ harmonic, and so on. Two band-stop filters are included in the design, one in each arm of the tank circuit. These band-stop filters provide two functions: first, to provide a high rejection at the center frequency (through high effective impedance); second, to provide an asymptotically high relative impedance to frequencies above their center frequency(s). In the asymptote, the architecture of FIG. 7C becomes a capacitive divider. The inductors in FIG. 7C in parallel with harmonic capacitors may be disregarded as the indicators are associated with a high or close to infinite impedance. An objective is that C3 and C5 should be small values of capacitance and CT should be a large capacitance so that the division ratio is large, giving high asymptotic rejection. Small values of C3 and C5 require large values of inductance for L3 and L5 to achieve the correct resonant frequencies. The design may be achieved within the context of realistic tolerances and Q factors for the components. In some embodiments, L3 and L5 are chosen iteratively from available values and an evaluation of the completed design is performed. C3 may be chosen to resonate at the $3^{rd}$ harmonic. C5 may be chosen to resonate at the $5^{th}$ harmonic. For example, $$C_3 = \frac{1}{36\pi^2 f^2 L_3}, \; f = 400 \text{ kHz}$$

$$C_5 = \frac{1}{100\pi^2 f^2 L_5}, \; f = 400 \text{ kHz}$$

In some embodiments, a design spreadsheet may be constructed to additionally perform a compensation for the self-resonance of L3 and L5, but such self-resonance may be small and can be ignored for the purposes of explanation. Below their resonances (at 1.2 MHz and 2 MHz, respectively) the harmonic band-stop filters both look like inductors, because their inductive elements dominate. At the fundamental frequency, f, each band-stop filter presents an excess effective series inductance slightly larger than their nominal values. For example, $$L_{3\textit{eff}} = \frac{9L_3}{8}, \; L_{5\textit{eff}} = \frac{25L_5}{24}$$

Even though these inductances can be combined and compensated for with a single resonating capacitor, it has been found that the loss is minimized when two capacitors CR3 and CR5 are used to individually resonate out the excess inductances $L_{3\textit{eff}}$ and $L_{5\textit{eff}}$ at the fundamental frequency. This is because combining the capacitors requires that the currents pass through the transformer and secondary circuit which increases the effective loss. The resonating capacitors are chosen simply:

$$C_{R3} = \frac{1}{4\pi^2 f^2 L_{3\textit{eff}}}, \; C_{R5} = \frac{1}{4\pi^2 f^2 L_{5\textit{eff}}}, \; f = 400 \text{ kHz}$$

In this way, the full voltage drive may be applied to the tank circuit at the fundamental frequency. While 400 kHz is used as the example value of fundamental frequency, another targeted fundamental frequency may also be used, and the design may be generalized for other targeted frequencies.

In some embodiments, the above design principle may be associated with a theoretical design that needs to be further adjusted using standard 10% tolerance inductors and 1% temperature stable capacitors. A spreadsheet analysis permits component values to be chosen which in the worst case tolerance stack up with the worst case tissue load impedances to meet the harmonic rejection requirements. The spreadsheet optimizes the 32 corner cases of worst-case loads and tolerances and the frequency response is evaluated for each corner case. Worst case response is assessed as the largest amount of attenuation for frequencies below 600 kHz and as the smallest amount of attenuation for frequencies above 600 kHz, always selecting the worst of the 32 corner cases at every frequency. The first step of the process is to optimize the performance to yield the best "worst case" response. After this is performed, the design is rationalized to use actual attainable component values.

Figure 8:
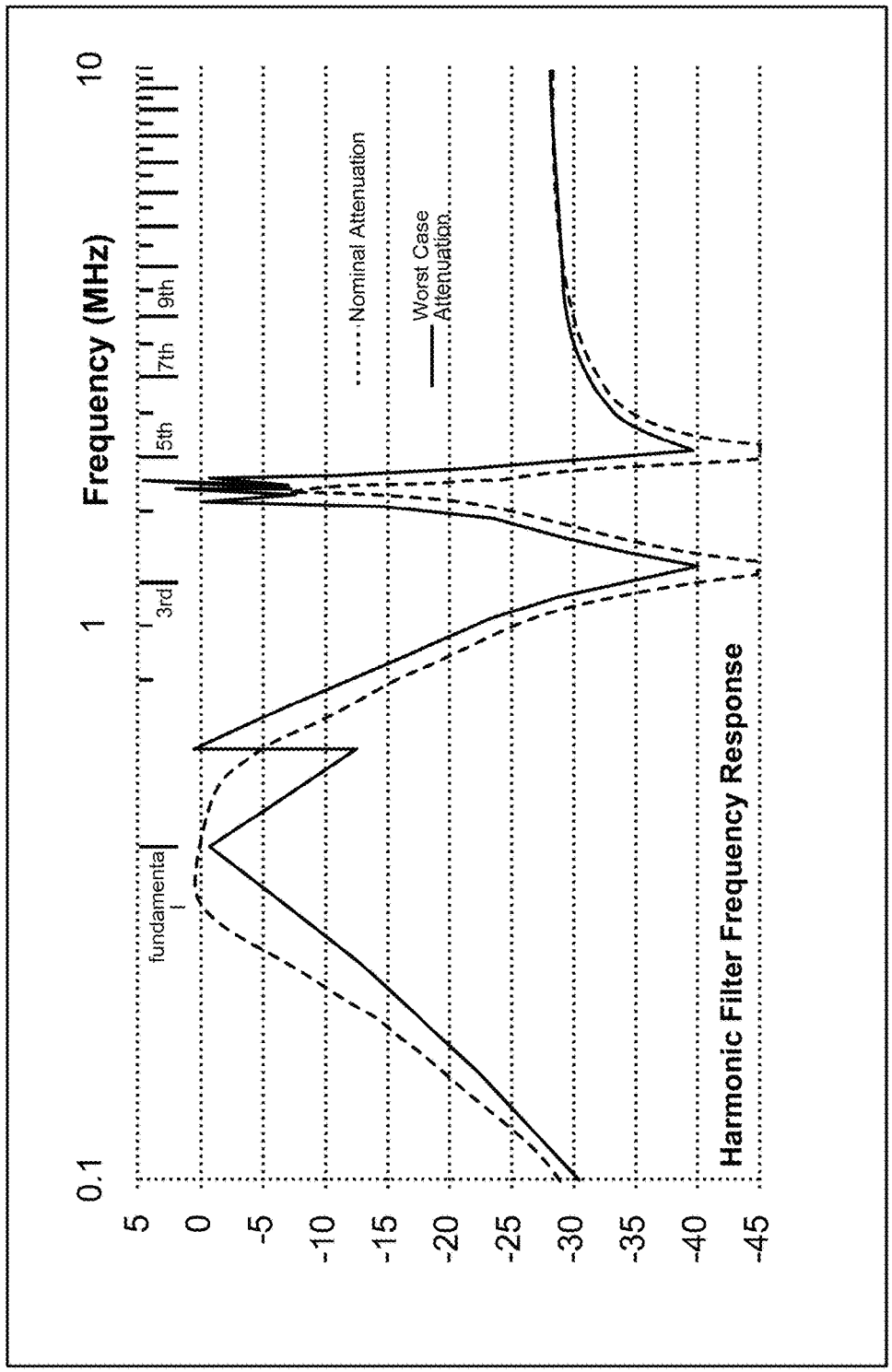
FIG. 8 is a graphical representation of both the nominal response and the best worst-case response in a hormonic filter, in accordance with some embodiments.

FIG. 8 is a graphical representation of both the nominal response and the best worst-case response in a harmonic filter, in accordance with some embodiments.

FIG. 8 indicates, on the x-axis, large markers at the fundamental and odd harmonics, and smaller markers at the even harmonics which are not relevant. The nominal response is shown by a dashed line, and the worst-case response is shown by a solid line. The discontinuity in the worst-case characteristic at 600 kHz may be due to the change in the selection criterion for the worst case (from maximum attenuation to minimum attenuation) at this point. The biased main lobe of the nominal response is because the design was optimized using the specified imbalanced load capacitance range. The optimizer essentially reduces the transformer tank capacitance, CT, to account for the very high maximum load capacitance of 1400 pF. What can be seen is low loss at the fundamental combined with good rejection at all odd harmonics even in the worst-case scenario.

Figure 7D:
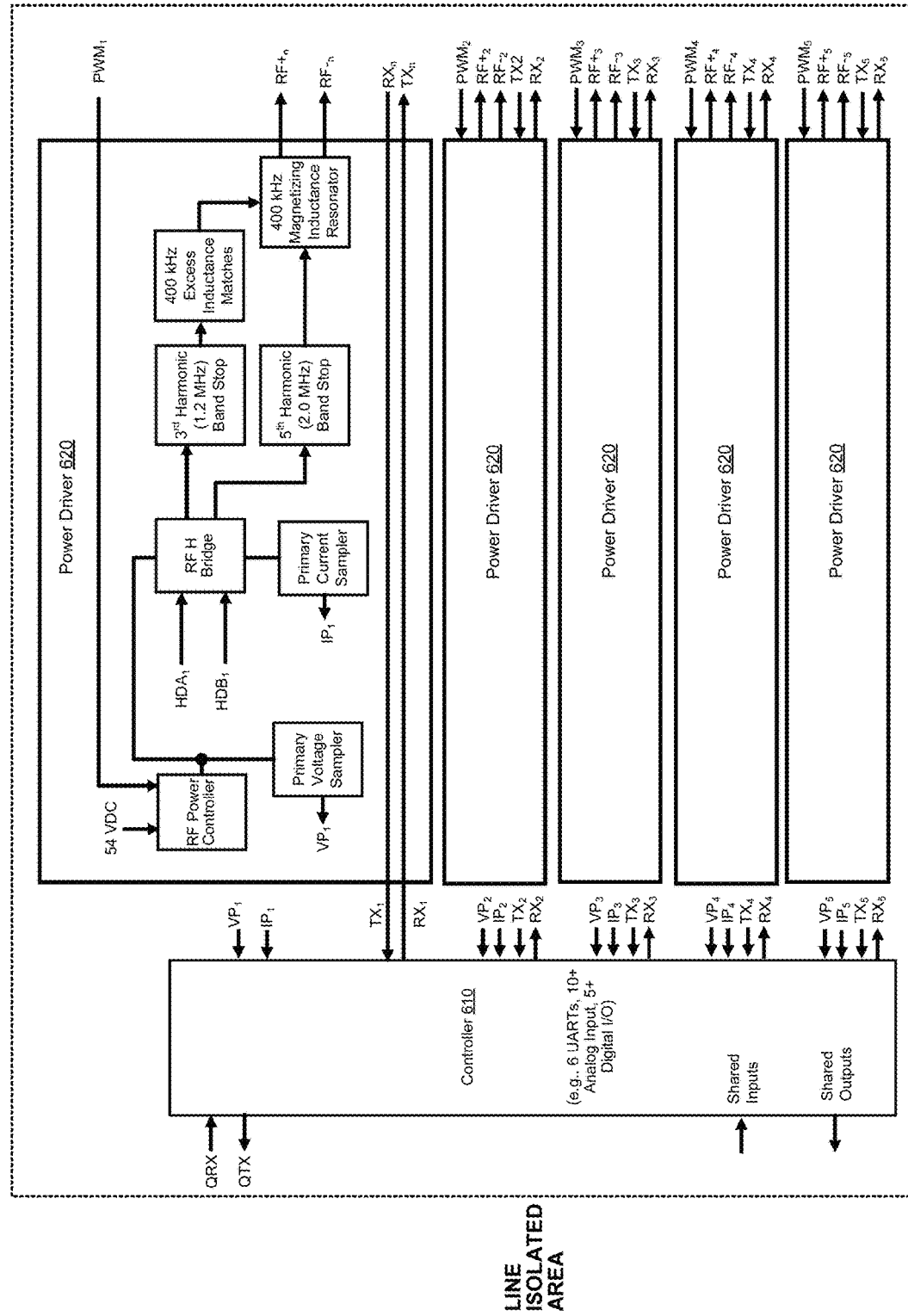
FIG. 7D is a block diagram illustrating a series of power drivers, in accordance with some embodiments.

FIG. 7D is a block diagram illustrating a series of power drivers 620, in accordance with some embodiments. The first power driver 620 illustrates an instance of power regulation circuit 700. Each power driver 620 may include multiple instances (e.g., 4 or 5 in QQPD) of the power regulation circuit 700, and a catheter 155 may include multiple power drivers 620. The power regulation circuit 700 uses a harmonic filter approach. One of the advantages of this harmonic filter approach is that the impedance presented to the driver is fundamentally the transformed AC load in parallel with a small capacitor. The tank impedance is resonated out, at the 3rd harmonic the 3rd harmonic filter resonates to a high impedance, and at the 5th harmonic the 5th harmonic filter resonates to a high impedance. At higher harmonics, the impedance presented to the driver is less than 190 pF (the impedance of the series capacitor chain), which is small compared to the output capacitances of the driver FETs. This permits exceptionally high DC to AC conversion efficiencies which can exceed 85% in practice.

Each power driver 620 may include both unit sub-systems and channel based sub-systems, as illustrated in FIG. 7C. There is a single instance of each unit sub-system on each power driver 620 whereas channel based sub-systems are replicated 5 times on each QQPD.

Figure 7E:
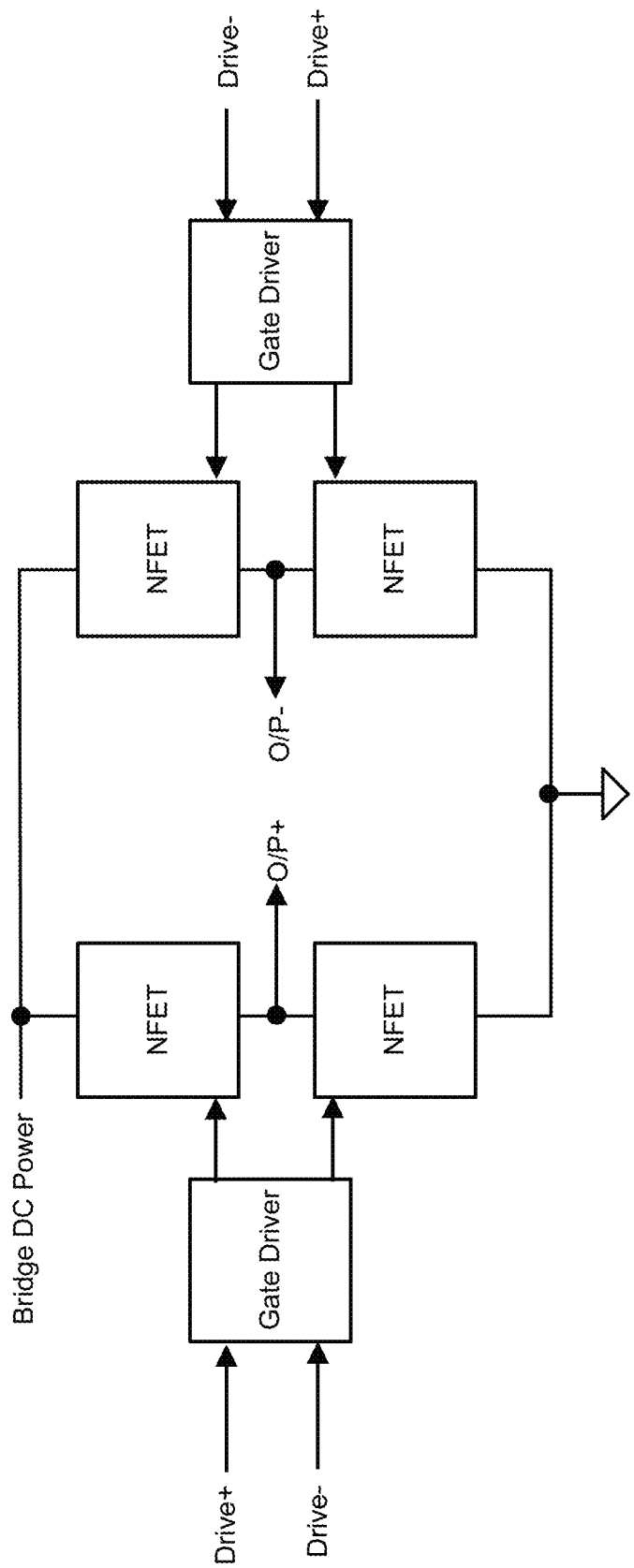
FIG. 7E is a block diagram illustrating an example AC power generation circuit that includes an H-bridge, in accordance with some embodiments.

FIG. 7E is a block diagram illustrating an example AC power generation circuit that includes an H-bridge 712, in accordance with some embodiments. The AC power generation may be implemented in different designs of H-bridge 712. FIG. 7E shows an example H-bridge block diagram, which includes a pair of break-before-make double-throw switches driven in antiphase. In principle, there are no inherently dissipative components in the circuit other than the load resistance R. Thus, at least at low frequencies, high efficiencies approaching 100% are theoretically possible. At practical alternating current frequencies, the efficiencies that can be achieved are limited by parasitic elements in the switch devices themselves, notably parasitic resistance in the switch channels and parasitic capacitances limiting the speed with which the devices will switch. At the switching rate of 400 kHz in several embodiments, very high efficiencies can be achieved with the design. In some embodiments, the AC load resistance (e.g., biological tissue) is toggled between the supplies differentially at the AC Frequency; provided the switches are lossless, the H-Bridge can attain 100% power conversion efficiency. The realization of the concept is significantly more complex due to the following issues:

(1) Any Real impedance in the switches becomes a loss element which dissipates AC energy in the switch elements as heat.
(2) Any complex impedance in the switches reduces the output signal level as it is reflected into a complex effective source impedance.
(3) Slow Rise and Fall times in the switches results in simultaneous voltage and current being present across the switch elements creating dissipative losses in the switches.
(4) The switches must have true break-before-make operation, otherwise simultaneous conduction occurs where current flows through the vertical legs of the "H" dissipating (potentially destructive) energy into the switch elements. Simultaneous conduction is prevented by inserting a programmed "Dead Time" between the break of one switch and the make of the other switch.

In some embodiments, FIG. 7E provides a simplified block diagram. The discrete H-Bridge is constructed of 4 N-channel Power FETs and a pair of FET gate drivers. One of the advantages of the discrete design is that the parts required to construct it are available from multiple vendors and are in common supply. A second advantage is that there is no effective limitation on the bridge voltage which can be used which permits the design to be operated at 54 volts, compliant with a 2:1 turns ratio on the AC output transformer.

Figure 7F:
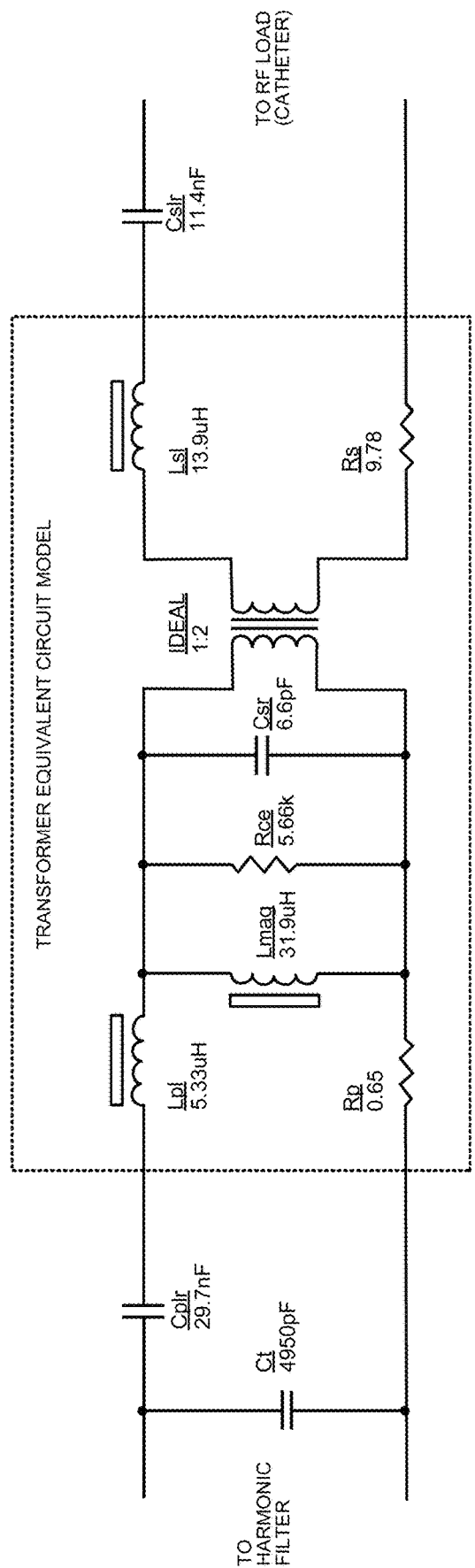
FIG. 7F is a block diagram that illustrates an example of power transformer, in accordance some embodiments.

FIG. 7F is a block diagram that illustrates an example of power transformer 716, in accordance with some embodiments. FIG. 7F illustrates a transformer-equivalent circuit compiled from measured data, the components are shown inside the box in FIG. 7F are the transformer itself and its parasitic elements. The three capacitors Cplr, Cslr and Ct are compensations for the primary leakage inductance, Lpl, the secondary leakage inductance, Lsl, and the magnetizing inductance, Lmag, respectively. In some embodiments, an AC power transformer 716 serves as a monochromatic component that is designed to be low-loss, have the correct turns ratio and meet the isolation and specifications required by IEC-60601 and the European Medical Device Directive (MDD).

Figure 9A:
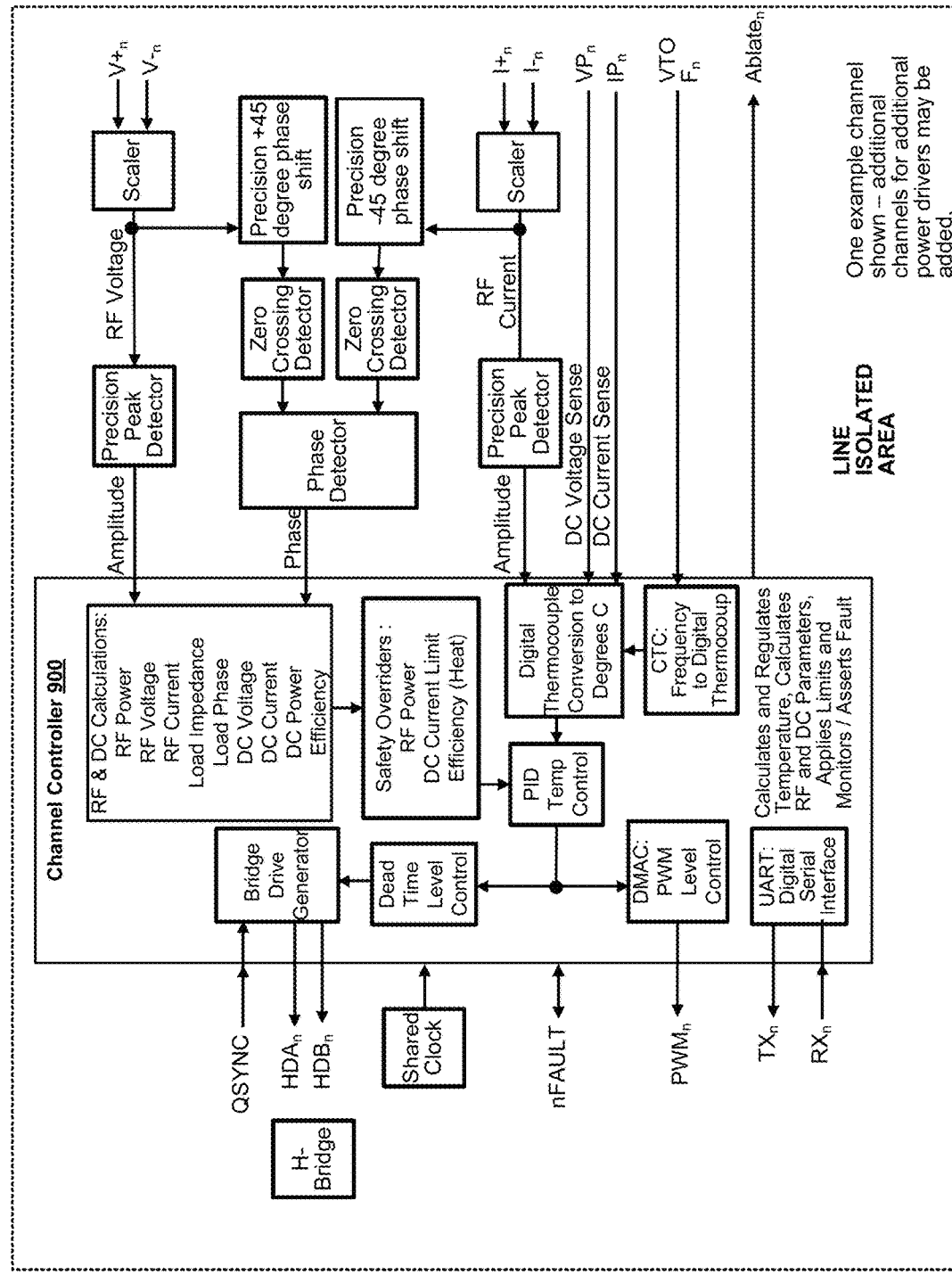
FIG. 9A is a conceptual block diagram illustrating the firmware and signal functional block of an example a channel controller, in accordance with some embodiments.

FIG. 9A is a conceptual block diagram illustrating the firmware and signal functional block of an example a channel controller 900, in accordance with some embodiments. In a catheter 155, a channel may correspond to an electrode or a set of electrodes that are controlled and regulated together. Each channel may be associated with a channel controller 900. A channel controller 900 may be selected as a low-cost, small-footprint microcontroller that has a relatively extensive set of integrated peripherals which eliminate many external components. The functions of a channel controller 900 include calculating and regulating electrode temperature for the channel, making AC and DC measurements, and performing basic safety and protection.

The channel controller 900 may perform one or more features below.

(1) Decoding the digital thermocouple voltage into a digital representation (CTC2)

(2) Transforming the digital thermocouple voltage into an absolute apparent temperature
(3) Correcting the apparent temperature for thermocouple non-linearities to derive the true probe tip temperature;
(4) Regulating the true probe temperature by modulating the AC Power with a PID algorithm.
(5) Creating a pulse width modulation (PWM) drive to regulate the AC Power (CTC)
(6) Enhancing the resolution of the PWM drive using 1-bit dithering (DMAC)
(7) Parsing master microcontroller commands
(8) On demand, returning the probe temperature to the master microcontroller
(9) Converting the analog peak voltage into a digital representation (ADC)
(10) Converting the analog peak current into a digital representation (ADC)
(11) Measuring the Voltage to Current Phase signal (CTC)
(12) Calculating the AC Apparent Power from the Peak Voltage and Peak Current
(13) Calculating the AC True Power from the Apparent Power and the IF phase
(14) Calculating the Load Impedance from the Peak Voltage, Peak Current and Phase
(15) Applying safety limits to the PID based on all AC Parameters
(16) Converting the DC Bridge Voltage (ADC)
(17) Converting the DC Bridge Current (ADC)
(18) Calculating the DC Bridge Power by multiplying DC Voltage by DC Current
(19) Calculating the Conversion efficiency and Power Dissipated in the Bridge
(20) Estimating the Bridge Temperature from the Power Dissipated in the Bridge
(21) Applying safety limits based on estimated Bridge Temperature and Bridge DC Current
(22) On demand, returning the AC parameters to the master microcontroller
(23) Performing Power-On Self Tests (POST)
(24) Performing continuous Self-Health monitoring.

As illustrated in FIG. 9A, in some embodiments, the ablation current sent to the patient is in AC while the detected voltage is DC. The detected voltage is received from the return wire 510 and serves as the voltage reading of the thermocouple at various junctions 446. The DC current received detects the thermocouple voltage at the patient's body and is converted into temperature reading by the controller 900.

In some embodiments, the measurements that may be made at each electrode may include:
(1) ECG Signal amplitude
(2) Pacing sensitivity
(3) RF Impedance amplitude (and derivatives thereof)
(4) RF Impedance Phase (and derivatives thereof)
(5) Absolute Temperature
(6) RF Power Required to maintain target temperature
(7) RF Energy required to achieve target temperature.

In some embodiments, there can be various treatment controls, including but not limited to:
(1) Electrodes selected to be used therapeutically
(2) Target temperatures for each treatment electrode
(3) Impedance limits to apply for each treatment electrode
(4) Power limits to applied for each treatment electrode
(5) Treatment time limits to applied for each treatment electrode
(6) Temperature Ramp Up/Ramp Down profile for each treatment electrode.

In some embodiments, controller 900 may store in the memory code instructions, when executed, cause the controller 900 to perform one or more steps in regulating the level of power delivered to individual electrodes based on a sensed measure that is determined from the DC voltage/impedance. The sensed measure may take the form of a sensed temperature, a sensed impedance, current, pulsed current, frequency, or any suitable measure. In response to the sensed measure of an individual electrode is above a predetermined target range (e.g., N % above or below 70 C), the controller 900 causes a power driver (e.g., power driver 620) to reduce the power supplied to the individual electrode. In response to the sensed measure of an individual electrode is below a predetermined target range, the controller 900 causes the power driver to increase the power supplied to the individual electrode. In some embodiments, each electrode may return its own sensed measure and be individually regulated to a particular target temperature range. The rate of sensing and energy modulation may be performed at a frequency range, such as in 50 kHz, 10 kHz, 1 kHz, 100 Hz, 50 Hz, 10 Hz, 5 Hz, 1 Hz or another suitable frequency. In some embodiments, this rate of sensing and energy modulation may be determined based on the thermal property of the target biological tissue. In some embodiments, the modulation frequency is higher than the thermal time constant frequency of the target biological tissue. In some embodiments, various frequencies used in the system, including the ablation frequency and the energy modulation frequency, may be set at frequencies that are higher than the target biological tissue so that the target biological tissue is not affected by those external frequencies.

In some embodiments, the controller 900 may regulated more than one power drivers that are in communications with multiple electrodes. For example, the treatment system may deploy multiple electrodes, including a first electrode, a second electrode, and so on. The controller 900 may receive DC sense currents from each individual electrode and determine the sensed measures (e.g., temperature) for those electrodes. The controller 900 may regulate the power drivers, such as a first power driver and a second power driver, to maintain the first temperature and the second temperature within a predetermined range of temperature. In some embodiments, the target temperature ranges may be the same across different electrodes or different among the electrodes, depending on the clinical need and the setting of the clinical using the treatment system.

In some embodiments, a predetermined range of temperature may be 2 degrees Celsius above and below a target temperature (e.g., 70 C). In some embodiments, a predetermined range of temperature may be 4 degrees Celsius above and below a target temperature. In some embodiments, a predetermined range of temperature may be 5% above and below a target temperature. In some embodiments, a predetermined range of temperature may be 2% above and below a target temperature. In some embodiments, the root mean square temperature over time may be maintained 2 degrees Celsius above and below a target temperature. In some embodiments, the root mean square temperature over time may be maintained 4 degrees Celsius above and below a target temperature. In some embodiments, the system may have a tolerance range that allows certain transient changes in temperature that is beyond a first predetermined range. For example, in some embodiments, at least 90% of duration of the treatment, the temperature is maintained within 2 degrees Celsius above and below a target temperature. The transient changes in temperature may be maintained within a second predetermined range, which may be 4 degrees Celsius above and below the target temperature. Put differently, in a majority of the duration the temperature is maintained within a first range but any transient spike may still be within a second range. The precise size of the range and the target temperature may be determined clinically based on the target biological tissue and the biological environment to avoid unintended adverse effects such as damaging of other tissues, blood clot, or even boiling of blood. By having temperature sensor for each electrode, the temperature and ablation energy at each electrode may be individually regulated. Conventionally, a catheter may sense at a precise point location, but ablation treatment is performed at a large area, which caused imprecision and damage to the surrounding tissues.

Figure 9B:
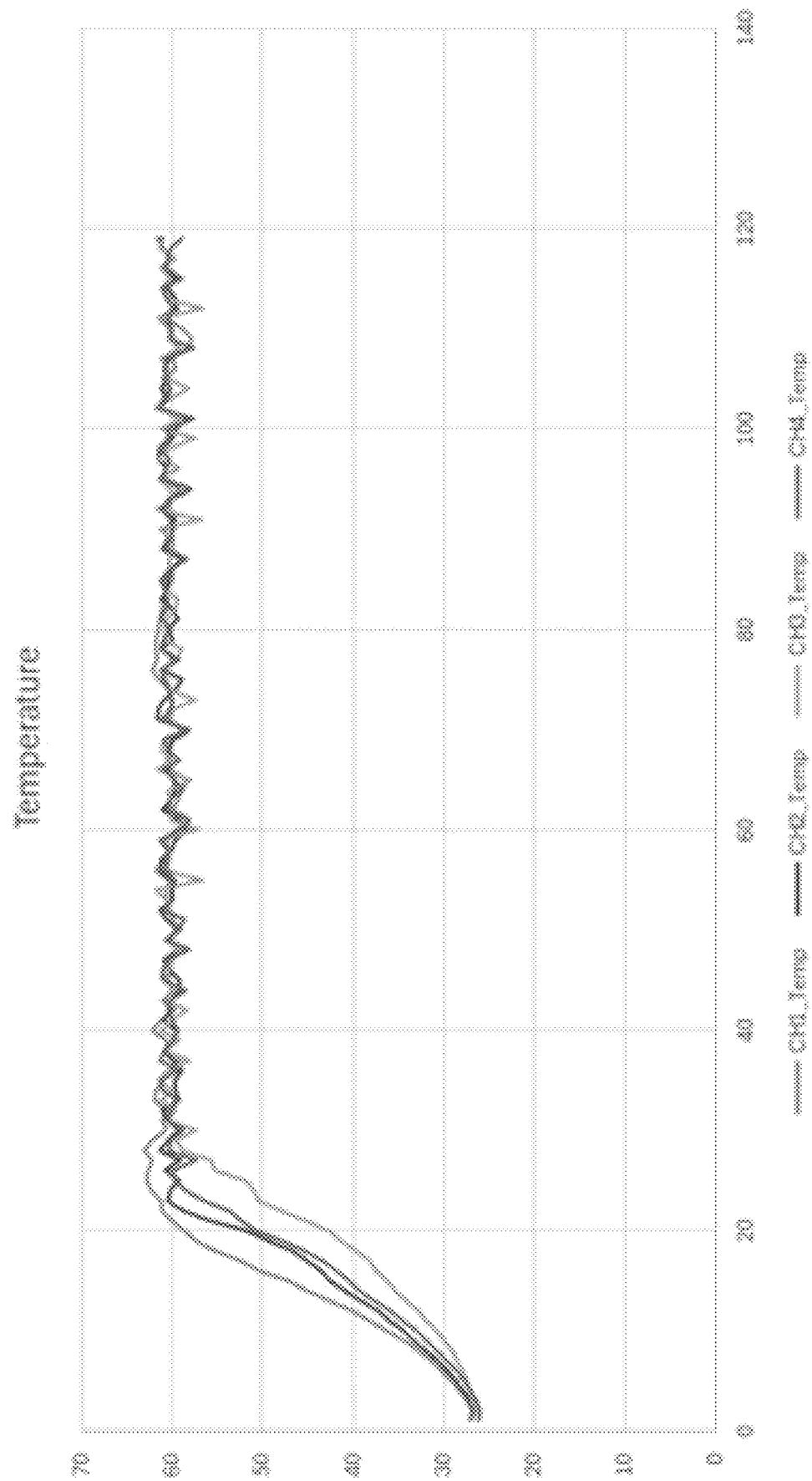
FIG. 9B is a chart illustrating an experimental result of temperature regulation using a treatment system in an animal trial, in accordance with some embodiments.

FIG. 9B is an experimental result of temperature regulation using the treatment system 100 in an animal trial. Ablation energy was delivered to tissue of a live pig and temperatures at different electrodes were measured. As shown in FIG. 9B, after the onset of power, the temperatures at different electrodes can be controlled with a very precise range.

Figure 10:
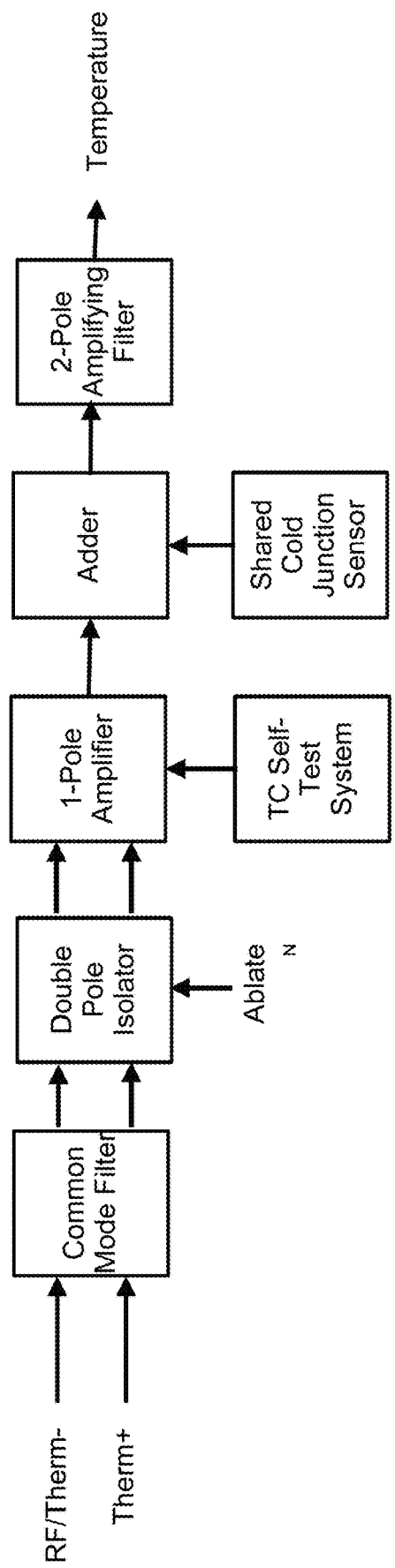
FIG. 10 illustrates a thermocouple signal conditioner, in accordance with some embodiments.

FIG. 10 illustrates a thermocouple signal conditioner 1010, in accordance with some embodiments. The thermocouple signal conditioner 1010 may be part of a voltage sensor 624. From a signal analysis standpoint, the DC component of the input is a differential DC signal with a sensitivity of about 43.2 μV/oC superimposed with a large AC signal at 400 kHz with a common mode component as large as 220 Volts Pk-Pk and a differential signal (due to the catheter wire impedance) as large as 4 Volts Pk-Pk. If the AC interference is to be reduced to 1° C. Pk-Pk, the common mode AC component needs to be attenuated by a minimum of 135 dB and the differential mode AC component needs to be attenuated by more than 100 dB. Achieving this level of attenuation either with a pure passive filter or with a pure active filter in a reproducible and cost-effective manner can be challenging.

In some embodiments, the signal labeled Therm+ in FIG. 10 is derived from the resistively isolated intermediate cold junction located at the electrode of a catheter 155. This Therm+ signal is corrected for any temperature deviation from body temperature using its own embedded absolute temperature sensor which may take the form of an additional thermocoupliec temperature measurement device.

A generator 600 may work with a wide range of catheters 155 that may be designed with different design requirements. In some embodiments, the catheter 155 may include some form of Non-Volatile Memory (NVM) in the disposable catheter 155 which can be used for a variety of purposes. This is often implemented with NVRAM or EEPROM embedded within the disposable or its connector (s) and this can usually be implemented at a very small incremental cost to the disposable itself. The first purpose of this NVM is the identification and serialization of the disposable. It is also common for the disposable memory to contain operational settings and/or limits for the disposable's operation. Modification of the contents of the disposable NVM by the generator itself can be used as a means to ensure a single use of the disposable. A less common use for large pin count systems is to include pin mapping within the NVM itself. This pin-mapping adds degrees of freedom to the manner in which the connections are attached to the connector, which can significantly simplify, and cost reduce the termination of the catheter. In some embodiments, pairs of leads from any probe could be connected to any pin pair on the connector. Since validation of the termination of every probe point will be required in the manufacturing process, the pin mapping could be automatically downloaded to the disposable memory in the manufacturing process. Another use of disposable memory is to store calibration constants for the catheter's operation.

Figure 11A:
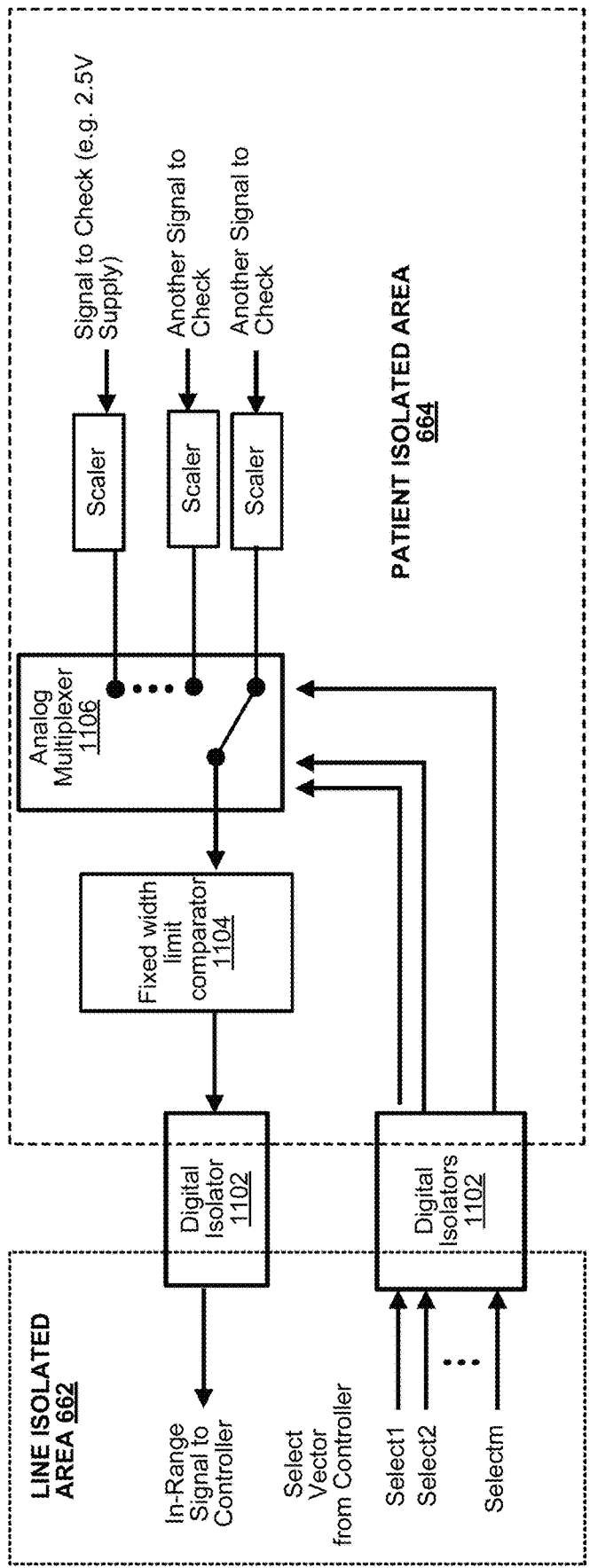
FIG. 11A is a block diagram illustrating the separation of the line isolated area and the patient isolated area, in accordance with some embodiments.
Figure 11B:
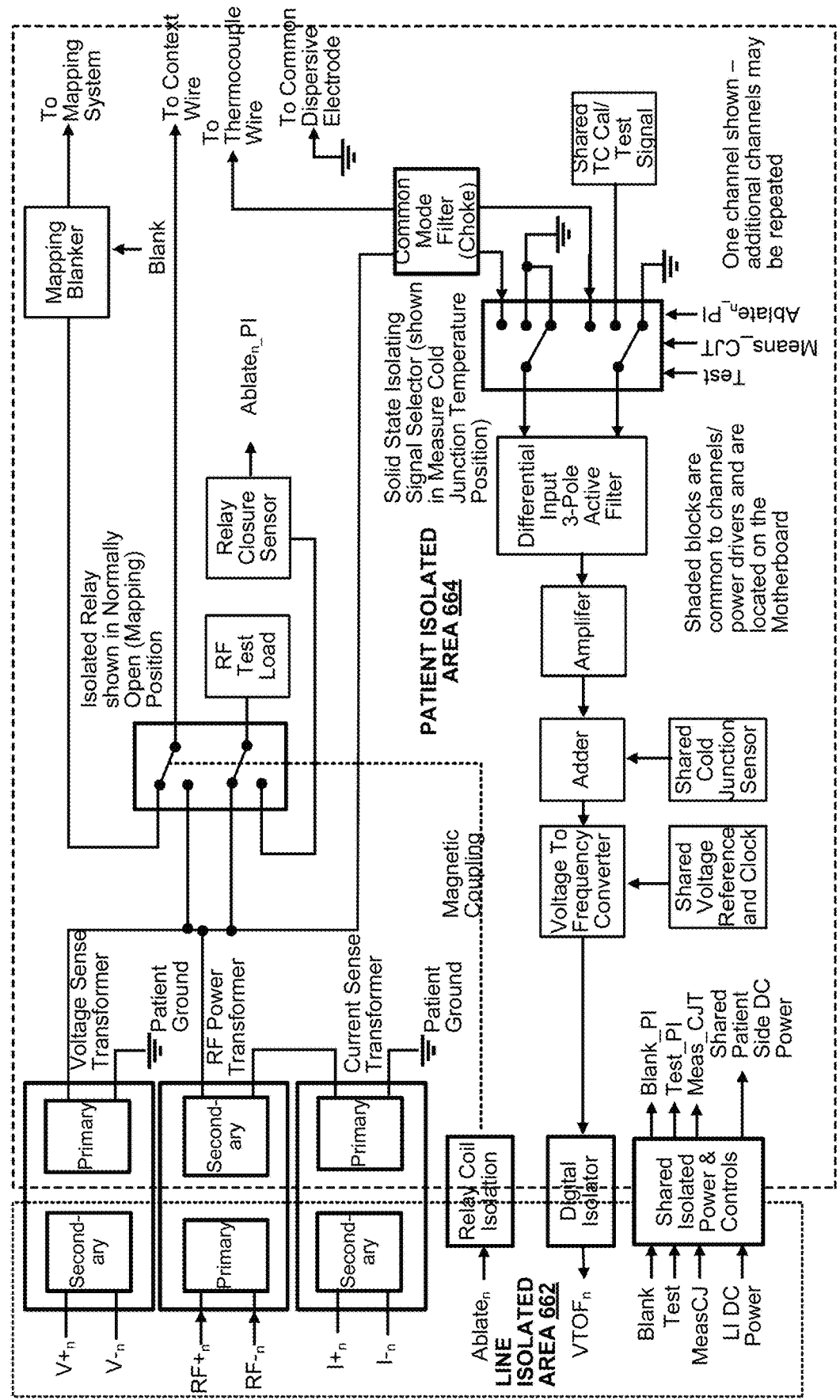
FIG. 11B is a block diagram illustrating an example circuitry of a patient isolated area, in accordance with some embodiments.

FIG. 11A is a block diagram illustrating the separation of the line isolated area 662 and the patient isolated area 664, in accordance with some embodiments. In some embodiments, the configuration might include an additional self-health monitor for the patient isolated area 664. Analog signals measured at the patients, such as thermocouple voltage or other electrical signals measured at the biological tissues, are converted before being transmitted back to the line isolated area 662 across the patient-line isolation boundary. The measured signals may be selected at the analog multiplexer 1106 and the fixed width limit comparator 1104. The patient-line isolation boundary may be implemented with one or more fixed width limit comparator schemes. The patient-line isolation boundary may include one or more digital isolator circuits 1102. A digital isolator may be used to relay the 1 MHz VTOF clock back to the controller 610 for verification to complete the self-health monitor. FIG. 11B is a block diagram illustrating an example circuitry of a patient isolated area 664, in accordance with some embodiments. The configuration of FIG. 11B illustrates an instance of a voltage sensor 624 that may be implemented as a cold junction sensor.

In some embodiments, an AC measurement system is included for each channel. Voltage and Current Peak amplitudes are detected using a pair of analog-comparator-based precision peak detector circuits. A matched phase shift filter pair is used to inject a precise 90° phase shift between the voltage and current waveforms. This permits unambiguous phase detection to be performed using a single exclusive or (XOR) gate. Integration of the XOR output generates an analog voltage proportional to phase with −90° generating 0 volts and +90° generating Full Scale (3.3 Volts). The Peak Voltage, Peak Current, and Relative Phase signals are converted to digital representation using channel microcontrollers 900 integrated analog-digital converter. AC Voltage and AC Current are sampled using appropriate isolation transformers and converted into a Voltage representative of the AC Voltage, Vv. and a Voltage representative of the AC Current, VI.

In the case of a current sense transformer, the body of the transformer may reside in the line isolated area 662, a pair of unplated holes permits a short length of 24 gauge, 6k VDC silicone rubber insulated wire to traverse the line-patient isolation boundary and complete the single turn primary winding in the patient isolated area 664. In the case of the voltage sense transformer, the body of the transformer may reside in the patient isolated area 664, a pair of unplated holes permits a short length of 24 gauge, 6 kVDC silicone rubber insulated wire to traverse the line-patient isolation boundary and complete the single turn secondary winding in the line isolated area 662. Parallel resonating capacitors are provided in the patient-isolated area to eliminate the inductive effects of the transformers at the fundamental frequency of 400 kHz.

A generator 600 may include an AC isolation relay. During AC delivery a voltage signal in excess of 200 Volts Peak-Peak may be applied to the electrode contacts. This may be used for certain types of energy delivery currently classified as pulsed-field ablation (PFA). Protective components may be used to protect against current amplitude. The first line of protection in the reduction of the amplitude is the AC routing relay which serves to disconnect the separate or integrated mapping system from the probe contact during AC delivery. A second function of the AC routing relay is to disconnect the AC drive electronics from the leads during mapping, because the low drive impedance highly attenuates the ECG signal, even in the absence of any AC delivery. This also ensures that there is no adverse loading or noise injection through this wire, which is physically connected to the probe lead at the distal end. A third function of the AC routing relay is to provide an independent means of interrupting the AC delivery, an important consideration for the Hazards Analysis (HA) and FMEA. A fourth function of the AC routing relay is to terminate the AC delivery system with a precision AC Test Load when the relay is in the disconnected state. This permits self-testing and/or calibration. A fifth function of the AC routing relay is to derive a patient-side digital signal indicative of the probe connectivity. This is achieved by sensing the connection/disconnection of the AC test load. This patient-side digital signal is used to re-configure the patient-side electronics when the tissue measurement/ablation is disabled. All of this functionality can be achieved with a single DPDT electromechanical relay.

Example Control System

Figure 12:
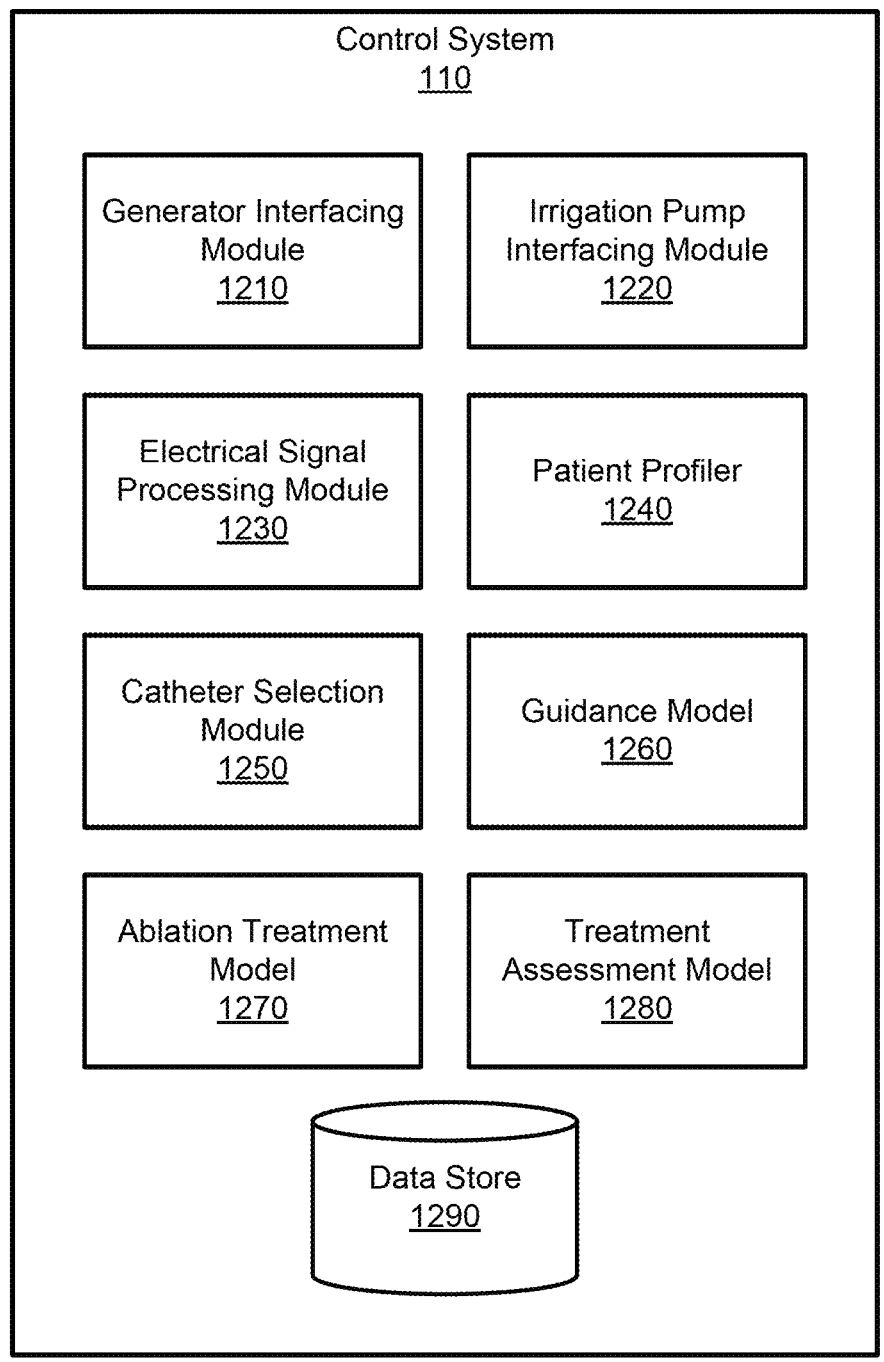
FIG. 12 illustrates a block diagram of the control system used in conjunction with the treatment device, in accordance with some embodiments.

FIG. 12 illustrates a block diagram of the control system 110 used in conjunction with the treatment device 105, in accordance with some embodiments. The control system 110 manages and controls the various components of the treatment system 100. The control system 110 may be a general computing system. The control system 110 includes various modules including, but not limited to, a generator interfacing module 1210, an irrigation pump interfacing module 1220, an electrical signal processing module 1230, a patient profiler 1240, a catheter optimization module 1250, a guidance model 1260, an ablation treatment model 1270, a treatment assessment model 1280, and a data store 1290. In other embodiments, additional or fewer modules may be implemented.

The generator interfacing module 1210 interfaces with the generator 115. In interfacing the generator 115, the generator interfacing module 1210 is configured to receive electrical signals from the generator 115 as measured by the electrode array of the catheter 155 of the treatment device 105. The electrical signals may be separated for each electrode of the electrode array. The generator interfacing module 1210 provides the electrical signals received from the generator 115 to the electrical signal processing module 1230. In addition, the generator interfacing module 1210 is configured to provide the generator 115 with instructions on performing an ablation procedure. The instructions can include a plurality of parameters for the ablation procedure. Example parameters may include, which electrodes to actuate during the ablation procedure, and for each electrode to be actuated for the ablation procedure, a frequency of the ablation energy, a waveform of the ablation energy, and a duration of the ablation energy.

The irrigation pump interfacing module 1220 interfaces with the irrigation pump 120. The irrigation pump interfacing module 1220 is configured to provide instructions on performing an ablation procedure to the irrigation pump 120. The instructions relevant to the irrigation pump may include which irrigant to use (in embodiments with multiple irrigants stored by the irrigation pump 120), how much irrigant to pump, for a particular duration, etc.

The electrical signal processing module 1230 processes the electrical signals measured by the electrode array of the catheter 155. The electrical signal processing module 1230 may perform one or more pre-processing techniques. Some example pre-processing techniques include noise filtering, annotation of the electrical signals, determining whether to discount a particular electrical signal due to recording artifacts, etc. In embodiments with other sensing devices, e.g., a non-invasive device with a wearable electrode array, the electrical signal processing module 1230 may also process the electrical signals measured by the other sensing devices.

The patient profiler 1240 maintains a patient profile for each of a plurality of patients. Each patient profile may include identifying information and medical records. Identifying information may include name, biological sex, age, and one or more current and/or prior medical conditions (e.g., asthmatic, diabetic, etc.). The medical records may include one or more prior diagnoses, one or more types of heart rhythm disorders that the patient has, one or more prior procedures, drug allergies, prior data streams, prior electrical signal data associated with a prior procedure, a current diagnosis, etc. The patient profiler 1240 may routinely update the patient profile upon the completion of a procedure. In one or more embodiments, the catheter optimization module 1250 selected a particular-sized catheter with a particular-sized electrode array for use in a given patient. The ablation procedure was successful in treating the patient's heart rhythm disorder. In response, the patient profile 1040 stores the selected catheter with the annotation of the procedure being successful. In a subsequent procedure, the patient profile including the prior success with the prior selected catheter can inform which catheter to select in the subsequent procedure.

Figure 13:
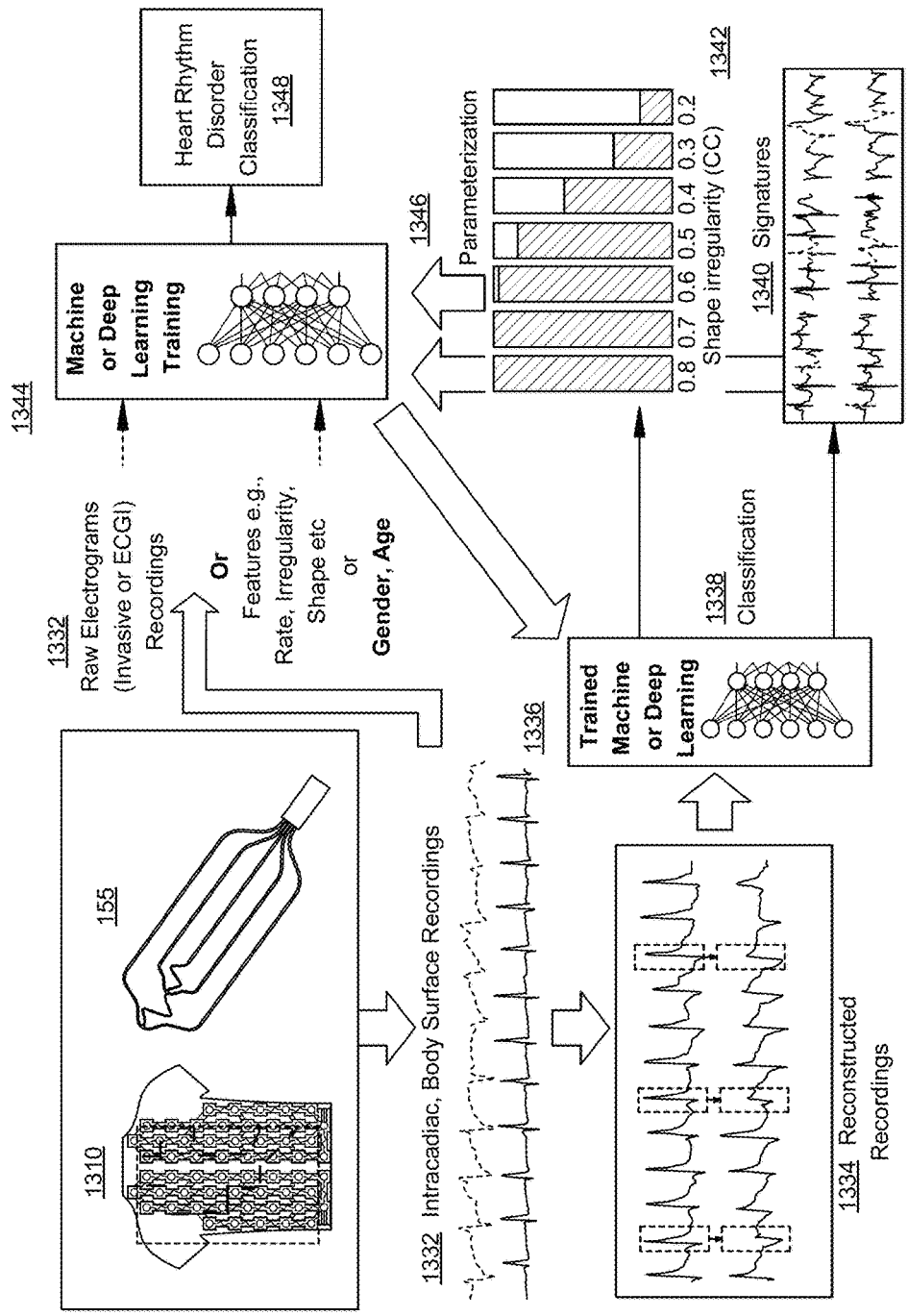
FIG. 13 illustrates a method of classifying a heart rhythm disorder of the patient.

In some embodiments, the electrical signal processing module 1230 extracts features from the electrical signals for use by other modules of the control system 110. Referring to FIG. 13, FIG. 13 illustrates one method 1336 of extracting specific rhythm signatures 1340 and shape irregularity 1342 from electrical signals 1332 measured by a sensing device (e.g., the electrode array of the treatment device 105 or an electrode array of another non-invasive sensing device). The features can be used to classify the rhythm, or identify special regions and/or special times within the rhythm disorder (e.g., by the guidance model 1260). These special times and/or regions can be treatment targets. In one or more embodiments, a non-invasive sensing device 1310 and/or electrical signals 1320 from the catheter 155 are used to generate the intracardiac and/or body surface recordings 1332. The electrical signal processing module 1230 can further reconstruct the recordings 1332 into the reconstructed recordings 1334. The algorithm 1336 for feature extraction is applied to these specific signals to extract the features, e.g., to create fingerprints or footprints or signatures 1340 of the rhythm. The extracted features may be useful in the refinement of the identification of the location of rhythm to classify right or left atrial or right or left ventricular origin. This can be structured to identify pulmonary veins from non-pulmonary vein regions for different embodiments. This can be useful to separate conditions such as atrial flutter from fibrillation, which guides therapy. This can also be useful to separate different forms of atrial fibrillation, such as those that can be treated by pulmonary vein isolation compared to forms that require therapy at additional areas outside the pulmonary veins. Similar algorithmic processes may be for other types of rhythm disorders that are not related to hearts, such as for seizure disorder in the brain, activity in the gastrointestinal tract, or nerve firing in a portion of the body in neurological illness.

The signatures 1340 may also identify a signal type that is a treatment target for the heart rhythm disorder, such as a region of slow conduction, of a viable channel of tissue within the scar, or fractionated signals, of high rates, of source or driver activity, and so on. The signatures 1340 may or may not be clear from analyses of the time-domain characteristics of the signal, such as amplitude, rate, or shape. The signatures 1340 may or may not be clear from analyses of the frequency domain characteristics of the signal, such as frequency, harmonics, or phase. The signatures 1340 may extend to signals from neighboring electrodes to form a preferred spatial region or cluster.

FIG. 13 further illustrates a method 1336 of classifying a heart rhythm disorder of the patient. The method 1336 implements one or more models, such as a classification model, to determine a type of heart rhythm disorder that is present in a given patient. The classification model inputs raw electrical signals, i.e., the recordings 1332, the reconstructed recordings 1334, the rhythm signatures 1340, the shape irregularities 1342, other data described herein in this disclosure, or some combination thereof. The parameters of the model used in method 1336 to extract the signatures can further serve as parametric information 1346 to inform the training of the classification model. The classification model 1344 outputs a heart rhythm disorder classification 1348 which identifies a particular type of heart rhythm disorder. The heart rhythm classification 1348 may inform which patterns to look out for in the electrical signals, as each heart rhythm disorder may have unique patterns.

In some embodiments, pre-processing may include high-pass filtering above 0.5 Hz to remove baseline oscillation or other artifacts, but others can be selected. In another embodiment, pre-processing can include low-pass filtering to remove electrical noise or other artifacts. Filtering can include also narrow-band pass filtering at the spectral band determined by features of the signal under analysis or other signals. For instance, some important features of AF in the frequency domain can be identified in bands of 0-20 Hz, such as the frequency of the main or secondary spectral contributions, their width and relative amplitude as well as the relative spectral content for certain frequency bands compared to the total spectral content. These features could be considered when selecting filters for signal acquisition. An embodiment could also use ventricular activity cancellation when the aim is to identify origin regions from the atrial chamber. In some embodiments, the ventricular cancellation algorithm is based on the detection of the instant of ventricular depolarization using a combination of linear and non-linear filtering and identification of local maxima. The ventricular cancellation algorithm could be based on ventricular shape average and subtraction using one or more torso signals. The ventricular cancellation algorithm could be based on partial component analysis using different ventricular beats.

The electrical signal processing module may perform spectral analysis of the torso signals, using the Fast Fourier Transform, the Welch Periodogram, the convolutional-based transform, or the continuous wavelet transform. The spectral analysis could be also based on the combination of spectral transformations after different linear or non-linear filtering, such as band-pass filtering or Bottteron and Smith filtering.

The spectral analysis could be used to detect the main spectral contribution using the following formula:

$$DF = \varepsilon(s_{ECG})|_{\vartheta(s_{ECG}) = max(\|\vartheta(s_{ECG})\|)}$$

In the above equation, DF is the main spectral contribution or Dominant Frequency, $s_{ECG}$ is the surface signal under analysis and $\vartheta(s_{ECC})$ represents the spectral transform by Fast Fourier Transform or Welch Periodogram. The electrical signal processing module may perform identification or other secondary spectral contributions using the local maxima of the spectral transform. The electrical signal processing module may perform an analysis of the spatial distribution of the DF values in order to identify regions with the same or different values of DF.

The electrical signal processing module may perform an analysis of the phase of the surface signal, using the following or another formula:

$$phase(t) = arctan(imag(hilbert(s_{ECG}(t))), hilbert(s_{ECG}(t)))$$

In the above equation, phase(t) is the instantaneous phase transform of the signal under analysis $s_{ECG}$, and imag( ) and hilbert( ) represents the imaginary-part extraction and Hilbert transform functions respectively. The electrical signal processing module may perform the analysis of the phase from individual signals, by identifying the fiducial points such as local maxima or transitions from/to pi/−pi. The electrical signal processing module may perform the analysis of several instantaneous phase signals in spatial maps, using spatial interpolation of the phase signal in each instant and position to cover all the surface torso between electrodes of the electrode array. This spatial interpolation could be carried out using linear interpolation, cubic splines, or other interpolation methods, and could be carried out without the use of torso anatomies and shapes extracted from medical image (MRI, CT) techniques. The electrical signal processing module may perform the analysis of the instantaneous phase maps through the identification of the phase transitions, that is, the lines in which the phase map transits from pi to −pi.

The electrical signal processing module 1230 may perform the analysis of spatial phase singularities using the following formula:

$$singularity\ (t) = \oint_{0,D}^{2\pi} phase\ (t)_{x,y}$$

In the above equation, the operator $$\oint_{0,D}^{2\pi}$$

represents the spatial integral over a circle with radius D and $s_{ECG}(t)_{x,y}$ is the electrocardiographic signal at interpolated coordinates X and Y. The computing server may perform identification of instants and points in which the singularity (t) provides values different to 0 and summarize and cluster them to measure the spatial and temporal complexity of heart arrhythmia. The computing server may perform the analysis of the temporal features of the electrocardiographic surface signal as the number of local maximal after band-pass filtering. The computing server may perform the analysis of the first and second derivatives of the torso surface signal in order to identify their percentiles and quartiles. The computing server may perform autocorrelation analysis of the electrocardiographic surface signals.

The catheter optimization module 1250 determines optimal specifications for catheter 155 for performing a procedure on a given patient. The catheter optimization module 1250 analyzes data associated with a given patient to determine the optimal specifications for the catheter 155. For example, based on the electrical signals measured for a patient (e.g., by an electrode array of the treatment device 105 or another non-invasive sensing device), the catheter optimization module 1250 determines an optimally sized catheter having an electrode array with a particular arrangement and a particular resolution. Some or all of the other data described herein in this disclosure (e.g., the rhythm signatures 1340 or other features extracted from the method 1336) can be considered in a model to determine the optimal specifications. In some embodiments, the model comprises a plurality of decision trees to determine the optimal specifications. In other embodiments, the model is a machine-learned model. A catheter 155 may be specially manufactured according to the optimal specifications. In other embodiments, a catheter 155 may be selected from a set of manufactured catheters, each having unique specifications, wherein the selected catheter 155 has specifications that closely match the optimal specifications determined. A physician implements the selected catheter 155 for use in the treatment device 105.

In some embodiments, directional guidance is tailored by patient data beyond recorded signals. These data may include clinical, pathophysiological, laboratory, genetic, or cellular elements. As an example, critical regions for AF may lie near the pulmonary veins in patients with early-stage disease, yet lie away from the pulmonary veins in patients with advanced disease, heart failure, or obstructive sleep apnea. Several other profiles profiles can be defined. Similarly, critical regions for ventricular tachycardia may reside in the left ventricle in patients with heart failure from coronary disease, yet in the right ventricle in patients with arrhythmogenic cardiomyopathy or advanced lung disease.

In some embodiments, techniques such as machine learning can classify an individual's data profiles based on patterns associated with response to therapy or lack of response to therapy. Machine learning may be trained by objective and clinically relevant labels such as successful response to therapy (e.g., elimination of AF by PVI ablation, elimination of VT by ablation, improvement in left ventricular ejection fraction by ablation of heart rhythm disorder), or adverse response to therapy (e.g., prolongation of the QT interval by pharmacological agents, failure from to ablation). The machine learning model can now make a prediction for an individual from their closest pattern match.

By using machine learning, the system individualizes treatment and does not cater just to the statistical majority of individuals who respond to therapy, or to populations most represented in the literature. This is a practical implementation of FAIR software methods (Findable, Accessible, Interoperable, and Reusable) to reduce bias—for instance, to cater therapy to an individual even if they differ demographically or physiologically from the 'average' patient in prior reported populations. This enables machine learning in this invention to be broadly generalizable to under-represented minorities even if training data is from a narrow population (e.g., Caucasians).

Personalization can be encoded by computer and analytical methods based on associative algorithms, data clusters including unsupervised machine learning, semi-supervised machine learning, and supervised machine learning and networks trained by labeled events in similar and dissimilar individuals. The tailoring of personal digital records to therapy is enabled by partitioning data with labels of 'healthful vs disease', 'responsive to therapy vs non-responsive', or multiclass response to therapies labeled such as 'therapy 1', 'therapy 2', . . . , 'therapy n'. Analysis can be one or more of supervised machine learning, neural networks, unsupervised machine learning, cluster analysis, correlation analyses, logistic regression analyses, decision trees, time domain analyses, frequency domain analyses, trigonometric transformations, and logarithmic transformations.

Personalization for heart rhythm may use signals that capture the rhythm. This may include electrical potentials (electrograms) from a non-invasive device or invasive device within or adjacent to the heart. Other signals that can be analyzed include heat (infrared), mechanical motion (piezoelectric or other sensors), chemical composition, blood flow and pressure (hemodynamics), wall tension (cardiac contractility and relaxation), Cardiac Images (magnetic resonance imaging, computed tomography), or other indices that may have diagnostic value. More detailed data includes three-dimensional anatomical and structural abnormalities. Clinical data can be extracted from history and physical examination, indices of pathophysiological comorbidities, blood and tissue biomarkers, and the genetic and cellular makeup of an individual. Non-invasively, sensors may record the standard electrocardiogram, surface recordings from higher resolution body surface potential mapping (e.g., multiple ECG electrodes) ECG imaging, and cutaneous measures of nerve activity. Reflectance on the skin to visible light or other electromagnetic waveforms can be used to measure signals that indicate heartbeats, either regular or irregular. This can be detected using photoplethysmography (PPG) or other forms of detecting reflectance. Visible light in the near-infrared portion of the spectrum may be useful for this. Other types of sensing signals that may be used will be apparent to one of ordinary skill in the art.

In some embodiments, a system may include a processor and a memory storing instructions that, when executed by the processor, perform operations including detecting bodily signals associated with one or more bodily functions at one or more sensors associated with the human body, processing the bodily signals to create one or more sensed signatures, processing the signatures using the digital object to determine an effector response, delivering one or more effector responses to control a bodily task and monitoring said response.

In some embodiments, a process can identify individuals amenable to therapy for treating complex rhythm disorders, provide directional guidance in 3 dimensions to move a sensor device towards optimal locations for therapy, and enable therapy to tissue at this location. In some embodiments, a non-invasive wearable device may be used by the patient at home, without hospital visits, to determine if ablation is likely to be successful or if drug therapy should be continued. This greatly improves outpatient workflow, and reduces unsuccessful procedures by better patient selection. Another embodiment is a system providing a personalized diagnosis of rhythm disorders and a 'single shot' sensor/therapy tool. Some embodiments, which are not intended to be limiting, include cardiac applications in heart rhythm disorders, coronary artery disease and in heart failure.

In some embodiments, the device is an artificial intelligence (AI) enabled non-invasive ECG device, simple enough to be applied to the chest or back by the patient at home. The single-use device will be worn for up to several days, will automatically detect the onset and then ongoing episodes of the heart rhythm disorder, and alert the user when sufficient data is recorded. Data is transmitted to the cloud for analysis, from which results will be available via electronic health records for review. Analysis can indicate if that patient will respond to ablation, if ablation is needed on the left or right side of the heart, and if they may respond to medications. The physician can then make a fully remote care plan, without the need for in-hospital evaluation or invasive testing. This is useful to streamline costs, provide access to patients in rural areas, and minimize hospital contact during public health emergencies such as the COVID-19 pandemic. One target indication is whether to refer an AF patient directly to pulmonary vein isolation (PVI), advanced ablation, or drug therapy choice.

The guidance model 1260 analyzes the electrical signals measured by the electrode array of the catheter 155 to determine directionality guidance for the catheter 155. The guidance model 1260 inputs at least the electrical signals measured by the electrode array of the catheter 155. In other embodiments, the guidance model 1260 further inputs other data, e.g., other electrical signals measured by a non-invasive sensing device. The signals may be raw or processed by one or more data processing techniques discussed under the electrical signal processing module 1230. The features are extracted using methods such as spectral or instantaneous phase analysis in single or combinations of electrodes. Other features may include features based on the temporal domain of the signal and their first and second derivative, such as percentiles, number of local maxima or minima, features extracted from the autocorrelation, rhythm signatures, shape irregularities, etc. Other features could be extracted from the parametric or signature analysis. Features are integrated with clinical variables such as age, and gender into a statistical classifier. The guidance model 1260 may be a multivariate regression or a supervised machine learning model using convolutional neural networks or support vector machines trained to a specific output label of AF termination or long-term outcome during algorithmic development. The guidance model 1260 may further output a personal digital record-based arrhythmia predictions, which can identify the specific phenotype of the patient disease such as a likely PV-based AF, AF from sites that arise away from the PVs, or VT that arises from sites common in patients with that phenotype.

The guidance direction is used to guide the movement of the catheter 155 of the treatment device 105 to the critical region of interest, e.g., a source or target region of the arrhythmia. In some embodiments, the physician guides the movement of the catheter 155 inside the patient. In such embodiments, the guidance direction can be displayed on the input/output device 125. In other embodiments the treatment device 105 may be motorized and automated, such that the guidance direction informs actuation of the motor to move the catheter 155 of the treatment device 105. The location algorithm is able to identify the position of the catheter 155 relative to the region of interest in the heart and guide the catheter 155 to the region of interest.

Upon reaching a region of interest, the guidance model 1260 verifies the arrival of the catheter 155 at the region of interest based on the electrical signals measured by the catheter 155. The guidance model 1260 determines whether the electrical signals at the anticipated region of interest match to known patterns for regions of interest. The guidance model 1260 can further analyze a ratio of the number of electrodes on the electrode array of the catheter 155 that are covered by the region of interest. One manner of calculating the ratio includes determining the area of the electrode array of the catheter 155 that covers the predicted region of interest. This is analogous to global positioning systems which use the current position to navigate to a desired location, without examining the entire map of the globe or remote sites. This approach enables higher resolution mapping than currently available in wide-area global or panoramic mapping systems within the heart. If the ratio is below some threshold, the guidance model 1260 determines additional guidance direction to optimize the position of the catheter 155 overlaying the region of interest. The guidance direction can include some translation (up to two degrees of freedom on the surface of the tissue) or some rotation (up to one degree of freedom, rotating about an axis perpendicular to the surface of the tissue).

In some embodiments, a non-invasive body surface mapping device uses a plurality of carefully placed electrodes on the body surface to map the heart rhythm disorder. In the prior art this typically needs anatomical information of the patient from detailed computed tomography (CT) or magnetic resonance imaging (MRI) data. However, the resolution needed to identify important patient groups or rhythm types can fulfilled without the need for computed tomography (CT) scan or magnetic resonance imaging (MRI) data. This increases the usability of the approach over existing methods based on medical image analysis (CT or MRI scans), since the body surface device is suitable for fully outpatient use without hospital visits for imaging. This is an advance over prior art methods such as Electrocardiogramaging (ECGI).

In some embodiments, navigational guidance to complement the electrode array catheter can be provided by body surface mapping without CT or MRI data, for instance to identify rhythms arising from the left side versus the right side of the heart, or separating beats originating from pulmonary vein regions of the left atrium (that project to the back) from other regions. This level of resolution can be achieved by body potential surface maps without CT or MRI data. This dispenses with the need for separate and cumbersome global 'basket' catheters.

One approach uses data from the body surface device. Another uses sophisticated directionality analysis from the electrode device inside the heart. A third combines these approaches. Directional guidance is enabled by a knowledge of the patterns of signals at the critical region, at neighboring regions, and at remote regions, and the use of signal processing (mathematical algorithms) including machine learning. This enables the system to indicate when the recording array is directly over the source. If the recording array is at a distance, then the guidance system can indicate directionality towards the source.

In some embodiments, the device can perform directional navigation from the body surface. For example, a body surface ECG may identify the location of critical regions for the heart rhythm disorder (FIG. 13). The system then calculates the direction or vector in which the electrode array catheter must be moved to reach each critical region for ablation. Directional navigation greatly advances over the prior art where the entire organ had to be mapped to identify a potentially small region of interest. One analogy is a satellite navigational system which computes directional guidance to enable a user to get from position A to B. The prior art required the user to examine and interpret a map of the city, county or country (or in the heart, a basket catheter of the global chamber) and then determine how to move from A and B. The current invention provides directionality information without requiring that the physician infer this themselves, which is subjective, or to use a separate global mapping apparatus which may introduce inaccuracies and inefficiencies into the procedure.

The ablation treatment model 1270 determines the parameters for an ablation procedure to be performed by the treatment device 105. The ablation treatment model 1270 inputs at least the electrical signals measured by the electrode array of the catheter 155. In other embodiments, the ablation treatment model 1270 further inputs other data, e.g., other electrical signals measured by a non-invasive sensing device. The signals may be raw or processed by one or more data processing techniques discussed under the electrical signal processing module 1230. The features are extracted using methods such as spectral or instantaneous phase analysis in single or combinations of electrodes. Other features may include features based in the temporal domain of the signal and their first and second derivative, such as percentiles, number of local maxima or minima, features extracted from the autocorrelation, rhythm signatures, shape irregularities, heart rhythm disorder classification, etc. Other features could be extracted from the parametric or signature analysis. Clinical variables such as age and gender may also be included as features. The ablation treatment model 1270 determines the parameters to ablate a source region that the catheter 155 of the treatment device 105 is in contact with. The parameters of the ablation procedure include select electrodes of the electrode array of the catheter 155 to actuate to deliver the ablation energy, the frequency of the ablation energy per electrode, the waveform of the ablation energy per electrode, the duration of the ablation energy per electrode, the irrigant to be delivered to the treatment site, the rate of irrigant flow, etc. The ablation procedure is provided to other components of the treatment system 100 for performing the ablation procedure.

The treatment assessment model 1280 verifies the success of an ablation procedure at a particular region of interest. The treatment assessment model 1280 collects electrical signals measured by the treatment device 105 after the ablation procedure has been performed. The electrical signals may be analyzed to determine whether the source region is still contributing to or affecting the heart rhythm disorder. In one or more embodiments, the verification process includes movement of the catheter 155 to one or more adjacent positions to the ablated region to sense and analyze electrical signals.

The data store 1290 stores all the various data of the control system 110. The data store 1290 may be one or more computing devices that include memories or other storage media for data related to the patients, e.g., in patient profiles generated by the patient profiler 1240, such as data measured by the treatment device 105. Some of the data may take the form of personal digital records. The data may be routed by the control system 110. The data store 1290 may be a network-based storage server (e.g., a cloud server). The data store 1290 may be part of the computing server or may be a third-party storage system such as AMAZON AWS, AMAZON S3, DROPBOX, RACKSPACE CLOUD FILES, AZURE BLOB STORAGE, GOOGLE CLOUD STORAGE or ENGINE, etc.

Treatment Process

FIG. 14 is a flowchart depicting a process 1400 for ablating tissue to treat a rhythm disorder, in accordance with some embodiments. The rhythm disorder may be a heart rhythm disorder. In various embodiments, the process may include additional, fewer, or different steps.

In some embodiments, the process 1400 may include applying 1410 a catheter to a biological issue. The catheter includes an electrode configured to deliver ablation energy to the biological tissue. The electrode may include a junction of two different materials. In some embodiments, the two materials respectively form a first conductive wire and a second wire. The first conductive wire and the second wire are part of the circuitry for delivering the ablation energy.

In some embodiments, the process 1400 may include measuring 1420, simultaneously for at least a moment, a thermocouple voltage at the junction of the two different materials. In some embodiments, the catheter includes an array of electrodes. The process 1400 may include detecting biological electrical signals measured at the array of electrodes. The process 1400 may also include determining the directionality of a source of the heart rhythm disorder based on the biological electrical signals.

In some embodiments, the process 1400 may include determining 1430 a temperature of the electrode based on the thermocouple voltage. In some embodiments, the temperature may be determined as being above a threshold. An irrigation pump is activated to deliver coolant to lower the temperature measured at the electrode In some embodiments, the process 1400 may include regulating 1440 a power generator that generates a current delivered to the electrode of the catheter based on the temperature. In some embodiments, the catheter may include a plurality of electrodes. The power generator may include a plurality of power drivers. The process 1400 may further include adjusting each power driver to individually regulate a current sent to a respective electrode of the catheter. The plurality of electrodes may include a plurality of conductive wires and share a common return wire.

In some embodiments, the catheter may include a plurality of thermocouple electrodes and the power generator may include a plurality of voltage sensors. The process 1400 may further include measuring, using each of the voltage sensors, a thermocouple voltage of a respective thermocouple electrode. The process 1400 may further include determining temperatures of the plurality of thermocouple electrodes. The process 1400 may further include regulating, individually, currents delivered to the plurality of thermocouple electrodes based on the temperatures.

In some embodiments, regulating 1440 the power generator that generates the current delivered to the electrode of the catheter based on the temperature may include determining a target amplitude of the current based on the temperature; generating an alternating current; and filtering the alternating current based on a target frequency.

In some embodiments, the current is delivered at a target frequency higher than 200 kHz. In some embodiments, the current is delivered at a target frequency higher than 300 kHz. In some embodiments, the current is delivered at a target frequency around 400 kHz. In some embodiments, the current is an alternating current that has a monochromatic frequency.

Computing Machine Architecture

Figure 15:
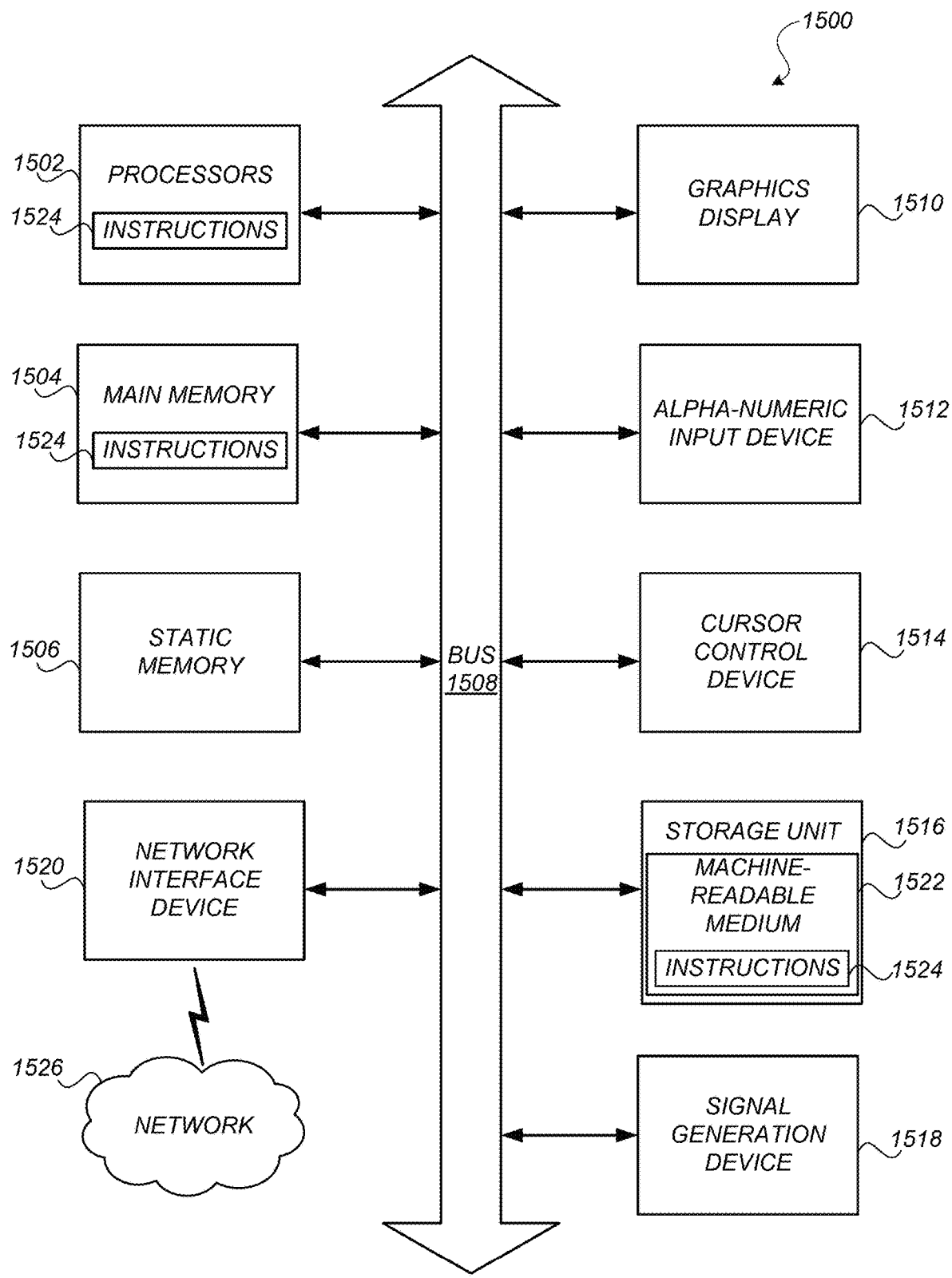
FIG. 15 is a block diagram illustrating components of an example computing machine, in accordance with some embodiments.

FIG. 15 is a block diagram illustrating components of an example computing machine that is capable of reading instructions from a computer-readable medium and executing them in a processor (or controller). A computer described herein may include a single computing machine shown in FIG. 15, a virtual machine, a distributed computing system that includes multiple nodes of computing machines shown in FIG. 15, or any other suitable arrangement of computing devices.

By way of example, FIG. 15 shows a diagrammatic representation of a computing machine in the example form of a computer system 1500 within which instructions 1524 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 15 may correspond to any software, hardware, or combined components discussed in this disclosure. While FIG. 15 shows various hardware and software elements, each of the components described may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1524 that specify actions to be taken by that machine. Further, while only a single machine is illustrated, the terms "machine" and "computer" may also be taken to include any collection of machines that individually or jointly execute instructions 1524 to perform any one or more of the methodologies discussed herein.

The example computer system 1500 includes one or more processors 1502 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1500 may also include a memory 1504 that stores computer code including instructions 1524 that may cause the processors 1502 to perform certain actions when the instructions are executed, directly or indirectly by the processors 1502. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One or more methods described herein improve the operation speed of the processor 1502 and reduce the space required for the memory 1504. For example, the signal processing techniques and machine learning methods described herein reduce the complexity of the computation of the processors 1502 by applying one or more novel techniques that simplify the steps in training, reaching convergence, and generating results of the processors 1502. The algorithms described herein also reduce the size of the models and datasets to reduce the storage space requirement for memory 1504.

The performance of certain operations may be distributed among more than one processor, not only residing within a single machine, but deployed across a number of machines. In some example embodiments, the one or more processors or processor-implemented modules may be located in a single geographic location (e.g., within a home environment, an office environment, or a server farm). In other example embodiments, one or more processors or processor-implemented modules may be distributed across a number of geographic locations. Even though the specification or the claims may refer to some processes to be performed by a processor, this may be construed to include a joint operation of multiple distributed processors. In some embodiments, a computer-readable medium comprises one or more computer-readable media that, individually, together, or distributedly, comprise instructions that, when executed by one or more processors, cause the one or more processors to perform, individually, together, or distributedly, the steps of the instructions stored on the one or more computer-readable media. Similarly, a processor comprises one or more processors or processing units that, individually, together, or distributedly, perform the steps of instructions stored on a computer-readable medium. In various embodiments, the discussion of one or more processors that carry out a process with multiple steps does not require any one of the processors to carry out all of the steps. For example, a processor A can carry out step A, a processor B can carry out step B using, for example, the result from the processor A, and a processor C can carry out step C, etc. The processors may work cooperatively in this type of situation such as in multiple processors of a system in a chip, in Cloud computing, or in distributed computing.

The computer system 1500 may include a main memory 1504, and a static memory 1506, which are configured to communicate with each other via a bus 1508. The computer system 1500 may further include a graphics display unit 1510 (e.g., a plasma display panel (PDP), a liquid crystal display (LCD), a projector, or a cathode ray tube (CRT)). The graphics display unit 1510, controlled by the processor 1502, displays a graphical user interface (GUI) to display one or more results and data generated by the processes described herein. The computer system 1500 may also include an alphanumeric input device 1512 (e.g., a keyboard), a cursor control device 1514 (e.g., a mouse, a trackball, a joystick, a motion sensor, or other pointing instruments), a storage unit 1516 (a hard drive, a solid-state drive, a hybrid drive, a memory disk, etc.), a signal generation device 1518 (e.g., a speaker), and a network interface device 1520, which also are configured to communicate via the bus 1508.

The storage unit 1516 includes a computer-readable medium 1522 on which is stored instructions 1524 embodying any one or more of the methodologies or functions described herein. The instructions 1524 may also reside, completely or at least partially, within the main memory 1504 or within the processor 1502 (e.g., within a processor's cache memory) during execution thereof by the computer system 1500, the main memory 1504 and the processor 1502 also constituting computer-readable media. The instructions 1524 may be transmitted or received over a network 1526 via the network interface device 1520.

While computer-readable medium 1522 is shown in an example embodiment to be a single medium, the term "computer-readable medium" should be taken to include a single medium or multiple media (e.g., a centralized or distributed database, or associated caches and servers) able to store instructions (e.g., instructions 1524). The computer-readable medium may include any medium that is capable of storing instructions (e.g., instructions 1524) for execution by the processors (e.g., processors 1502) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Example Embodiments

Embodiment 1. A power generator for generating ablating energy for a catheter to treat a heart rhythm disorder, the power generator comprising: a first power driver having a first port configured to be connected to a first wire of a first electrode of the catheter to deliver a first current to the first electrode to generate first ablation energy for treatment of a biological tissue; a second power driver having a second port configured to be connected to a second wire of a second electrode of the catheter to deliver a second current to the second electrode to generate second ablation energy for treatment of the biological tissue, wherein the first power driver and the second power driver are capable of generating different currents and delivering the different currents respectively to the first electrode and the second electrode of the catheter; a first voltage sensor configured to measure a first thermocouple voltage corresponding to the first wire of the first electrode of the catheter; a second voltage sensor configured to measure a second thermocouple voltage corresponding to the second wire of the second electrode of the catheter; and a controller configured to: determine a first temperature corresponding to the first electrode based on the first thermocouple voltage; determine a second temperature corresponding to the second electrode based on the second thermocouple voltage; regulate the first power driver and the second power driver to maintain the first temperature and the second temperature within a predetermined range of temperature for at least 90% of duration.

Embodiment 2. The power generator of embodiment 1, wherein the predetermined range is within 2C above or below a target temperature.

Embodiment 3. The power generator of embodiment 1 or claim 2, wherein transient changes in the first temperature and the second temperature are maintained within a second predetermined range is within 4C above or below a target temperature.

Embodiment 4. The power generator of any of embodiments 1-3, wherein the treatment is caused by pulsed field ablation.

Embodiment 5. The power generator of any of embodiments 1-4, wherein magnitude and duration of energy are delivered with a range consistent with pulsed filed ablation.

Embodiment 6. The power generator of any of embodiments 1-5, wherein the treatment is caused by radiofrequency.

Embodiment 7. The power generator of any of embodiments 1-6, wherein magnitude and duration of energy are delivered with a range consistent with radiofrequency ablation.

Embodiment 8. The power generator of any of embodiments 1-7, further comprising a plurality of power drivers comprising the first power driver and the second power driver and a plurality of voltage sensors comprising the first voltage sensor and the second voltage sensor, wherein each of the plurality of voltage sensors is configured to individually sense temperature of a respective electrode and each of the plurality of power driver is configured to individually regulate a current sent to the respective electrode.

Embodiment 9. The power generator of any of embodiments 1-8, wherein the first power driver and the second power driver are configured to generate alternating currents.

Embodiment 10. The power generator of any of embodiments 1-9, wherein the controller is further configured to regulate the first current and the second current based on the first temperature and the second temperature.

Embodiment 11. The power generator of any of embodiments 1-10, wherein the first thermocouple voltage is a result of a first thermocouple at a junction of the first wire formed of a first material and a second material that is different from the first material.

Embodiment 12. The power generator of embodiment 11, wherein the first wire, the second material and the first power driver form circuitry for the first current to be delivered.

Embodiment 13. The power generator of any of embodiments 1-12, wherein the controller is further configured to process a biological electrical signal indicative of a location of the heart rhythm disorder.

Embodiment 14. The power generator of any of embodiments 1-13, wherein the biological electrical signal is any one of: current, voltage, and/or impedance Embodiment 15. The power generator of any of embodiments 1-14, wherein the first power driver further comprises a first frequency filter circuit configured to filter the first current to a first target frequency and the second power driver further comprises a second frequency filter circuit configured to filter the second current to a second target frequency.

Embodiment 16. The power generator of embodiment 15, wherein the first target frequency and the second target frequency are within 5% difference.

Embodiment 17. The power generator of embodiment 15, wherein the first frequency filter circuit and the second frequency filter circuit are band-pass filters.

Embodiment 18. The power generator of embodiment 15, wherein the first target frequency and the second target frequency are higher than 200 kHz.

Embodiment 19. The power generator of embodiment 15, the first frequency filter circuit and the second frequency filter circuit are harmonic filters that filter out harmonic frequencies that are higher than a fundamental frequency.

Embodiment 20. The power generator of any of embodiments 1-19, wherein the first power driver is configured to generate a first monochromatic frequency current and the second power driver is configured to generate a second monochromatic frequency current.

Embodiment 21. The power generator of any of embodiments 1-20, wherein the first voltage sensor is configured to measure a first voltage between the first wire and a return wire and the second voltage sensor is configured to measure a second voltage between the second wire and the return wire shared with the first wire.

Embodiment 22. The power generator of any of embodiments 1-21, wherein the controller is configured to regulate generation of currents based on attenuation of electrical signal amplitude.

Embodiment 23. The power generator of any of embodiments 1-22, wherein the controller is configured to regulate generation of currents based on reduction of complex impedance.

Embodiment 24. The power generator of any of embodiments 1-23, wherein the first power driver and the second power driver are synchronized by a clock.

Embodiment 25. The power generator of any of embodiments 1-24, further comprising a patient isolation circuit to prevent a patient from receiving an electrical shock.

Embodiment 26. The power generator of any of embodiments 1-25, wherein the first power driver and the second power driver are configured to generate bipolar pulsed field radiofrequency energy.

Embodiment 27. A catheter for ablating tissue to treat a heart rhythm disorder, the catheter comprising: a first conductive wire formed of a first material, the first conductive wire configured to be connected to a power generator and to carry a current to deliver ablation energy to a biological tissue; a second wire coupled to the first conductive wire, the second wire formed of a second material different from the first material, the second wire forming a junction with the first conductive wire; and a first electrode of the catheter, the first electrode comprising an ablation element and a temperature sensor, wherein the ablation element is formed as a part of the first conductive wire and is configured to deliver the ablation energy to the biological tissue, and wherein the temperature sensor comprises the junction of the first conductive wire and the second wire such that a thermocouple between the first conductive wire and the second wire is formed at the junction to measure temperature at the first electrode.

Embodiment 28. The catheter of any of embodiment 27, wherein the first electrode is part of a set of electrodes that comprises a second electrode, wherein the catheter further comprises a return wire, and wherein the first electrode and the second electrode share the return wire.

Embodiment 29. The catheter of embodiment 28, wherein each electrode in the set of electrodes is capable of delivering ablation energy at a different level independent of other electrodes in the set.

Embodiment 30. The catheter of embodiment 28, wherein each electrode in the set of electrodes comprises a temperature sensor configured to measure temperature at the respective electrode.

Embodiment 31. The catheter of embodiment 28, wherein the second electrode comprises a second ablation element and a second temperature sensor, and the second electrode further comprises: a third conductive wire formed of the first material, the third conductive wire configured to carry a second current and configured to serve as part of the second ablation element to deliver ablation energy; and a fourth wire formed of the second material different from the first material, the fourth wire forming a second junction with the third conductive wire, wherein a second thermocouple between the third conductive wire and the fourth wire forms at least part of the second temperature sensor configured to measure temperature at the second electrode.

Embodiment 32. The catheter of embodiment 31, wherein the second wire of the first electrode and the fourth wire of the second electrode are connected to the return wire at an intermediate junction.

Embodiment 33. The catheter of embodiment 31, wherein the first conductive wire of the first electrode is configured to be connected to first circuitry configured to measure a first voltage between the first conductive wire and the return wire, and the third conductive wire of the second electrode is configured to be connected to second circuitry configured to measure a second voltage between the third conductive wire and the return wire.

Embodiment 34. The catheter of embodiment 28, wherein the set of electrodes are arranged in a two-dimensional array.

Embodiment 35. The catheter of any of embodiments 27-34, wherein the first electrode is further configured to sense an electrical signal.

Embodiment 36. The catheter of embodiment 35, wherein the electrical signal is any one of: current, voltage, and/or impedance.

Embodiment 37. The catheter of any of embodiments 27-36, wherein the first material has a first impedance and the second material has a second impedance that is higher than the first impedance.

Embodiment 38. The catheter of any of embodiments 27-37, wherein the first electrode is configured to deliver an alternating current as the current that delivers the ablation energy.

Embodiment 39. The catheter of embodiment 38, wherein the alternating current has a monochromatic frequency.

Embodiment 40. The catheter of embodiment 39, wherein the monochromatic frequency is higher than 200 kHz.

Embodiment 41. The catheter of any of embodiments 27-40, wherein the second wire is part of circuitry of the first electrode and serves as part of a return path of the circuitry.

Embodiment 42. The catheter of any of embodiments 27-41, wherein the first material is copper and the second material is constantan.

Embodiment 43. The catheter of any of embodiments 27-42, wherein the first electrode is capable of simultaneously delivering the ablation energy and sensing the temperature at the first electrode.

Embodiment 44. The catheter of any of embodiments 27-43, wherein a majority of the first conductive wire and a majority of the second wire are insulated and wherein the first electrode is formed of an exposed part of the first conductive wire and an exposed part of the second wire.

Embodiment 45. The catheter of embodiment 44, wherein the junction of the first conductive wire and the second wire is part of the exposed part of the first conductive wire and the exposed part of the second wire.

Embodiment 46. The catheter of any of embodiments 27-45, wherein the first electrode comprises a single circuitry that serves as both the ablation element and the temperature sensor.

Embodiment 47. A system for ablating tissue to treat a heart rhythm disorder, the system comprising: a catheter for ablating tissue to treat a heart rhythm disorder, the catheter comprising: a first conductive wire formed of a first material, the first conductive wire configured to deliver ablation energy to a biological tissue; a second wire coupled to the first conductive wire, the second wire formed of a second material different from the first material; and an electrode comprising a junction of the first conductive wire and the second wire; a power generator coupled to the catheter for powering the catheter, the power generator comprising: a power driver configured to be connected to the first conductive wire of the catheter to deliver a current to the electrode to deliver the ablation energy; and a voltage sensor configured to measure a thermocouple voltage at the junction of the first conductive wire and the second wire.

Embodiment 48. The system of embodiment 47, wherein the catheter further comprises a plurality of electrodes and the power generator further comprises a plurality of power drivers, and each of the power drivers individually regulates a current sent to a respective electrode of the catheter.

Embodiment 49. The system of embodiment 48, wherein the plurality of electrodes comprises a plurality of conductive wires and share a common return wire.

Embodiment 50. The system of any of embodiments 47-49, wherein the catheter further comprises a plurality of thermocouple electrodes and the power generator further comprises a plurality of voltage sensors, and each of the voltage sensors individually senses temperature of a respective thermocouple electrode.

Embodiment 51. The system of any of embodiments 47-50, further comprising a controller configured to regulate the current based on the thermocouple voltage.

Embodiment 52. The system of any of embodiments 47-51, wherein the first conductive wire, the second wire, and the power driver form circuitry for the current to be delivered.

Embodiment 53. The system of any of embodiments 47-52, wherein the power driver is configured to generate alternating current, and the power driver further comprises a frequency filter circuit configured to filter the alternating current to a target frequency, and whether the electrode of the catheter is configured to deliver the ablation energy via the alternating current.

Embodiment 54. The system of embodiment 53, wherein the target frequency is higher than 200 kHz.

Embodiment 55. The system of embodiment 53, wherein the alternating current is a monochromatic frequency current.

Embodiment 56. The system of any of embodiments 47-55, wherein the first material has a first impedance and the second material has a second impedance that is higher than the first impedance.

Embodiment 57. A method for ablating tissue to treat a heart rhythm disorder, the method comprising: applying a catheter to a biological issue, the catheter comprising an electrode configured to deliver ablation energy to the biological tissue, the electrode comprising a junction of two different materials; measuring, simultaneously for at least a moment, a thermocouple voltage at the junction of the two different materials; determining a temperature of the electrode based on the thermocouple voltage; and regulating a power generator that generates a current delivered to the electrode of the catheter based on the temperature.

Embodiment 58. The method of embodiment 57, wherein the catheter further comprises a plurality of electrodes and the power generator further comprises a plurality of power drivers, and the method further comprises: adjusting each power driver to individually regulate a current sent to a respective electrode of the catheter.

Embodiment 59. The method of embodiment 58, wherein the plurality of electrodes comprises a plurality of conductive wires and share a common return wire.

Embodiment 60. The method of any of embodiments 57-59, wherein the catheter further comprises a plurality of thermocouple electrodes and the power generator further comprises a plurality of voltage sensors, and the method further comprises: measuring, using each of the voltage sensors, a thermocouple voltage of a respective thermocouple electrode; determining temperatures of the plurality of thermocouple electrodes; and regulating, individually, currents delivered to the plurality of thermocouple electrodes based on the temperatures.

Embodiment 61. The method of any of embodiments 57-60, wherein regulating the power generator that generates the current delivered to the electrode of the catheter based on the temperature comprises: determining a target amplitude of the current based on the temperature; generating an alternating current; and filtering the alternating current based on a target frequency.

Embodiment 62. The method of any of embodiments 57-61, wherein the current is delivered at a target frequency is higher than 200 kHz.

Embodiment 63. The method of any of embodiments 57-62, wherein the current is an alternating current that has a monochromatic frequency.

Embodiment 64. The method of any of embodiments 57-63, wherein the two materials respectively form a first conductive wire and a second wire, and the first conductive wire and the second wire are part of circuitry for delivering the ablation energy.

Embodiment 65. The method of any of embodiments 57-64, further comprising: determining the temperature being above a threshold; and activating an irrigation pump to deliver coolant to lower the temperature measured at the electrode.

Embodiment 66. The method of any of embodiments 57-65, wherein the catheter comprises an array of electrodes, and the method further comprises: detecting biological electrical signals measured at the array of electrodes; and determining a directionality of a source of the heart rhythm disorder based on the biological electrical signals.

ADDITIONAL CONSIDERATIONS

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, or storage medium, as well. The dependencies or references in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcodes, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed in the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The invention claimed is:

1. A power generator for generating ablating energy for a catheter to treat a heart rhythm disorder, the power generator comprising:
  a first power driver having a first port configured to be connected to a first wire of a first electrode of the catheter to deliver a first current to the first electrode to generate first ablation energy for treatment of a biological tissue;
  a second power driver having a second port configured to be connected to a second wire of a second electrode of the catheter to deliver a second current to the second electrode to generate second ablation energy for treatment of the biological tissue, wherein the first power driver and the second power driver are capable of generating different currents and delivering the different currents respectively to the first electrode and the second electrode of the catheter;
  a first voltage sensor configured to measure a first thermocouple voltage corresponding to the first wire of the first electrode of the catheter;
  a second voltage sensor configured to measure a second thermocouple voltage corresponding to the second wire of the second electrode of the catheter; and
  a controller configured to:
    determine a first temperature corresponding to the first electrode based on the first thermocouple voltage;
    determine a second temperature corresponding to the second electrode based on the second thermocouple voltage;
    regulate the first power driver and the second power driver to maintain the first temperature and the second temperature within a predetermined range of temperature for at least 90% of duration.

2. The power generator of claim 1, wherein the predetermined range is within 2C above or below a target temperature.

3. The power generator of claim 1, wherein transient changes in the first temperature and the second temperature are maintained within a second predetermined range is within 4C above or below a target temperature.

4. The power generator of claim 1, wherein the treatment is caused by pulsed field ablation.

5. The power generator of claim 1, wherein magnitude and duration of energy are delivered with a range consistent with pulsed filed ablation.

6. The power generator of claim 1, wherein the treatment is caused by radio frequency.

7. The power generator of claim 1, wherein magnitude and duration of energy are delivered with a range consistent with radio frequency ablation.

8. The power generator of claim 1, further comprising a plurality of power drivers comprising the first power driver and the second power driver and a plurality of voltage sensors comprising the first voltage sensor and the second voltage sensor, wherein each of the plurality of voltage sensors is configured to individually sense temperature of a respective electrode and each of the plurality of power driver is configured to individually regulate a current sent to the respective electrode.

9. The power generator of claim 1, wherein the first power driver and the second power driver are configured to generate alternating currents.

10. The power generator of claim 1, wherein the controller is further configured to regulate the first current and the second current based on the first temperature and the second temperature.

11. A system for ablating tissue to treat a heart rhythm disorder, the system comprising:
  a catheter for ablating tissue to treat a heart rhythm disorder, the catheter comprising:
    a first conductive wire formed of a first material, the first conductive wire configured to deliver ablation energy to a biological tissue;
    a second wire coupled to the first conductive wire, the second wire formed of a second material different from the first material; and
    a plurality of electrodes, wherein a first electrode of the plurality of electrodes comprises a junction of the first conductive wire and the second wire;
  a power generator coupled to the catheter for powering the catheter, the power generator comprising:
    a plurality of power drivers, wherein a first power driver is configured to be connected to the first conductive wire of the catheter to deliver a current to the electrode to deliver the ablation energy, and wherein each of the power drivers of the plurality of power drivers is configured to individually regulate a respective current sent to a respective electrode of the plurality of electrodes of the catheter; and
    a voltage sensor configured to measure a thermocouple voltage at the junction of the first conductive wire and the second wire.

12. The system of claim 11, wherein the plurality of electrodes comprises a plurality of conductive wires and share a common return wire.

13. The system of claim 11, wherein the catheter further comprises a plurality of thermocouple electrodes and the power generator further comprises a plurality of voltage sensors, and each of the voltage sensors individually senses temperature of a respective thermocouple electrode.

14. The system of claim 11, further comprising a controller configured to regulate the current based on the thermocouple voltage.

15. The system of claim 11, wherein the first conductive wire, the second wire, and the power driver form circuitry for the current to be delivered.

16. The system of claim 11, wherein the power driver is configured to generate alternating current, and the power driver further comprises a frequency filter circuit configured to filter the alternating current to a target frequency, and whether the first electrode of the catheter is configured to deliver the ablation energy via the alternating current.

17. The system of claim 16, wherein the target frequency is higher than 200 kHz.

18. The system of claim 16, wherein the alternating current is a monochromatic frequency current.

19. The system of claim 11, wherein the first material has a first impedance and the second material has a second impedance that is higher than the first impedance.

20. A method for ablating tissue to treat a heart rhythm disorder, the method comprising:
- applying a catheter to a biological issue, the catheter comprising a plurality of electrodes, wherein a first electrode is configured to deliver ablation energy to the biological tissue, the first electrode comprising a junction of two different materials;
- measuring, simultaneously for at least a moment, a thermocouple voltage at the junction of the two different materials;
- determining a temperature of the electrode based on the thermocouple voltage;
- regulating a power generator that generates a current delivered to the first electrode of the catheter based on the temperature, wherein the power generator comprises a plurality of power drivers; and
- adjusting each power driver of the plurality of power drivers of the power generator to individually regulate a respective current sent to a respective electrode of the catheter.

21. The method of claim 20, wherein the plurality of electrodes comprises a plurality of conductive wires and share a common return wire.

22. The method of claim 20, wherein the catheter further comprises a plurality of thermocouple electrodes and the power generator further comprises a plurality of voltage sensors, and the method further comprises:
- measuring, using each of the voltage sensors, a thermocouple voltage of a respective thermocouple electrode;
- determining temperatures of the plurality of thermocouple electrodes; and
- regulating, individually, currents delivered to the plurality of thermocouple electrodes based on the temperatures.

23. The method of claim 20, wherein regulating the power generator that generates the current delivered to the first electrode of the catheter based on the temperature comprises:
- determining a target amplitude of the current based on the temperature;
- generating an alternating current; and
- filtering the alternating current based on a target frequency.

24. The method of claim 20, wherein the current is delivered at a target frequency is higher than 200 kHz.

25. The method of claim 20, wherein the current is an alternating current that has a monochromatic frequency.

26. The method of claim 20, wherein the two materials respectively form a first conductive wire and a second wire, and the first conductive wire and the second wire are part of circuitry for delivering the ablation energy.

27. The method of claim 20, further comprising:
- determining the temperature being above a threshold; and
- activating an irrigation pump to deliver coolant to lower the temperature measured at the first electrode.

28. The method of claim 20, further comprising:
- detecting biological electrical signals measured at the plurality of electrodes; and
- determining a directionality of a source of the heart rhythm disorder based on the biological electrical signals.

* * * * *